(12) United States Patent
Pontes Meireles Ferreira de Brito et al.

(10) Patent No.: US 11,584,727 B2
(45) Date of Patent: Feb. 21, 2023

(54) 2-THIOXOTHIAZOLIDIN-4-ONE DERIVATIVES ACTIVE AS TRANSTHYRETIN LIGANDS AND USES THEREOF

(71) Applicant: BSIM Therapeutics, S.A., Coimbra (PT)

(72) Inventors: Rui Manuel Pontes Meireles Ferreira de Brito, Coimbra (PT); Carlos José Vieira Simões, Cantanhede (PT); Teresa Margarida Vasconcelos Dias de Pinho e Melo, Coimbra (PT); Bruno Lourenço da Silva Victor, Cantanhede (PT); Zaida Catarina Lourenço de Almeida, Coimbra (PT); Ana Lúcia Cabral Cardoso Lopes, Coimbra (PT); Bruno Filipe Oliveira Nascimento, Coimbra (PT)

(73) Assignee: BSIM Therapeutics, S.A., Coimbra (PT)

( * ) Notice: Subject to any disclaimer, the term of this patent is extended or adjusted under 35 U.S.C. 154(b) by 0 days.

(21) Appl. No.: 17/405,506

(22) Filed: Aug. 18, 2021

(65) Prior Publication Data

US 2022/0041566 A1 Feb. 10, 2022
US 2022/0267286 A2 Aug. 25, 2022

Related U.S. Application Data

(63) Continuation of application No. 15/528,589, filed as application No. PCT/PT2015/050010 on Nov. 20, 2015, now Pat. No. 11,117,877.

(60) Provisional application No. 62/083,118, filed on Nov. 21, 2014.

(51) Int. Cl.
| | | |
|---|---|---|
| *C07D 277/36* | (2006.01) | |
| *C07D 277/34* | (2006.01) | |
| *A61K 9/00* | (2006.01) | |
| *A61K 31/426* | (2006.01) | |
| *A61K 45/06* | (2006.01) | |

(52) U.S. Cl.
CPC .......... *C07D 277/36* (2013.01); *A61K 9/0043* (2013.01); *A61K 31/426* (2013.01); *A61K 45/06* (2013.01); *C07D 277/34* (2013.01)

(58) Field of Classification Search
CPC ................ C07D 277/36; C07D 277/34; A61K 9/0043; A61K 31/426; A61K 45/06
USPC ........................................................ 514/1.1
See application file for complete search history.

(56) References Cited

U.S. PATENT DOCUMENTS

| | | | |
|---|---|---|---|
| 2,824,087 A | 2/1958 | Sagura et al. | |
| 5,284,656 A | 2/1994 | Platz et al. | |
| 5,451,569 A | 9/1995 | Wong et al. | |
| 5,747,517 A | 5/1998 | Panetta et al. | |
| 6,469,048 B2 | 10/2002 | Cohen et al. | |
| 7,868,033 B2 | 1/2011 | Labaudiniere et al. | |
| 10,377,729 B2 | 8/2019 | Vieira Simoes et al. | |
| 11,117,877 B2 | 9/2021 | Pontes Meireles Ferreira de Brito et al. | |
| 2002/0137762 A1 | 9/2002 | Joshi et al. | |
| 2005/0282818 A1 | 12/2005 | Ramesh et al. | |
| 2005/0288341 A1 | 12/2005 | Nag et al. | |
| 2006/0241186 A1 | 10/2006 | Stanton et al. | |
| 2010/0099683 A1 | 4/2010 | Tomkinson et al. | |
| 2018/0208570 A1 | 7/2018 | Vieira Simoes et al. | |
| 2019/0092737 A1 | 3/2019 | Pontes Meireles Ferreira de Brito et al. | |

FOREIGN PATENT DOCUMENTS

| | | |
|---|---|---|
| WO | WO 1994/029287 A1 | 12/1994 |
| WO | WO 2004/093803 A2 | 11/2004 |
| WO | WO 2004/093874 A1 | 11/2004 |
| WO | WO 2006/086517 A2 | 8/2006 |
| WO | WO 2008/124838 A1 | 10/2008 |
| WO | WO 2011/140333 A1 | 11/2011 |
| WO | WO 2013/170147 A1 | 11/2013 |
| WO | WO 2016/080853 A1 | 5/2016 |

OTHER PUBLICATIONS

International Search Report and Written Opinion for PCT/US2008/059931, dated Aug. 22, 2008.
International Search Report and Written Opinion for PCT/PT2015/050010 dated Mar. 30, 2016.
International Preliminary Report on Patentability for PCT/PT2015/050010 dated Jun. 1, 2017.
International Search Report and Written Opinion for PCT/IB2016/053546 dated Sep. 6, 2016.
International Preliminary Report on Patentability for PCT/IB2016/053546 dated Dec. 28, 2017.
Alegaon et al., Synthesis, characterization, and biological evaluation of thiazolidine-2,4-dione derivatives. Med Chem Res. 2014;23:987-994.
Alhamadsheh et al., Potent Kinetic Stabilizers That Prevent Transthyretin-Mediated Cardiomyocyte Proteotoxicity. Science Translational Medicine. Aug. 24, 2011;3(97):97ra81. DOI: 10.1126/scitranslmed.3002473.

(Continued)

*Primary Examiner* — Kristin A Vajda
(74) *Attorney, Agent, or Firm* — Wolf, Greenfield & Sacks, P.C.

(57) ABSTRACT

Compounds are provided for stabilizing protein transthyretin (TTR) and inhibiting amyloid fibril formation, for example, transthyretin-mediated amyloid fibril formation, and for treating, preventing, or ameliorating one or more symptoms of amyloid diseases, for example, transthyretin-related amyloidosis (ATTR).

20 Claims, 25 Drawing Sheets
Specification includes a Sequence Listing.

(56) References Cited

OTHER PUBLICATIONS

Almeida et al., Selective binding to transthyretin and tetramer stabilization in serum from patients with familial amyloidotic polyneuropathy by an iodinated diflunisal derivative. Biochemical Journal Jul. 2004;381(2):351-356. DOI: 10.1042/BJ20040011.
Alvarez-Diez et al., Mechanism-Based Inactivation of Cytochrome P450 3A4 by 4-Ipomeanol. Chem. Res. Toxicol., 2004;17(2):150-157. DOI: 10.1021/tx0341431.
Ando et al., Guideline of transthyretin-related hereditary amyloidosis for clinicians. Orphanet Journal of Rare Diseases 2013;8:31. https://doi.org/10.1186/1750-1172-8-31.
Beirao et al., Recurrence of Vitreous Amyloidosis and Need of Surgical Reintervention in Portuguese Patients With Familial Amyloidosis ATTR V30M. Retina 2011;31:1373-7. doi: 10.1097/IAE.0b013e318203c0c2.
Bhat et al., Synthesis and antihyperglycemic activity profiles of novel thiazolidinedione derivatives. Bioorg Med Chem. Nov. 15, 2004;12(22):5857-64.
Brain et al., Endothelin-1: demonstration of potent effects on the microcirculation of humans and other species. J Cardiovasc Pharmacol. 1989;13 Suppl 5:S147-9.
Braquet et al., Effect of endothelin-1 on blood pressure and bronchopulmonary system of the guinea pig. Journal of Cardiovascular Pharmacology Jan. 1989;13 Suppl 5:S143-6. Abstract only.
Brito et al., Amyloid Formation by Transthyretin: From Protein Stability to Protein Aggregation. 2003;3:349-360.
Bulawa et al., Tafamidis, a potent and selective transthyretin kinetic stabilizer that inhibits the amyloid cascade. PNAS Jun. 2012, 109 (24) 9629-9634. https://doi.org/10.1073/pnas.1121005109.
Cardoso et al., Comparative in vitro and ex vivo activities of selected inhibitors of transthyretin aggregation: relevance in drug design. Biochemical Journal Nov. 2007;408(1):131-138; DOI: 10.1042/BJ20070689.
Chemical Abstracts, STN Registry database, record for RN 1156379-50-8, "5-[[(2-furanylmethyl)thio]methyl]-2-methyl-3-furancarboxylic acid", entered into STN on Jun. 12, 2009. (Year: 2009).
Chemical Abstracts, STN Registry database, record for RN 303065-19-2, "5,5'-[thiobis(methylene)]bis[2-methyl-3-furancarboxylic acid]", entered into STN on Nov. 16, 2000. (Year: 2000).
Chemical Abstracts, STN Registry database, record for RN 325970-36-3, "5,5'-(1,2-ethenediyl)bis[2-methyl-N-(phenylmethyl)-3-furancarboxamide]", entered into STN on Mar. 7, 2001. (Year: 2001).
Choi et al., Accelerated Aβ Deposition in APPswe/PS1ΔE9 Mice with Hemizygous Deletions of TTR (Transthyretin). Journal of Neuroscience. Jun. 2007;27(26):7006-10. DOI: https://doi.org/10.1523/JNEUROSCI.1919-07.2007.
Coelho et al., Long-term effects of tafamidis for the treatment of transthyretin familial amyloid polyneuropathy. J Neurol. Nov. 2013;260(11):2802-14. doi: 10.1007/s00415-013-7051-7. Epub Aug. 22, 2013.
Coelho et al., Tafamidis for transthyretin familial amyloid polyneuropathy: a randomized, controlled trial. Neurology. Aug. 21, 2012;79(8):785-92. doi: 10.1212/WNL.0b013e3182661eb1. Epub Jul. 25, 2012.
Costa et al., Transthyretin binding to A-Beta peptide—Impact on A-Beta fibrillogenesis and toxicity. FEBS Letters, 2008;582(6):936-42. doi: 10.1016/j.febslet.2008.02.034.
Costa et al., Transthyretin Protects against A-Beta Peptide Toxicity by Proteolytic Cleavage of the Peptide: A Mechanism Sensitive to the Kunitz Protease Inhibitor. PLoS ONE 2008;3(8):e2899. https://doi.org/10.1371/journal.pone.0002899.
Faria et al., A look into amyloid formation by transthyretin: aggregation pathway and a novel kinetic model. Phys. Chem. Chem. Phys., 2015;17:7255-7263. DOI: 10.1039/C4CP04549A.
Ganguly et al., Molecular Docking studies of novel thiazolidinedione analogs as HIV-1-RT inhibitors. Med Chem Res. 2013; 22: 3350-63.

Hubbard et al., Anti-Neutrophil-Elastase Defenses of the Lower Respiratory Tract in α1-Antitrypsin Deficiency Directly Augmented with an Aerosol of α1-Antitrypsin. Ann Intern Med. 1989;111(3):206-212.
Johnson et al., Bisaryloxime ethers as potent inhibitors of transthyretin amyloid fibrilformation. J Med Chem. Mar. 10, 2005;48(5):1576-87.
Johnson et al., Toward Optimization of the Linker Substructure Common to Transthyretin Amyloidogenesis Inhibitors Using Biochemical and Structural Studies. J. Med. Chem., 2008;51(20):6348-6358. DOI: 10.1021/jm800435s.
Klabunde et al., Rational design of potent human transthyretin amyloid disease inhibitors. Nat Struct Biol. Apr. 2000;7(4):312-21.
Krasnaya et al., A novel method of the synthesis of substituted furans with the use of acetylenic alkoxy β-ketoesters. Tetrahedron 1967;23(9):3687-3697.
Lai et al., The Acid-Mediated Denaturation Pathway of Transthyretin Yields a Conformational Intermediate That Can Self-Assemble into Amyloid. Biochemistry, 1996;35(20):6470-6482. DOI: 10.1021/bi952501g.
Lawson et al., Tetrahydrothiophene. Organic Syntheses, 1956;36:89. http://www.orgsyn.org/Content/pdfs/procedures/CV4P0892.pdf.
Maccari et al., Evaluation of in vitro aldose redutase inhibitory activity of 5-arylidene-2,4-thiazolidinediones. Bioorg Med Chem Lett. Jul. 15, 2007;17(14):3886-93. Epub May 6, 2007.
Maia et al., Clinical phenotypes of Cerebral Amyloid Angiopathy. J Neurol Sci. Jun. 15, 2007;257(1-2):23-30. Epub Mar. 6, 2007.
Maia et al., CNS involvement in V30M transthyretin amyloidosis: clinical, neuropathological and biochemical findings. J Neurol Neurosurg Psychiatry. Feb. 2015;86(2):159-67. doi: 10.1136/jnnp-2014-308107. Epub Aug. 4, 2014.
McCurtry et al., Renal and hepatic necrosis after metabolic activation of 2-substituted furans and thiophenes, including furosemide and cephaloridine. Toxicol Appl Pharmacol. Nov. 1977;42(2):285-300.
Mitchell et al., Hepatic necrosis caused by furosemide. Nature. Oct. 1974;251:508-511. doi:10.1038/251508a0.
Naganawa et al., Synthetic studies on tautomycin. Tetrahedron, 1994;50:8969. DOI: 10.1016/S0040-4020(01)85365-5.
Nencetti et al., TTR Fibril Formation Inhibitors: Is there a SAR? Current Medicinal Chemistry, May 2012;19(15):2356-79. https://doi.org/10.2174/092986712800269326.
Ortore et al., Computational Studies on Transthyretin. Current Medicinal Chemistry, May 2012;19(15):2380-2387.
Palaninathan et al., Novel Transthyretin Amyloid Fibril Formation Inhibitors: Synthesis, Biological Evaluation, and X-Ray Structural Analysis. PLoS ONE 2009;4(7):e6290. https://doi.org/10.1371/journal.pone.0006290.
Parenti et al., Activity Predictions of Compunds in the Dyhydrofolate Reductase Dataset (MDDR). Supplementary Material. J Med Chem. 2004; 1-45.
Parenti et al., Three-dimensional quantitative structure-activity relationship analysis of a set of Plasmodium falciparum dihydrofolate reductase inhibitors using a pharmacophore generation approach. J Med Chem. Aug. 12, 2004;47(17):4258-67. doi: 10.1021/jm040769c.
Penchala et al., AG10 inhibits amyloidogenesis and cellular toxicity of the familial amyloid cardiomyopathy-associated V122I transthyretin. PNAS Jun. 2013;110(24):9992-9997. https://doi.org/10.1073/pnas.1300761110.
Peterson et al., A Reactive Metabolite of Furan, cis-2-Butene-1,4-dial, Is Mutagenic in the Ames Assay. Chem Res Toxicol. 2000;13(7):531-534. DOI: 10.1021/tx000065f.
Petrassi et al., Structure-Based Design of N-Phenyl Phenoxazine Transthyretin Amyloid Fibril Inhibitors. J. Am. Chem. Soc., 2000;122(10):2178-92. DOI: 10.1021/ja993309v.
Petrassi et al., The copper-mediated cross-coupling of phenylboronic acids and N-hydroxyphthalimide at room temperature: synthesis of aryloxy amines. Org Lett. Jan. 11, 2001;3(1):139-42.
Pevzner et al., Synthesis and Phosphorylation of 4-Functionalized 2-tert-Butyl-3-chloromethylfurans. Russian Journal of General Chemistry, Jul. 2002;72(7):1085-1089.

(56) References Cited

OTHER PUBLICATIONS

Purkey et al., Hydroxylated polychlorinated biphenyls selectively bind transthyretin in blood and inhibit amyloidogenesis: rationalizing rodent PCB toxicity. Chem Biol. Dec. 2004;11(12):1719-28.
Raz et al., The Interaction of Thyroxine with Human Plasma Prealhumin and with the Prealhumin-Retinol-hinding Protein Complex. The Journal of Biological Chemistry 1969;244(12):3230-3237.
Ribeiro et al., Stability of the Transthyretin Molecule as a Key Factor in the Interaction with A-Beta Peptide—Relevance in Alzheimer's Disease. PLoS ONE 2012;7(9): e45368. https://doi.org/10.1371/journal.pone.0045368.
Ribeiro et al., Transthyretin stabilization by iododiflunisal promotes amyloid-β peptide clearance, decreases its deposition, and ameliorates cognitive deficits in an Alzheimer's disease mouse model. J Alzheimers Dis. 2014;39(2):357-70. doi: 10.3233/JAD-131355.
Robertson et al., The Rhodadyns, a New Class of Small Molecule Inhibitors of Dynamin GTPase Activity. ACS Med Chem Lett. Mar. 26, 2012;3(5):352-6. doi: 10.1021/m1200284s. eCollection May 10, 2012.
Scott et al., Tafamidis: a review of its use in familial amyloid polyneuropathy. Drugs. Aug. 2014;74(12):1371-8. doi: 10.1007/s40265-014-0260-2.
Seidler et al., Identification and prediction of promiscuous aggregating inhibitors among known drugs. J Med Chem. Oct. 9, 2003;46(21):4477-86.
Sekijima, Recent progress in the understanding and treatment of transthyretin amyloidosis. J Clin Pharm Ther. Jun. 2014;39(3):225-33. doi: 10.1111/jcpt.12145.
Shen et al., Rhodium(III)-catalyzed C—H olefination for the synthesis of ortho-alkenyl phenols using an oxidizing directing group. Org Lett. Jul. 5, 2013;15(13):3366-9. doi: 10.1021/o14014188. Epub Jun. 20, 2013.
Simoes et al., A novel bis-furan scaffold for transthyretin stabilization and amyloid inhibition. Eur J Med Chem. Oct. 4, 2016;121:823-840. doi:10.1016/j.ejmech.2016.02.074. Epub Mar. 3, 2016.
Simoes et al., Toward the Discovery of Functional Transthyretin Amyloid Inhibitors: Application of Virtual Screening Methods. J. Chem. Inf. Model., 2010;50(10):1806-1820. DOI: 10.1021/ci100250z.
Stahla-Beek et al., Identification of a novel antiviral inhibitor of the flavivirus guanylyltransferase enzyme. J Virol. Aug. 2012;86(16):8730-9. doi: 10.1128/JVI.00384-12. Epub Jun. 6, 2012.
Whitney et al., Benzyne-oxazole cycloadducts: isolation and retro-Diels-Alder reactions. J. Org. Chem., 1990;55(3):929-935. DOI: 10.1021/jo00290a025.
Winberg et al., Dimethylenedihydroheteroaromatic Compounds and Heterocyclophanes by 1,6-Hofmann Elimination Reactions. J. Am. Chem. Soc., 1960;82(6):1428-1435. DOI: 10.1021/ja01491a037.
PCT/US2008/05993, Aug. 22, 2008, International Search Report and Written Opinion.
PCT/PT2015/050010, Mar. 30, 2016, International Search Report and Written Opinion.
PCT/PT2015/050010, Jun. 1, 2017, International Preliminary Report on Patentability.
PCT/IB2016/053546, Sep. 6, 2016, International Search Report and Written Opinion.
PCT/IB2016/053546, Dec. 28, 2017, International Preliminary Report on Patentability.

Scheme 1, where X=F or Cl.

Scheme 2

Scheme 3, where X=Cl or CH3.

Thyroxine (T4)    2OH-PCB80    Phenox    PCX2

ZINC04638817

ZINC02504634

ZINC01429477

ZINC01753456

ZINC01691128

ZINC04713400

ZINC06726214

ZINC05041243

ZINC06170657

ZINC03873083

Benoxaprofen　　　　　　　Tafamidis　　　　　　　ZINC00310685

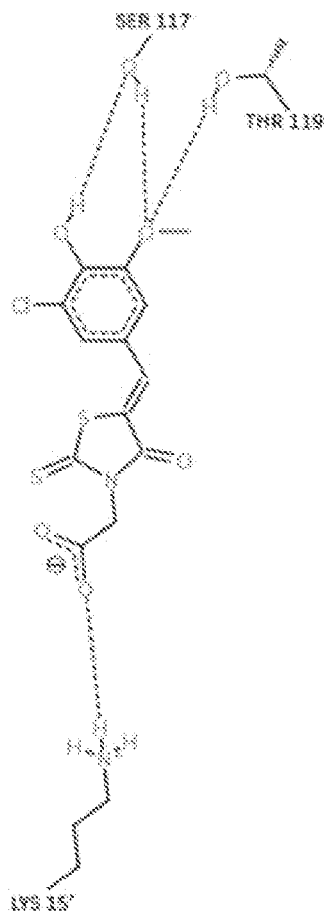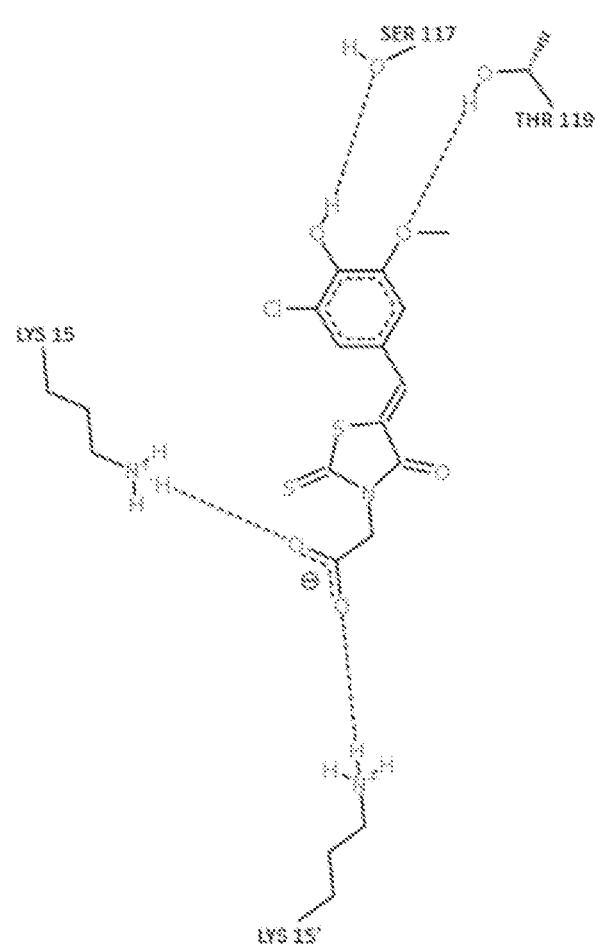
FIG. 15C                    FIG. 15D

2-THIOXOTHIAZOLIDIN-4-ONE DERIVATIVES ACTIVE AS TRANSTHYRETIN LIGANDS AND USES THEREOF

RELATED APPLICATIONS

This application is a continuation of and claims under 35 U.S.C. § 120 to U.S. patent application U.S. Ser. No. 15/528,589, filed May 22, 2017, which is a national stage filing under 35 U.S.C. § 371 of international PCT Application, PCT/PT2015/050010, filed Nov. 20, 2015, which claims priority under 35 U.S.C. § 119(e) to U.S. Provisional Application, U.S. Ser. No. 62/083,118, filed Nov. 21, 2014, each of which is incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Oct. 26, 2021, is named B139970000US03-SEQ-WWZ and is 3,086 bytes in size.

BACKGROUND OF THE INVENTION

Transthyretin (TTR) is a homotetramer protein found in the blood plasma, the cerebral spinal fluid and the eye's retina. TTR is implicated in the formation of amyloid aggregates and deposition of amyloid fibrils, causing several pathologies in humans. The wild-type form of TTR is involved in senile systemic amyloidosis (SSA) in elders, due to deposition of amyloid mostly in the heart tissue. More than a hundred TTR variants are associated with amyloid formation and deposition of amyloid fibrils in various tissues and therefore with several familial amyloidoses, including familial amyloid polyneuropathy (FAP) and familial amyloid cardiomyopathy (FAC). In all cases, TTR aggregation seems to cause neuronal and/or cellular dysfunction by mechanisms that are not yet fully elucidated.

TTR plays a critical role in modulating the deposition of beta amyloid (Abeta) in Alzheimer's Disease. In addition, TTR stability is a key factor in TTR-Abeta interactions, which is relevant for pathogenesis of Alzheimer's Disease. It has also been shown that administration of the TTR stabilizer iododiflunisal (IDIF) to AD/TTR$^{+/-}$ mice resulted in decreased brain Abeta levels and deposition and in improved cognitive function associated with reduced AD-like neuropathology in that particular mouse model. See, e.g., Choi et al. *J Neurosci.* 2007 Jun. 27; 27(26):7006-10; Ribeiro et al. PLoS One. 2012; 7(9):e45368; and Ribeiro et al. J Alzheimer's Dis. 2014; 39(2):357-70; the entire contents of each of which are incorporated herein by reference.

Amyloid formation by TTR involves a first step wherein the native TTR tetramer dissociates to monomers with low conformational stability and increased tendency for partial unfolding [1]. This is followed by self-assembly of partially unfolded monomers to form cytotoxic, oligomeric intermediate species, and eventually amyloid fibrils. Thus, stabilization of the native tetrameric form of TTR is a valid approach to reduce amyloid formation and can be attained by the binding of small organic molecules to tetrameric TTR.

It has been shown that thyroxine (T4) and several non-steroidal anti-inflammatory drugs (NSAIDs) bind to one or the two equivalent, funnel-shaped thyroxine-binding sites in TTR with high affinity, stabilize the tetramer and thereby prevent in vitro amyloid fibril formation [2]. However, the use of NSAIDs in long-term treatments of TTR-amyloidoses is hindered by their poor selectivity for TTR and adverse anti-inflammatory effects. In addition, compared to the concentration of TTR in the human plasma (3.6-7.2 micromolar), the concentration of T4 is low (0.1 micromolar). Moreover, thyroid-binding globulin (TBG) has an order of magnitude higher affinity for T4. As such, less than 1% of TTR circulating in the plasma is complexed with T4.

The identification of novel, selective and safe TTR stabilizers capable of inhibiting amyloid formation is highly desirable. This has been illustrated by the development of tafamidis meglumine, chemical name N-methyl D-(2,3,4,5,6-pentahydroxy-hexyl)-ammonium; 2-(3,5-dichloro-phenyl)-benzoxazole-6-carboxylate, the first and only chemical entity directed to the treatment of FAP to have reached the drug market [3]. Tafamidis meglumine demonstrated improvement of symptoms (mostly in secondary endpoints) in approximately 60% of FAP patients enrolled in an 18-month phase-III clinical trial [4].

SUMMARY OF THE INVENTION

The present application provides compounds, compositions, and pharmaceutical preparations useful for stabilizing the native state of TTR and inhibiting the formation of TTR amyloid fibrils. Methods for preparing such compounds, compositions, and pharmaceutical preparations are also provided. In addition, methods for using such compounds, compositions, and pharmaceutical preparations for inhibiting the formation of TTR amyloid fibrils, for example in the context of treating amyloid diseases, are also provided.

Some aspects of this disclosure provide N-substituted arylidenerhodanine and arylidenethiazolidinedione compounds that are useful for inhibiting TTR amyloid fibril formation in vitro or in vivo, and thus can be used to treat amyloid diseases, e.g., amyloid diseases associated with transthyretin-related amyloidosis (ATTR). The compounds provided herein stabilize the tetrameric native state of the protein transthyretin (TTR), preventing amyloid fibril formation commonly observed when TTR is destabilized into monomers, and therefore may be used for treating amyloid diseases associated with TTR destabilization.

Some aspects of this disclosure provide compounds of Formula (I):

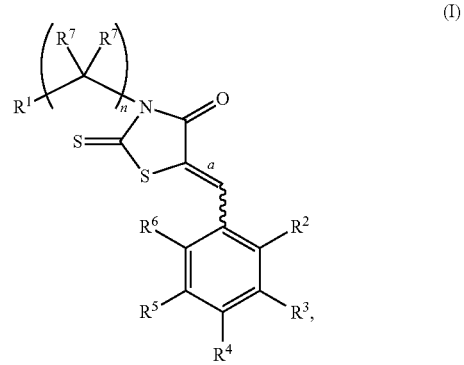

as well as pharmaceutically acceptable salts, solvates, hydrates, tautomers, stereoisomers, or prodrugs thereof, wherein:

the double bond labeled with "a" is of (E)- or (Z)-configuration;

$R^1$ is —C(=O)OR$^a$, —S(=O)$_2$NHR$^a$, —S(=O)$_2$OR$^a$, —P(=O)NH$_2$(OR$^a$), —C(=O)N(R$^a$)$_2$, —C(=O)NHOR$^a$,

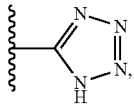

or —OR$^a$;

$R^2$ is H or Halogen;

$R^3$ is H, —OH, Halogen, —CH$_3$, or —OCH$_3$;

$R^4$ is H, —OR$^a$, F, —OCH$_3$, —NH$_2$, —ONH$_2$, —NCH$_2$, —CN, or —SH;

$R^5$ is H, —OH, Halogen, —CH$_3$, or —OCH$_3$;

$R^6$ is H or Halogen;

each instance of $R^7$ is independently H, substituted or unsubstituted C$_{1-6}$ alkyl, —C(=O)OR$^a$, or —C(=O)N(R$^a$)$_2$;

each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring, or a chemical delivery system (CDS); and n is 1, 2, or 3.

Some aspects of this disclosure provide compounds of Formula (II):

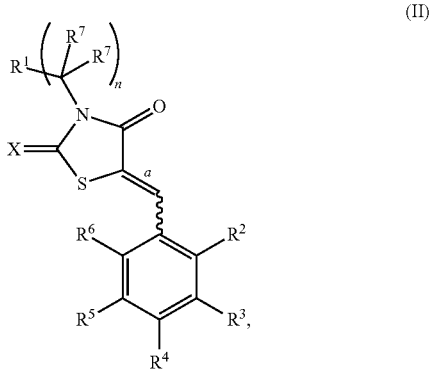

as well as pharmaceutically acceptable salts, solvates, hydrates, tautomers, stereoisomers, or prodrugs thereof, wherein:

the double bond labeled with "a" is of (E)- or (Z)-configuration;

$R^1$ is —C(=O)OR$^a$, —S(=O)$_2$NHR$^a$, —S(=O)$_2$OR$^a$, —P(=O)NH$_2$(OR$^a$), —C(=O)N(R$^a$)$_2$, —C(=O)NHOR$^a$, —CHN$_4$ (tetrazolyl), or —OR$^a$;

$R^2$ is H or Halogen;

$R^3$ is H, —OH, Halogen, —CH$_3$, or —OCH$_3$;

$R^4$ is H, —OR$^a$, F, —OCH$_3$, —NH$_2$, —ONH$_2$, —NCH$_2$, —CN, or —SH;

$R^5$ is H, —OH, Halogen, —CH$_3$, or —OCH$_3$;

$R^6$ is H or Halogen;

each instance of $R^7$ is independently H, substituted or unsubstituted C$_{1-6}$ alkyl, —C(=O)OR$^a$, or —C(=O)N(R$^a$)$_2$;

each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring;

n is 1, 2, or 3; and

X is O or S.

Some aspects of this disclosure provide pharmaceutical preparations comprising a compound as described herein, or a pharmaceutically acceptable salt, solvate, hydrate, tautomer, stereoisomer, or prodrug thereof, and a pharmaceutically acceptable carrier. Typically, the pharmaceutical preparations provided herein are suitable for administration to a human subject, e.g., in that they are sterile and essentially pyrogen-free. In some embodiments, the pharmaceutical preparation comprises the compound, or the pharmaceutically acceptable salt, solvate, hydrate, tautomer, stereoisomer, or prodrug thereof in an amount effective to inhibit amyloid fibril formation, to stabilize TTR, and/or to ameliorate at least one symptom of an amyloid disease in the subject.

Some aspects of this disclosure provide methods for inhibiting amyloid fibril formation in a subject. The methods typically comprise administering a compound described herein, or a pharmaceutically acceptable salt, solvate, hydrate, tautomer, stereoisomer, or prodrug thereof, or a pharmaceutical preparation as described herein to a subject in need thereof. Some aspects of this disclosure provide methods of treating an amyloid disease by administering a compound described herein, or a pharmaceutically acceptable salt, solvate, hydrate, tautomer, stereoisomer, or prodrug thereof, or a pharmaceutical preparation described herein to a subject in need thereof. Exemplary amyloid diseases that can be treated with the methods provided herein include, but are not limited to, Familial Amyloid Polyneuropathy, Familial Amyloid Cardiomyopathy, Senile Systemic Amyloidosis, AA amyloidosis, Alzheimer's Disease, Light-Chain (AL) amyloidosis, Type-2 Diabetes, Medullary Carcinoma of the Thyroid, Parkinson's disease, Polyneuropathy, and Spongiform Encephalopathy (Creutzfeldt Jakob disease).

In some aspects, this disclosure provides methods for preparing the compounds and preparations described herein.

The details of one or more embodiments of the disclosure are set forth in the accompanying Figures and the Detailed Description. Other features, objects, and advantages of the disclosure will be apparent from the description and from the claims.

DEFINITIONS

Definitions of specific functional groups and chemical terms are described in more detail below. The chemical elements are identified in accordance with the Periodic Table of the Elements, CAS version, *Handbook of Chemistry and*

Physics, 75*th* Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5*th* Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3*rd* Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like.

Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

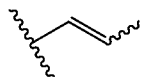

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, which are divalent bridging groups, are further referred to using the suffix-ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{aa}$, —ON(R$^{ff}$)$_2$, —N(R$^{ff}$)$_2$, —N(R$^{ff}$)$_3^+$X$^-$, —N(OR$^{cc}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl), —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl), —OP(=O)(C$_{1-6}$ alkyl), —OP(=O)(OC$_{1-6}$ alkyl), $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, $—R^{aa}$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

An "ester" of a compound of the present disclosure refers to that compound wherein one or more of the acidic hydrogens of the carboxylic acid ($—CO_2H$) groups provided in the molecule are replaced with a non-hydrogen group (e.g., an alkyl group).

An "amide" of a compound of the present disclosure refers to that compound wherein one or more of the —OH groups of the carboxylic acid ($—CO_2H$) provided in the molecule are replaced with a substituted or unsubstituted amino group.

The invention is not intended to be limited in any manner by the above exemplary listing of substituents.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound, of the present disclosure non-covalently associated with one or more molecules of water. Likewise, a "solvate" refers to a compound of the present disclosure non-covalently associated with one or more molecules of an organic solvent.

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrug," as used herein, refers to compounds that have cleavable groups and become by solvolysis or under physiological conditions the compounds described herein, which are pharmaceutically active in vitro or in vivo. Exemplary prodrugs include esters and/or amides of a compound of Formula (I) or Formula (II) that can react under biological conditions (e.g., in vitro or in vivo enzymatic conditions) to provide the parent carboxylic acid compound. In certain embodiments, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may have enhanced stability for long-term storage. See, e.g., Bundgard, H., *Design of Prodrugs*, pp. 7-9, 21-24, Elsevier, Amsterdam 1985, the entire contents of which are incorporated herein by reference.

The term "pharmaceutically acceptable carrier," as used herein, refers to one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical preparations also are capable of being commingled with the compounds of the present invention, and with each other, in a manner such that there is no interaction which would substantially impair the desired pharmaceutical efficacy.

The term "pharmaceutically acceptable salt," as used herein, refers to an acid or base form of a compound, usually in combination with a counter ion, that is suitable for use in pharmacy. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Pharmaceutically acceptable salts are well known in the art and are the subject of numerous reviews and monographs such as P. H. Stahl and C. G. Wermuth, editors, *Handbook of Pharmaceutical Salts: Properties, Selection and Use*, Weinheim/Ziirich:Wiley-VCH/VHCA, 2002.

The terms "therapy," "therapeutic," "treat," or "treatment" refer to, but are not limited to, one or more clinical intervention with an intent to prevent, ameliorate, or cure a condition or symptoms of the condition in a subject.

BRIEF DESCRIPTION OF THE DRAWINGS

FIGS. 15A to 15D. Predicted docking poses for the E and the Z stereoisomeric forms of the original virtual screening hit AT50-A00 (grey stick representation). In the top panels, TTR's thyroxine binding site is represented by the side-chains of residues (darker sticks) that are known to interact with TTR stabilizers: top view (FIG. 15A) and side view (FIG. 15B) of the binding site holding both docked stereoisomers. In the bottom panels, TTR:compound interactions are represented in 2D diagrams for both the E stereoisomer (FIG. 15C) and for the Z stereoisomer (FIG. 15D).

DETAILED DESCRIPTION OF THE INVENTION

Introduction

Figure 1:
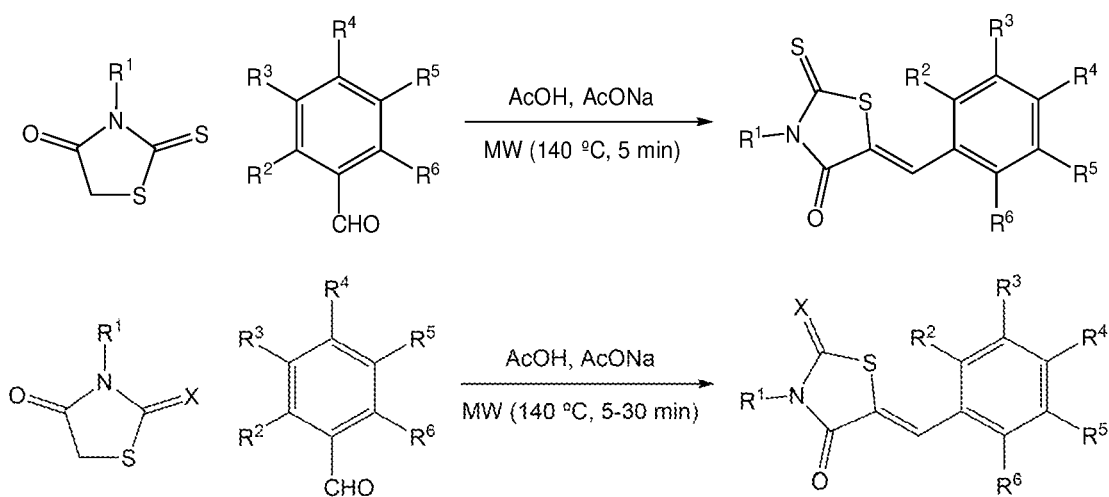
FIG. 1. General synthetic route for preparation of the N-substituted arylidenerhodanines and arylidenethiazolidinediones (AT50 lead series), where $R^1$ is a hydroxycarbonyl or dihydroxycarbonyl alkyl group including, but not limited to $CH_2CO_2H$, $CH(CH_3)CO_2H$, $CH(CO_2H)(CH_2)_2CO_2H$, $(CH_2)_3CO_2H$ or $(CH_2)_2CO_2H$; $R^2$ and $R^6$ are independently selected from H or Cl; $R^3$ and $R^5$ are independently selected from H, OH, F, Cl, Br, I, $CH_3$ or $OCH_3$; $R^4$ is H or OH, X is S or O.

Provided herein are compounds that bind to and stabilize the native state of the protein transthyretin (TTR), thereby stabilizing TTR, inhibiting TTR aggregation, and reducing amyloid fibril formation. Through inhibition of TTR aggregation, one can intervene in or treat TTR-related diseases, ameliorate symptoms, and/or in some cases prevent or treat amyloid diseases associated with TTR amyloid fibril formation. The compounds described herein are useful for the stabilization of TTR and thus for the treatment, prevention, or amelioration of one or more symptoms of amyloid diseases that are associated with TTR amyloid fribril formation, such as, for example, Familial Amyloidotic Polyneuropathy (FAP), Familial Amyloidotic Cardiomyopathy (FAC), Senile Systemic Amyloidosis (SSA), AA amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

Without wishing to be bound by theory, it is believed that TTR dysfunction, for example based on a mutation of the TTR gene, is associated with such amyloid diseases. More than 130 mutations in the TTR gene have been reported, over 100 of which are believed to be associated with amyloid disease or amyloidogenic. Wild-type (WT) form of TTR and its fragments can also form amyloid fibrils, and such wild-type TTR fibrils are commonly seen in SSA, a typically relatively mild disorder that affects approximately 25% of individuals over 80 years of age. In other amyloid diseases, however, amyloid fibrils are mostly constituted by mutant variants of TTR, e.g., in FAP and FAC. FAP is an autosomal dominant lethal disease, characterized by peripheral neuropathy, which may affect individuals from their twenties. FAP typically leads to death within 10-15 years upon diagnosis.

The liver is the main site of production of amyloidogenic TTR circulating in the plasma. One option for treating amyloid disease in TTR mutant individuals is thus liver transplantation (LT), which may halt progression of clinical symptoms of amyloid diseases by replacing the disease-associated TTR allele with a wild-type allele. Such treatment has been successfully employed in the treatment of FAP cases. However, transplantation is problematic due to its invasive nature, scarcity of donors, the required long-term post-transplantation immunosuppressive therapy, the high costs involved, and the large number of patients that are not eligible because of their disease progression. Furthermore, LT does not eschew the synthesis of mutant TTR by the choroid plexus and subsequent deposition in the central nervous system (CNS) synthesis. Transplantation is also not a viable option for all TTR amyloid diseases, including the most prevalent TTR diseases, namely SSA and FAC.

Tafamidis meglumine reached the drug market in November 2011 as the first drug therapy directed to FAP. Tafamidis is a potent stabilizer of tetrameric TTR that has been developed using structure-based design methods. After demonstrating improvement of symptoms in approximately 60% of FAP patients enrolled in an 18-month phase-III clinical trial, tafamidis has been approved in Europe by the European Medicines Agency (November 2011) and in Japan by the Pharmaceuticals and Medical Devices Agency (September 2013) for treatment of adult FAP patients showing early symptoms of polyneuropathy. Patients treated with tafamidis in clinical trials showed some preservation of function and had less neurological deterioration. The reduced rate of neurologic deterioration was sustained throughout a 12-month extension study (totaling 30 months of treatment). Even though tafamidis was relatively well tolerated over the total period of 30 months, evidence supporting disease reversion is still missing. Moreover, there is still little or no evidence on tafamidis' ability to treat disease forms other than FAP in subjects having a TTR Val30Met mutation.

Some aspects of the present disclosure are based on the discovery of compounds that bind to the tetrameric protein transthyretin (TTR), stabilize the TTR tetramer and thereby reduce the formation of TTR amyloid aggregates and fibrils. Prioritization of compounds from various chemical classes for biochemical evaluation against amyloid fibril formation was achieved by exploring several ligand-based virtual screening approaches, some aspects of which have been described in reference [20]. Examples of the discovered new inhibitors of amyloid fibril formation are provided in this section.

TTR and TTR-Related Amyloidoses

Amyloidosis is a protein conformational disorder characterized by accumulation of extracellular aggregates and fibrils derived from several distinct proteins [5,6]. At least thirty protein precursors of amyloid fibrils have been recognized as causative agents of diverse types of amyloidosis [7,8]. Depending on the type of amyloidosis, various features may be responsible for protein aggregation.

Transthyretin (TTR) is an important amyloidogenic protein, synthesized mainly in the liver but also in the choroid plexuses of the brain, retinal pigment epithelial cells of the eye, and a-cells of pancreatic islets [9-13]. Even though its function is poorly understood, TTR is known to form a homotetramer in the bloodstream and to act as a transport protein for thyroid hormone and retinol-binding protein with vitamin A. Currently, more than 130 mutations in the TTR gene have been reported, even though 15 are nonamyloidogenic [14,15]. TTR is associated with at least three kinds of amyloidotic pathologies: familial amyloidotic polyneuropathy (FAP), familial amyloid cardiomyopathy (FAC) and senile systemic amyloidosis (SSA). FAP is a hereditary systemic amyloidosis induced by mutant forms of the protein [16]. Corino de Andrade first described the disease in 1952 [17] in the Portuguese population, mainly from the northern part of the country. The age of onset of the disease is usually between 20 and 35 years of age, characterized by systemic deposition of amyloid and with a special involvement of the peripheral nerves. Progression to death is fast, usually within 10 to 15 years. FAC does not result from loss of TTR function (due to aggregation); it seems to be caused by tissue-selective deposition of mutant TTR in the heart [15,18]. The V122I-TTR variant is the most common amyloidogenic mutation worldwide. It is responsible for the onset of FAC, predominantly in individuals of African descent. It is estimated that approximately 4% of African Americans (1.3 million people) are heterozygous for the V122I allele [15]. FAC patients are prone to suffer cardiac failure (especially V122I homozygotes) [15,19]. The third type is senile systemic amyloidosis (SSA), which is an aging-related systemic amyloidosis, resulting from aggregation of wild-type (WT) TTR and deposition of fibrils mainly in the heart. The age of onset of SSA is similar to that of FAC—typically after 60 years of age.

Two exemplary, non-limiting TTR protein sequences are provided below. Those of skill in the art will be able to ascertain additional wild-type and mutant TTR sequences based on this disclosure and the knowledge in the art:

```
>gi|4507725|ref|NP_000362.1| transthyretin
precursor [Homo sapiens]
                                       (SEQ ID NO: 1)
MASHRLLLLCLAGLVFVSEAGPTGTGESKCPLMVKVLDAVRGSPAINVA
VHVFRKAADDTWEPFASGKTSESGELHGLTTEEEFVEGIYKVEIDTKSY
WKALGISPFHEHAEVVFTANDSGPRRYTIAALLSPYSYSTTAVVTNPKE >gi|48145933|emb|CAG33189.1| TTR [Homo sapiens]
                                       (SEQ ID NO: 2)
MASHRLLLLCLAGLVFVSEAGPTGTGESKCPLMVKVLDAVRGSPAINVA
VHVFRKAADDTWEPFASGKTSESGELHGLTTEEEFVEGIYKVEIDTKSY
WKALGISPFHEHAEVVFTANDSGPRRYTIAALLSPYSYSTTAVVTNPKD
```

TTR and TTR Stability in Alzheimer's Disease

Alzheimer's disease (AD) is associated with progressive memory loss and severe cognitive decline. These clinical features are associated with deposition of 40-42 amino acid β-amyloid (Aβ) peptides in the cerebral cortex and hippocampal formation. Several biochemical and in vivo studies have revealed that transthyretin (TTR) may play a role in modulating Aβ aggregation both in vitro and in vivo. TTR forms stable complexes with Aβ in vitro and prevents aggregation/amyloid formation (See, e.g., Schwarzman et al., Transthyretin sequesters amyloid beta protein and prevents amyloid formation. Proc. Natl. Acad. Sci. USA. 91(18), 8368-72 (1994)). Microarray studies of hippocampi from 6-month-old Tg2576 transgenic mice, or cortical tissue from Tg2576/PS1$^{P264I/P264L}$ mice analyzed well before the onset of Aβ deposition, have revealed markedly elevated levels of TTR transcripts (See, e.g., Stein et al. Lack of Neurodegeneration in Transgenic Mice Overexpressing Mutant Amyloid Precursor Protein Is Associated with Increased Levels of Transthyretin and the Activation of Cell Survival Pathways. J. Neurosci. 22(17), 7380-7388 (2002); and Wu et al., Comparative analysis of cortical gene expression in mouse models of Alzheimer's disease. Neurobiol. Aging. 27(3), 377-386 (2006)). These studies suggested that 11R gene expression was induced in response to overproduction of Aβ peptides and that overexpressed TTR would sequester Aβ species and thus preclude their subsequent aggregation and deposition. Choi et al. crossed mice that harbor FAD-linked APPswe and PS1ΔE9 transgenes to mice with homozygous deletions of TTR. Brain Aβ levels and amyloid deposition in ceAPPswe/PS1ΔE9/TTR+/+ or ceAPPswe/PS1ΔE9/TTR+/− mice were examined as a function of age. They reported that amyloid deposition is accelerated and Aβ levels are significantly elevated in the brains of ceAPPswe/PS1ΔE9/TTR+/− compared with ceAPPswe/PS1ΔE9/TTR+/+ mice at all ages examined, suggesting that TTR plays a critical role in modulating Aβ deposition in vivo (See, e.g., Choi et al., Accelerated Abeta deposition in APPswe/PS1deltaE9 mice with hemizygous deletions of TTR (transthyretin). J. Neurosci. 27(26), 7006-10 (2007)).

TTR-Aβ interactions were further characterized by Costa et al., who showed that TTR is capable of interfering with Aβ fibrilization by both inhibiting and disrupting fibril formation (See, e.g., Costa et al., Transthyretin binding to A-Beta peptide—impact on A-Beta fibrillogenesis and toxicity. FEBS Lett. 582(6), 936-42 (2008)). They also proposed that TTR, either recombinant or isolated from human sera, can proteolytically process Aβ, generating smaller and less amyloidogenic new peptides and enabling cells to eradicate them (See, e.g., Costa et al., Transthyretin protects against A-beta peptide toxicity by proteolytic cleavage of the peptide: a mechanism sensitive to the Kunitz protease inhibitor. PLoS One. 3(8), e2899 (2008)). More recently, Ribeiro et al. were able to reveal discrepancies in the interaction of different TTR variants with Aβ, prompting TTR stability as a key factor in TTR-Aβ interactions—which may be important in the pathogenesis of AD (See, e.g., Ribeiro et al., Stability of the transthyretin molecule as a key factor in the interaction with a-beta peptide—relevance in Alzheimer's disease. PLoS One. 7(9), e45368 (2012)). They went on to show that administration of IDIF (a known TTR stabilizer used as reference in this work; see FIG. 23) in AD/TTR+/− mice resulted not only in decreased brain Aβ levels and deposition but also in improved cognitive function associated with AD-like neuropathology in that particular mice model (See, e.g., Ribeiro et al., Transthyretin stabilization by iododiflunisal promotes amyloid-β peptide clearance, decreases its deposition, and ameliorates cognitive deficits in an Alzheimer's disease mouse model. J. Alzheimer's. Dis. 39(2), 357-70 (2014), the entire contents of which are incorporated herein by reference).

Some aspects of this disclosure are based on the recognition that one or several compounds disclosed herein are useful in the treatment of AD, as they all show stronger TTR stabilization activity than IDIF. Treatment of AD would be enhanced by the compounds efficiently reaching TTR in the brain, namely in the cerebrospinal fluid. Some of the compounds disclosed herein are inherently capable of crossing the blood-brain barrier (BBB). In order to further enhance the delivery of such compounds to the brain or in order to deliver compounds that do not cross the BBB with sufficient efficiency, the compounds provided herein may also be conjugated to a chemical delivery system (CDS), such as the 1,4-dihydroquinoline moiety in order to increase BBB permeation (See, e.g., Bodor et al., Barriers to remember: brain-targeting chemical delivery systems and Alzheimer's disease. Drug Discov. Today. 7(14), 766-774 (2002); Foucout et al., Synthesis, radiosynthesis and biological evaluation of 1,4-dihydroquinoline derivatives as new carriers for specific brain delivery. Org. Biomol. Chem. 7(18), 3666-73 (2009); and Gourand et al., Chemical delivery system of metaiodobenzylguanidine (MIBG) to the central nervous system. J. Med. Chem. 53(3), 1281-7 (2010)). All references are incorporated herein in their entirety by reference.

TTR and TTR-RBP4 Interactions in Age-Related Macular Degeneration, Stargardt Disease and Related Oculopathies Some aspects of this disclosure are based on the recognition that the compounds disclosed herein are useful in the treatment of Macular Degeneration and Stargardt's disease.

Age-related Macular Degeneration (AMD) is the leading cause of blindness in developed countries, affecting 62.9 million individuals worldwide; Stargardt Disease (STGD) is a rare genetic disease responsible for vision loss in young adults.

The rates of the visual cycle and N-retinylidene-N-retinylethanolamine (A2E) production in the retina depend on the influx of all-trans-retinol from serum to the retinal pigment epithelium (RPE). It has been suggested that pharmacologic downregulation of serum retinol may represent a treatment strategy for atrophic AMD (Radu et al., Investig. Opthalmology Vis. Sci. 46 (2005), referenced below), and other disorders characterized by excessive accumulation of lipofuscin, like STGD.

Fenretinide, for example, is known to bind with serum retinol binding protein (RBP) and displace all-trans-retinol from RBP (Berni et al., FEBS Lett. 308 (1992) 43-45, referenced below). This results in a loss of complexation of RBP with transthyretin (TTR) and rapid renal clearance of RBP. The formation of the RBP-TTR-retinol complex is critical for all-trans-retinol transport from serum to the RPE. Therefore, fenretinide treatment leads to reduction in ocular all-trans-retinol uptake and inhibition of the visual cycle (Radu et al). Fenretinide was shown to effectively block the A2E production in the Abca4−/− model of excessive lipofuscin accumulation (Radu et al).

Fenretinide is not ideal for use in the treatment of AMD and STGD due to its off-target pro-apoptotic activity and teratogenicity. On the other hand, prolonged treatments with RBP4 antagonists in elders or sub-populations of patients with pro-amyloidogenic mutations in the TTR gene may be limited, since the formation of the tertiary retinol-RBP4-TTR complex stabilizes TTR tetramers and prevents formation of TTR amyloid fibrils (White et al., Proc. Natl. Acad. Sci. USA. 98 (2001) 13019-13024, and Hyung et al., ACS Chem. Biol. 5 (2010) 1137-1146, referenced below).

Stabilizers of the native state of TTR may also modulate or inhibit interactions between TTR and Retinol Binding Protein 4 (RBP4) in serum, either directly at the TTR-RBP4 interaction site or allosterically. TTR-RBP4 interactions have been suggested to be of interest in diseases such as Age-related Macular Degeneration (AMD) and Stargardt disease (STGD) (Buxbaum et al., Cell. Mol. Life Sci. 66 (2009) 3095-3101, and Petrukhin, Expert Opin. Ther. Targets. 11 (2007) 625-39, referenced below. As reported by Petrukhin et al., U.S. application Ser. No. 14/530,516, Published as US20150057320 A1, the entire contents of which are incorporated herein by reference), some TTR ligands that allosterically antagonize retinol-dependent RBP4-TTR interactions induce the disruption of the retinol-RBP4-TTR complex with subsequent reduction in serum RBP4 and retinol levels. This may lead to the reduced uptake of retinol to the retina, inhibition of the visual cycle and reduction in formation of cytotoxic A2E.

References cited in this section

R. A. Radu, Y. Han, T. V. Bui, S. Nusinowitz, D. Bok, J. Lichter, et al., Reductions in Serum Vitamin A Arrest Accumulation of Toxic Retinal Fluorophores: A Potential Therapy for Treatment of Lipofuscin-Based Retinal Diseases, Investig. Opthalmology Vis. Sci. 46 (2005) 4393. doi:10.1167/iovs.05-0820;

R. Berni, F. Formelli, In vitro interaction of fenretinide with plasma retinol-binding protein and its functional consequences, FEBS Lett. 308 (1992) 43-45. doi:10.1016/0014-5793(92)81046-O;

J. T. White, J. W. Kelly, Support for the multigenic hypothesis of amyloidosis: the binding stoichiometry of retinol-binding protein, vitamin A, and thyroid hormone influences transthyretin amyloidogenicity in vitro, Proc. Natl. Acad. Sci. USA. 98 (2001) 13019-13024. doi:10.1073/pnas.241406698;

S.-J. Hyung, S. Deroo, C. V. Robinson, Retinol and Retinol-Binding Protein Stabilize Transthyretin via Formation of Retinol Transport Complex, ACS Chem. Biol. 5 (2010) 1137-1146. doi:10.1021/cb100144v;

J. N. Buxbaum, N. Reixach, Transthyretin: the Servant of Many Masters, Cell. Mol. Life Sci. 66 (2009) 3095-3101. doi:10.1007/s00018-009-0109-0; and K. Petrukhin, New therapeutic targets in atrophic age-related macular degeneration, Expert Opin. Ther. Targets. 11 (2007) 625-39, doi:10.1517/14728222.11.5.625.

The entire contents of each of these references are incorporated herein by reference.

Some aspects of this disclosure relate to the recognition that the compounds described herein are useful for the stabilization of TTR and may inhibit TTR-RBP4 interactions. In some embodiments, the present disclosure thus provides methods of administering the compounds described herein to a subject in need thereof, e.g., a subject having or diagnosed with Macular Degeneration or Stargardt's Disease. In some embodiments, the compound is administered in an amount effective to inhibit the TTR-RBP4 interaction in the subject in need thereof, e.g., to a level of less than 50%, less than 40%, less than 30%, less than 25%, less than 20%, less than 10%, less than 5%, less than 2.5%, or less than 1% of the interaction in the subject in the absence of the compound. In some embodiments, the present disclosure provides methods of administering a compound provided herein to a subject having or diagnosed with Macular Degeneration or Stargardt's Disease in an amount effective to ameliorate at least one symptom of the Macular Degeneration or the Stargardt's Disease. In some embodiments, this disclosure provides methods of treating Macular Degeneration or Stargardt's Disease in a subject by administering an effective amount of the compound to a subject having Macular Degeneration or Stargardt's Disease. Some aspects of this disclosure thus provide that the compounds provided herein are useful for the treatment, prevention, or amelioration of one or more symptoms of AMD and STGD Some aspects of this disclosure thus provide compounds and compositions that are useful for stabilizing wild type or mutant tetrameric TTR and for reducing TTR amyloid formation, e.g., in subjects having or diagnosed with Macular Degeneration (e.g., with AMD) or STGD.

Compositions

Some aspects of this disclosure provide compounds and compositions that are useful for stabilizing wild type or mutant tetrameric TTR and for reducing TTR amyloid formation. The compounds and compositions provided herein can be incorporated in pharmaceutical formulations for therapeutic administration by a variety of routes, including but not limited to oral, parenteral, transdermal, intrathecal, ophthalmic, topical, pulmonary, nasal, rectal or depot administration.

Some aspects of this disclosure provide compounds of Formula (I):

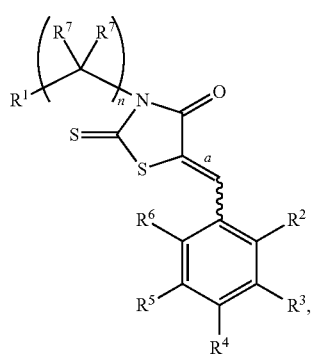

as well as pharmaceutically acceptable salts, solvates, hydrates, tautomers, stereoisomers, and prodrugs thereof, wherein:

the double bond labeled with "a" is of (E)- or (Z)- configuration;

$R^1$ is —C(=O)$OR^a$, —S(=O)$_2$NH$R^a$, —S(=O)$_2$O$R^a$, —P(=O)NH$_2$(O$R^a$), —C(=O)N($R^a$)$_2$, —C(=O)NHO$R^a$,

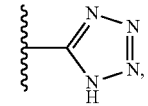

or —O$R^a$;

$R^2$ is H or Halogen;

$R^3$ is H, —OH, Halogen, —CH$_3$, or —OCH$_3$;

$R^4$ is H, —O$R^a$, F, —OCH$_3$, —NH$_2$, —ONH$_2$, —NCH$_2$, —CN, or —SH;

$R^5$ is H, —OH, Halogen, —CH$_3$, or —OCH$_3$;

$R^6$ is H or Halogen;

each instance of $R^7$ is independently H, substituted or unsubstituted C$_{1-6}$ alkyl, —C(=O)O$R^a$, or —C(=O)N($R^a$)$_2$;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring, or a CDS; and n is 1, 2, or 3.

Some aspects of this disclosure provide compounds of Formula (II):

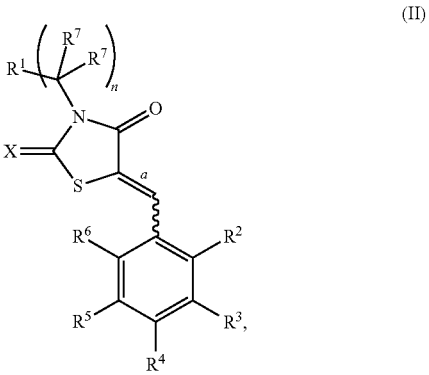

as well as pharmaceutically acceptable salts, solvates, hydrates, tautomers, stereoisomers, or prodrugs thereof, wherein:

the double bond labeled with "a" is of (E)- or (Z)- configuration;

$R^1$ is —C(=O)O$R^a$, —S(=O)$_2$NH$R^a$, —S(=O)$_2$O$R^a$, —P(=O)NH$_2$(O$R^a$), —C(=O)N($R^a$)$_2$, —C(=O)NHO$R^a$, —CHN$_4$ (tetrazolyl), or —O$R^a$;

$R^2$ is H or Halogen;

$R^3$ is H, —OH, Halogen, —CH$_3$, or —OCH$_3$;

R[4] is H, —OR[a], F, —OCH$_3$, —NH$_2$, —ONH$_2$, —NCH$_2$, —CN, or —SH;

R[5] is H, —OH, Halogen, —CH$_3$, or —OCH$_3$;

R[6] is H or Halogen;

each instance of R[7] is independently H, substituted or unsubstituted C$_{1-6}$ alkyl, —C(=O)OR[a], or —C(=O)N(R[a])$_2$;

each instance of R[a] is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R[a] are joined to form a substituted or unsubstituted, heterocyclic ring, or substituted or unsubstituted, heteroaryl ring;

n is 1, 2, or 3; and

X is O or S.

In some embodiments, the compound is of the formula:

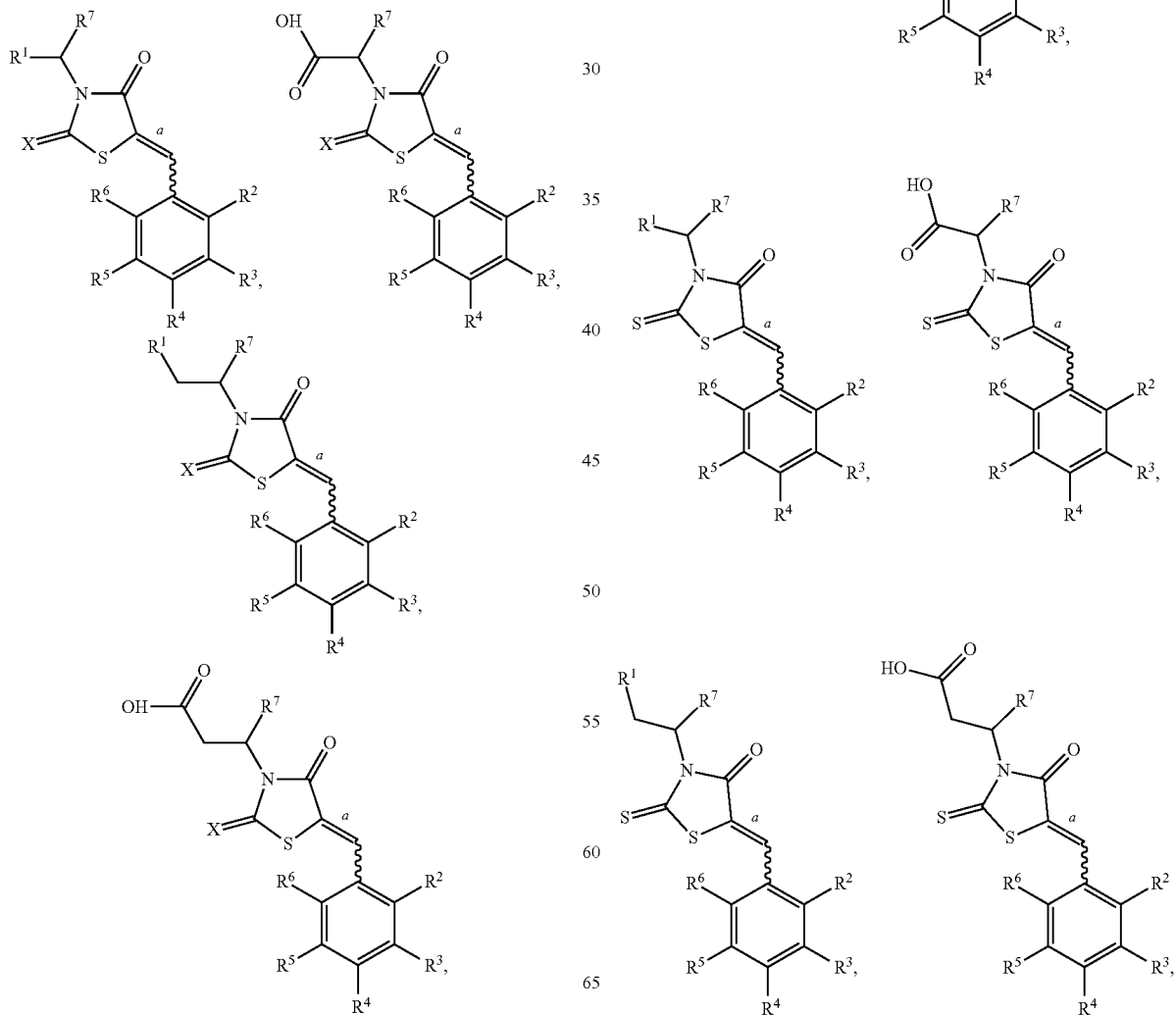

-continued

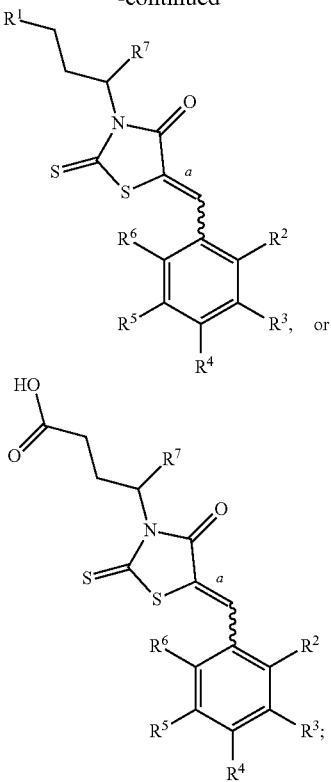

wherein each instance of $R^1$ is independently —C(=O)OR$^a$, —C(=O)N(R$^a$)$_2$, —C(=O)NHOR$^a$, or —OR$^a$, and X, $R^2$, $R^3$, $R^4$, $R^5$, $R^6$, $R^7$, and R$^a$ are as defined herein.

In some embodiments, the double bond labeled with "a" is of (E)-configuration. In some embodiments, the double bond labeled with "a" is of (Z)-configuration.

In some embodiments, $R^1$ is —C(=O)OR$^a$. In some embodiments, $R^1$ is —C(=O)OH. In certain embodiments, $R^1$ is —C(=O)O(substituted or unsubstituted $C_{1-6}$ alkyl) (e.g., —C(=O)O(unsubstituted $C_{1-6}$ alkyl), such as —C(=O)OCH$_3$). In certain embodiments, $R^1$ is —S(=O)$_2$NHR$^a$ (e.g., —S(=O)$_2$NH$_2$), —S(=O)$_2$OR$^a$ (e.g., —S(=O)$_2$OH), —P(=O)NH$_2$(OR$^a$) (e.g., —P(=O)NH$_2$(OH)), —C(=O)N(R$^a$)$_2$ (e.g., —C(=O)NH$_2$), —C(=O)NHOR$^a$ (e.g., —C(=O)NHOH),

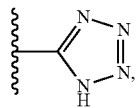

or —OR$^a$ (e.g., —OH).

In some embodiments, $R^2$ is H. In some embodiments, $R^2$ is Cl. In some embodiments, $R^2$ is F, Br, or I.

In certain embodiments, $R^3$ is H. In certain embodiments, $R^3$ is halogen. In some embodiments, $R^3$ is —OH, F, Cl, Br, —CH$_3$, or —OCH$_3$.

In some embodiments, $R^4$ is H or —OH. In some embodiments, $R^4$ is H. In certain embodiments, $R^4$ is —OR$^a$ (e.g., —O(substituted or unsubstituted $C_{1-6}$ alkyl), such as —OCH$_3$). In certain embodiments, $R^4$ is —NH$_2$, —ONH$_2$, —NCH$_2$, —CN, or —SH.

In certain embodiments, $R^5$ is H. In certain embodiments, $R^5$ is halogen. In some embodiments, $R^5$ is —OH, F, Cl, Br, —CH$_3$, or —OCH$_3$.

In some embodiments, $R^6$ is H. In some embodiments, $R^6$ is Cl. In some embodiments, $R^6$ is F, Br, or I.

When a compound of Formula (I) or Formula (II) includes two or more instances of $R^7$, any two instances of $R^7$ may be the same or different from each other. In some embodiments, at least one instance of $R^7$ is H. In some embodiments, each instance of $R^7$ is H. In some embodiments, at least one instance of $R^7$ is substituted or unsubstituted $C_{1-6}$ alkyl. In some embodiments, at least one instance of $R^7$ is —CH$_3$. In certain embodiments, at least one instance of $R^7$ is substituted methyl (e.g., —CF$_3$), Et, substituted ethyl (e.g., perfluoroethyl or benzyl), Pr, substituted propyl (e.g., perfluoropropyl), Bu, or substituted butyl (e.g., perfluorobutyl). In some embodiments, at least one instance of $R^7$ is —CH$_2$C(=O)OR$^a$, —(CH$_2$)$_2$C(=O)OR$^a$, or —(CH$_2$)$_3$C(=O)OR$^a$, optionally each instance of R$^a$ is independently substituted or unsubstituted $C_{1-6}$ alkyl. In some embodiments, at least one instance of $R^7$ is —CH$_2$C(=O)OH, —(CH$_2$)$_2$C(=O)OH, or —(CH$_2$)$_3$C(=O)OH. In some embodiments, at least one instance of $R^7$ is —C(=O)OR$^a$. In some embodiments, at least one instance of $R^7$ is —C(=O)OH. In some embodiments, at least one instance of $R^7$ is —C(=O)O(substituted or unsubstituted $C_{1-6}$ alkyl), such as —C(=O)OMe). In some embodiments, at least one instance of $R^7$ is —C(=O)N(R$^a$)$_2$ (e.g., —C(=O)NH$_2$).

In some embodiments, the compound comprises or is conjugated to a chemical delivery system (CDS). In some embodiments, at least one instance of $R^7$ comprises or is conjugated to the CDS. In some embodiments, the CDS enhances delivery of the to the central nervous system. In some embodiments, CDS enhances delivery to the brain. In some embodiments, the CDS comprises 1,4-dihydroquinoline or dihydropyridine. Additional suitable CDSs will be apparent to those of skill in the art based on the instant disclosure. Suitable chemical deliver systems include, for example, those described in Stayton et al., 'Smart' delivery systems for biomolecular therapeutics. *Orthod Craniofac Res.* 2005 August; 8(3):219-25; Țînțaș et al., New developments in redox chemical delivery systems by means of 1,4-dihydroquinoline-based targetor: application to galantamine delivery to the brain. *Eur J Med Chem.* 2014 Jun. 23; 81:218-26; Guo et al., Perspectives on brain-targeting drug delivery systems. *Curr Pharm Biotechnol.* 2012 September; 13(12):2310-8; Patel et al., Getting into the brain: approaches to enhance brain drug delivery. *CNS Drugs.* 2009; 23(1):35-58; Chen et al., Drug delivery across the blood-brain barrier. *Curr Drug Deliv.* 2004 October; 1(4): 361-76; Sheha et al., Brain delivery of HIV protease inhibitors. *Arch Pharm (Weinheim).* 2003 March; 336(1):47-52; Bodor et al., Barriers to remember: brain-targeting chemical delivery systems and Alzheimer's disease. *Drug Discov Today.* 2002 Jul. 15; 7(14):766-74; the entire contents of each of which are incorporated herein by reference.

In some embodiments, n is 1. In some embodiments, n is 2. In some embodiments, n is 3.

In some embodiments, X is S. In some embodiments, X is O.

A compound of Formula (I) or Formula (II) may include one or more instances of substituent R$^a$. When a compound of Formula (I) or Formula (II) includes two or more instances of R$^a$, any two instances of R$^a$ may be the same or different from each other. In certain embodiments, at least one instance of R$^a$ is H. In certain embodiments, each instance of R$^a$ is H. In certain embodiments, at least one instance of R$^a$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom, or two instances of $R^a$ are joined to form a substituted or unsubstituted, heterocyclic ring, or substituted or unsubstituted, heteroaryl ring.

In some embodiments, the compound is of the formula:

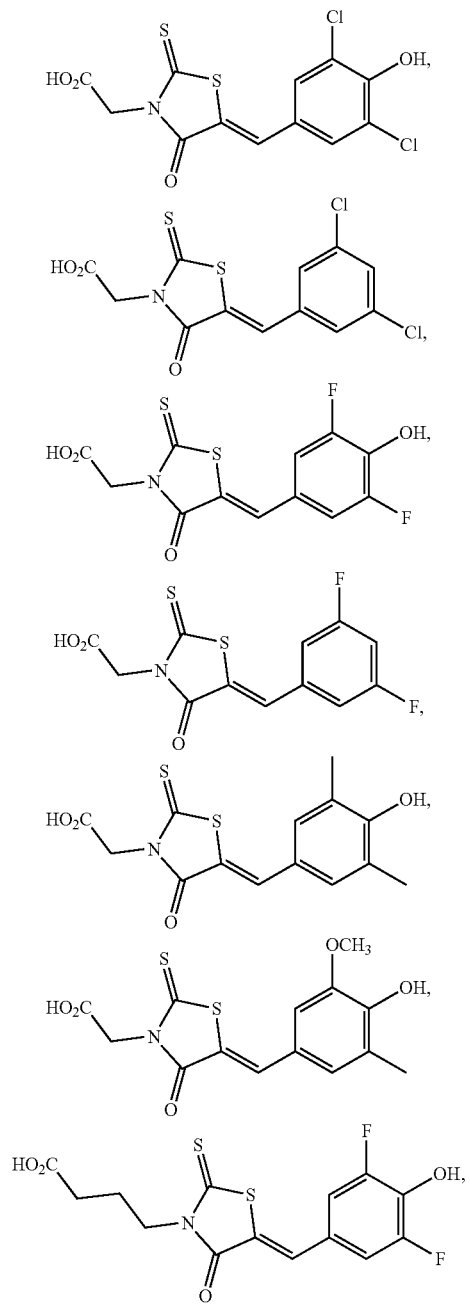

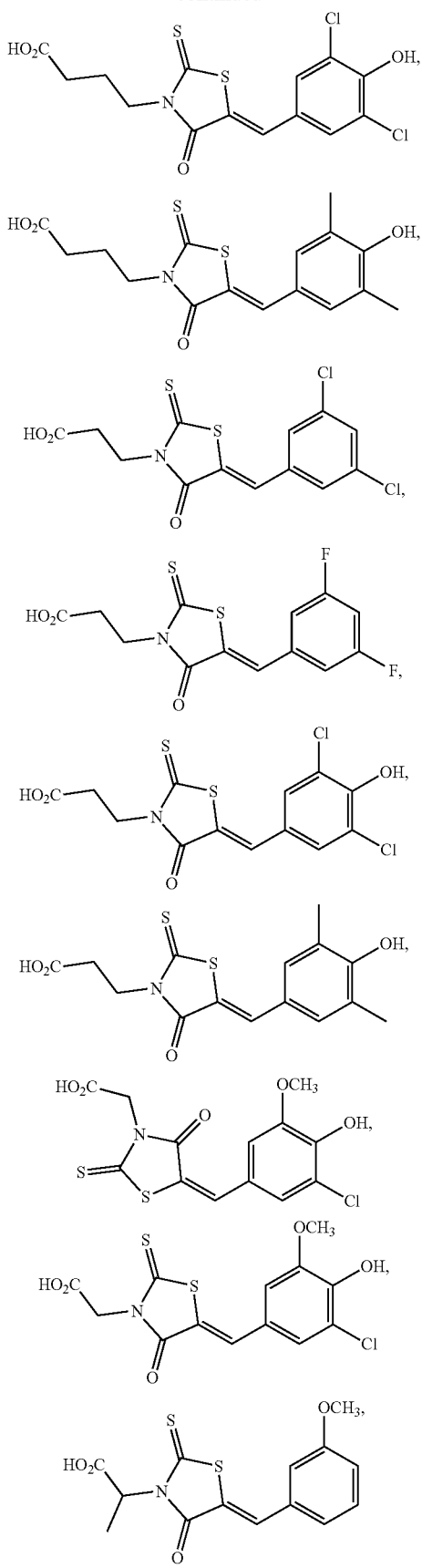

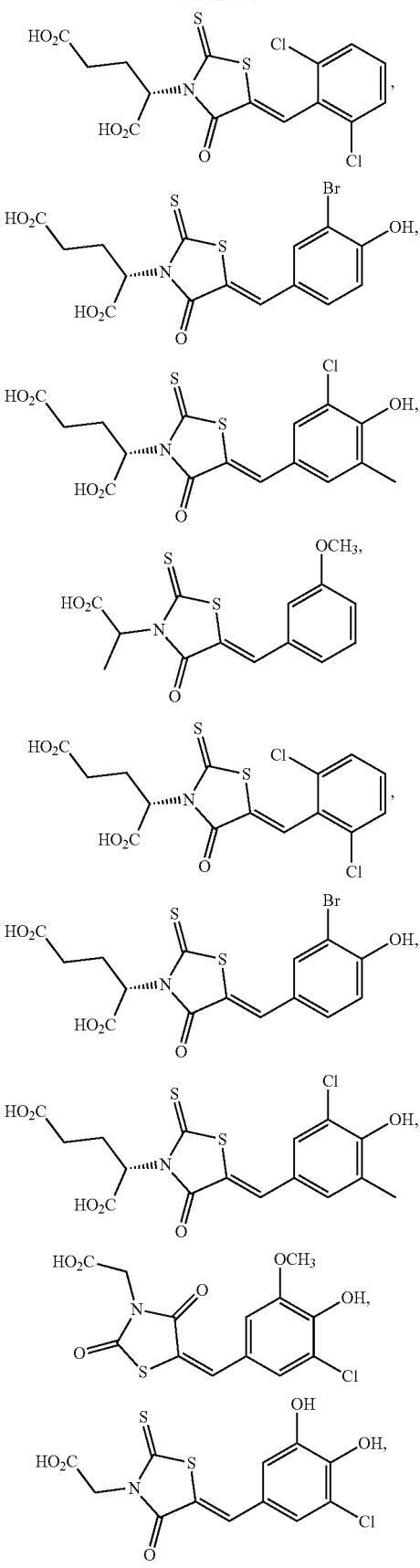
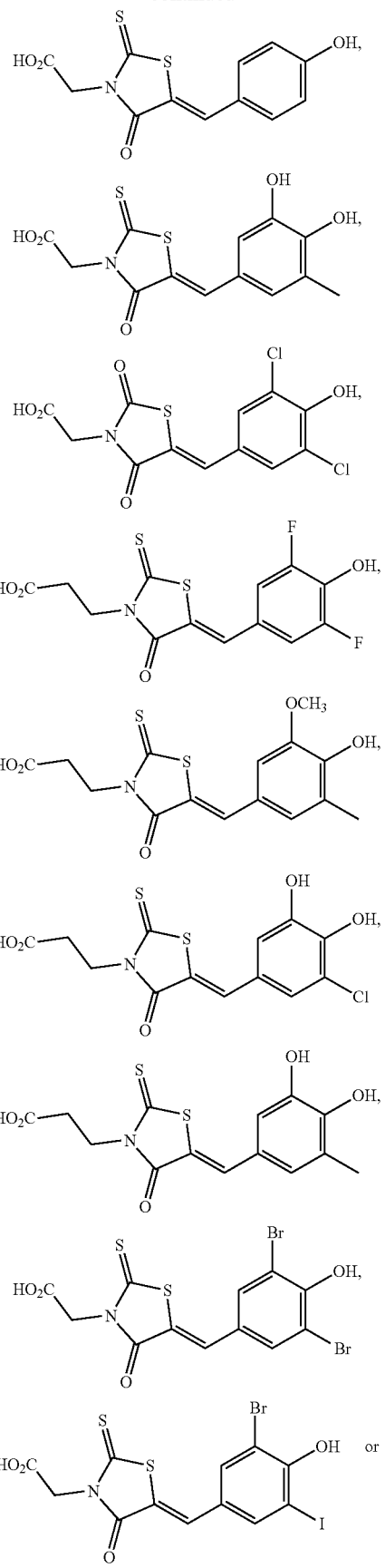

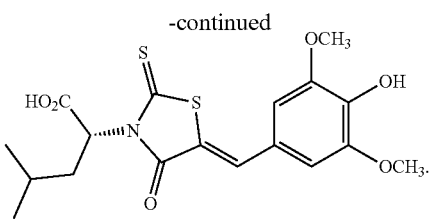

The N-substituted arylidenerhodanines and arylidenethiazolidinediones described herein have been assigned the series designation AT50.

Exemplary Synthetic Methods

Preparation of N-Substituted Arylidenerhodanines and Arylidenethiazolidinediones Most compounds belonging to the AT50 lead series were synthesized through a simple, fast and reliable microwave-assisted method, excellent isolated yields being obtained with minimal purification protocols (FIG. 1). Compounds with codes AT50-A50, AT50-A51, AT50-B00, AT50-B01, AT50-C00, AT50-C01, AT50-C02, as well as the E stereoisomer of the original virtual screening hit AT50-A00, were commercially acquired and used as received.

Figure 2:
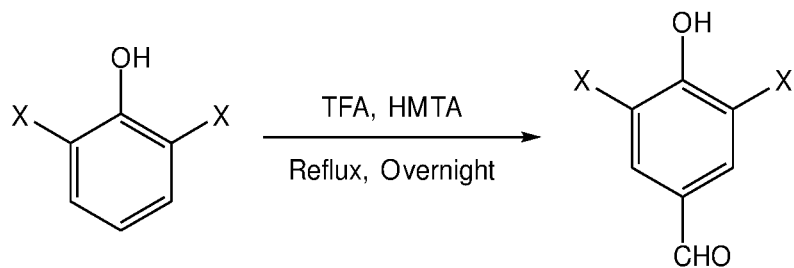
FIG. 2. Synthetic routes for the preparation of the aldehyde starting materials for the preparation of compounds with codes AT50-A01, AT50-A03, AT50-A06, AT50-A47, AT50-A49, AT50-C09, AT50-C10, AT50-C11, AT50-C13, AT50-C14, AT50-C15, AT50-C18, AT50-C19 and AT50-C20.
Figure 2:
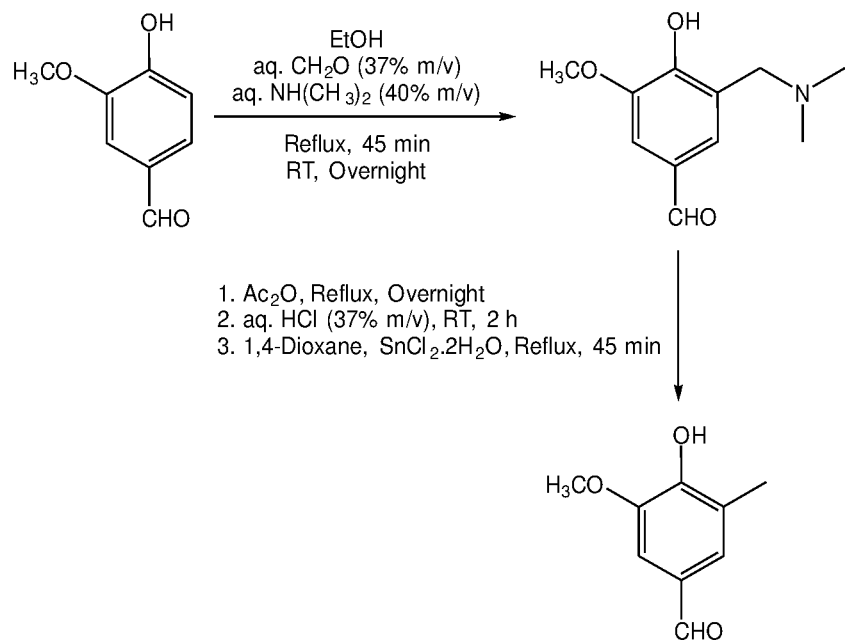
Figure 2:
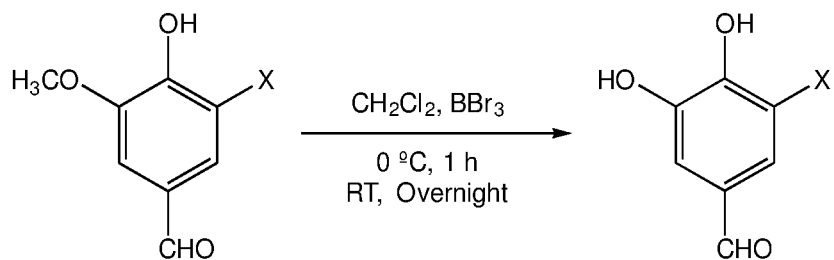
Figure 3:
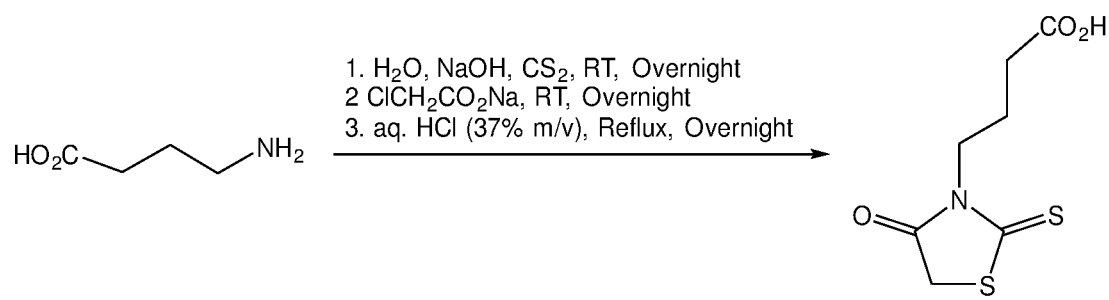
FIG. 3. Synthetic route for the preparation of rhodanine starting material for the preparation of compounds with codes AT50-C09, AT50-C10 and AT50-C11.

Regarding compounds with codes AT50-A01, AT50-A03, AT50-A05, AT50-A06, AT50-A11, AT50-A12, AT50-A35, AT50-A47, AT50-C09, AT50-C10 and AT-50-C15, the aldehyde starting materials were previously prepared via known methodologies, as shown in Scheme 1 and Scheme 2 of FIG. 2. Regarding compound AT50-A49, the thiazolidinedione starting material was previously prepared via known methodologies, as shown in Scheme 3 of FIG. 2. Regarding compounds with codes AT50-C09, AT50-C10 and AT50-C11, the rhodanine starting material was previously prepared via a known methodology (FIG. 3).

Exemplary procedures for the preparation of the compounds are described in detail in the "Experimental Procedures for the Preparation of Compounds" section of "Materials and Methods".

General Procedure for the Synthesis of Compounds AT50-A01, AT50-A03, AT50-A05, AT50-A06, AT50-A11, AT50-A12, AT50-A17, AT50-A35 and AT50-A47

A mixture of the selected aldehyde (1.5 mmol), 3-hydroxycarbonylmethyl-2-thioxothiazolidin-4-one (1.5 mmol, 293 mg) and anhydrous sodium acetate (4.5 mmol, 373 mg) in glacial acetic acid (1.5 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid.

General Procedure for the Synthesis of Compound AT50-A49

A mixture of 3,5-dichloro-4-hydroxybenzaldehyde (0.75 mmol, 145 mg), 3-hydroxycarbonylmethyl-2,4-dioxothiazolidine (0.75 mmol, 134 mg) and anhydrous sodium acetate (2.25 mmol, 187 mg) in glacial acetic acid (0.75 mL) was thoroughly mixed in an appropriate 10 mL thick-walled glass vial. This was tightly sealed with a Teflon cap and the reaction mixture was stirred and heated at 140° C. for 30 minutes, under focused microwave irradiation, with an initial power setting of 75 W. After cooling to room temperature, the crude product mixture was poured over distilled water and crushed-ice and the yellowish solid that precipitated was filtered under reduced pressure, washed with distilled water, recrystallized from dichloromethane and dried at room temperature under vacuum, yielding the desired compound as a yellow solid.

General Procedure for the Synthesis of Compounds AT50-C09, AT50-C10 and AT50-C11

A mixture of the selected aldehyde (1.5 mmol), 3-(3'-hydroxycarbonylpropyl)-2-thioxothiazolidin-4-one (1.5 mmol, 332 mg) and anhydrous sodium acetate (4.5 mmol, 373 mg) in glacial acetic acid (1.5 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid. See, e.g., FIG. 1.

General Procedure for the Synthesis of Compounds AT50-C13, AT50-C14, AT50-C15, AT50-C16, AT50-C18, AT50-C19 and AT50-C20

A mixture of the selected aldehyde (0.75 mmol), 3-(2'-hydroxycarbonylethyl)-2-thioxothiazolidin-4-one (0.75 mmol, 159 mg) and anhydrous sodium acetate (2.25 mmol, 187 mg) in glacial acetic acid (0.75 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid. See, e.g., FIG. 1.

Pharmaceutical Preparations

Certain aspects of the invention provide pharmaceutical preparations comprising a compound, pharmaceutically acceptable salt, solvate, hydrate, tautomer, stereoisomer, or prodrug thereof as described herein and a pharmaceutically acceptable carrier. The compound, pharmaceutically acceptable salt, solvate, hydrate, tautomer, stereoisomer, or prodrug thereof is also referred to herein as an active ingredient, active agent, or active compound of the pharmaceutical preparation. Additional active agents may, however, be present, e.g., an additional therapeutic agent, such as, for example, Tafamidis, Tolcapone, Donepezil, Patisiran or Resuviran. The pharmaceutical preparations provided herein are suitable for the respective route of administration. For example, a pharmaceutical preparation for parenteral administration is typically sterile and essentially non-pyrogenic. In some embodiments, preparations for other administration routes are also sterile and non-pyrogenic.

Some aspects of this disclosure provide pharmaceutical preparations comprising a compound of Formula (I):

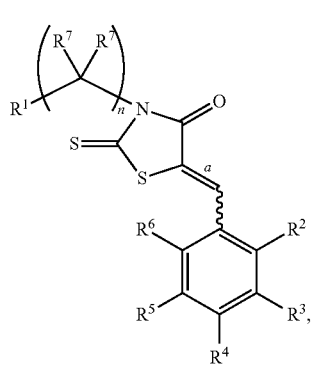

or a pharmaceutically acceptable salt, solvate, hydrate, tautomer, stereoisomer, or prodrug thereof, wherein:

the double bond labeled with "a" is of (E)- or (Z)-configuration;

R$^1$ is —C(=O)OR$^a$, —S(=O)$_2$NHR$^a$, —S(=O)$_2$OR$^a$, —P(=O)NH$_2$(OR$^a$), —C(=O)N(R$^a$)$_2$, —C(=O)NHOR$^a$,

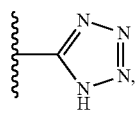

or —OR$^a$;

R$^2$ is H or Halogen;

R$^3$ is H, —OH, Halogen, —CH$_3$, or —OCH$_3$;

R$^4$ is H, —OR$^a$, F, —OCH$_3$, —NH$_2$, —ONH$_2$, —NCH$_2$, —CN, or —SH;

R$^5$ is H, —OH, Halogen, —CH$_3$, or —OCH$_3$;

R$^6$ is H or Halogen;

each instance of R$^7$ is independently H, substituted or unsubstituted C$_{1-6}$ alkyl, —C(=O)OR$^a$, or —C(=O)N(R$^a$)$_2$;

each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring, or a CDS; and n is 1, 2, or 3.

Some aspects of this disclosure provide pharmaceutical preparations comprising a compound of Formula (II):

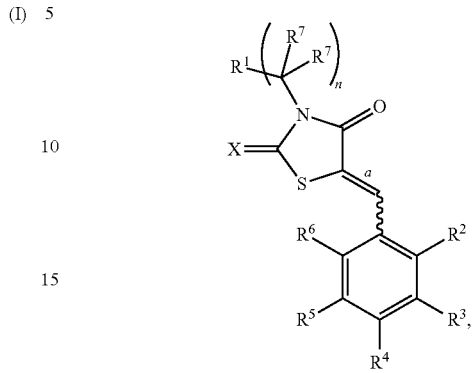

as well as pharmaceutically acceptable salts, solvates, hydrates, tautomers, stereoisomers, or prodrugs thereof, wherein:

the double bond labeled with "a" is of (E)- or (Z)-configuration;

R$^1$ is —C(=O)OR$^a$, —S(=O)$_2$NHR$^a$, —S(=O)$_2$OR$^a$, —P(=O)NH$_2$(OR$^a$), —C(=O)N(R$^a$)$_2$, —C(=O)NHOR$^a$, —CHN$_4$ (tetrazolyl), or —OR$^a$;

R$^2$ is H or Halogen;

R$^3$ is H, —OH, Halogen, —CH$_3$, or —OCH$_3$;

R$^4$ is H, —OR$^a$, F, —OCH$_3$, —NH$_2$, —ONH$_2$, —NCH$_2$, —CN, or —SH;

R$^5$ is H, —OH, Halogen, —CH$_3$, or —OCH$_3$;

R$^6$ is H or Halogen;

each instance of R$^7$ is independently H, substituted or unsubstituted C$_{1-6}$ alkyl, —C(=O)OR$^a$, or —C(=O)N(R$^a$)$_2$;

each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring;

n is 1, 2, or 3; and

X is O or S.

In some embodiments, the pharmaceutical preparation comprises a compound of the formula:

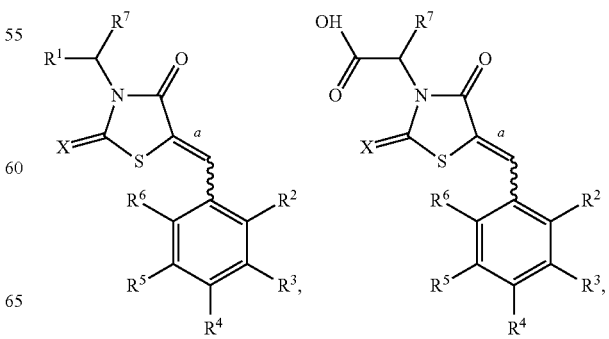

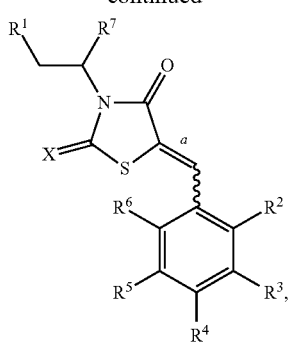
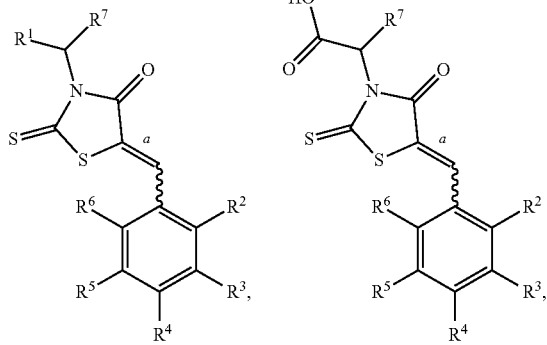
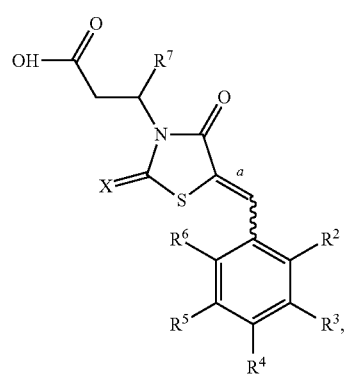
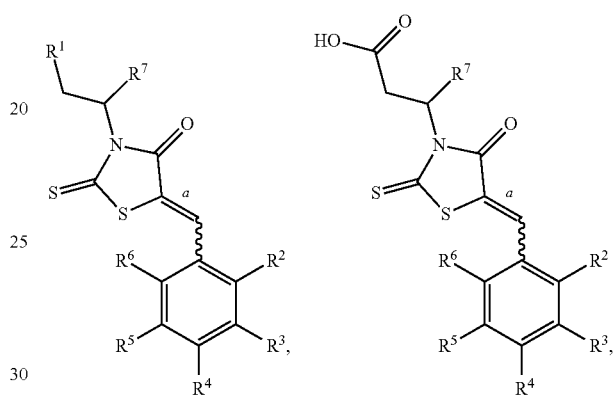
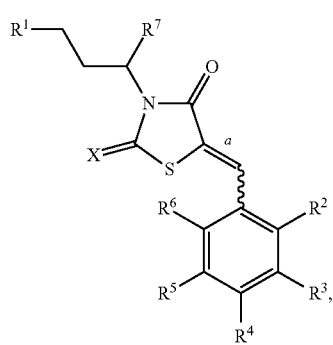
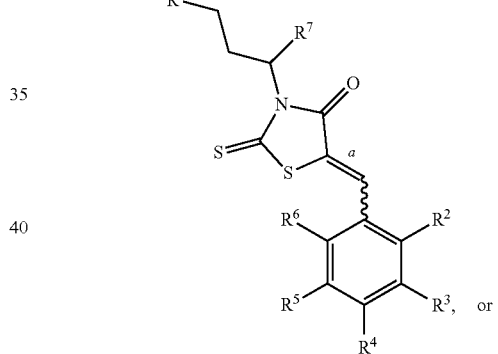
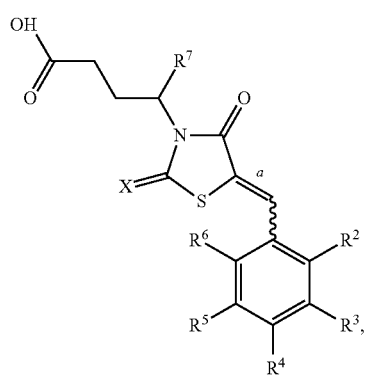
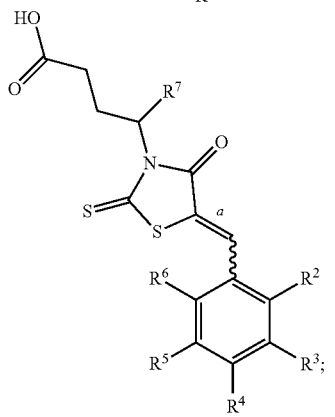
or a pharmaceutically acceptable salt, solvate, hydrate, tautomer, stereoisomer, or prodrug thereof, wherein each instance of $R^1$ is independently —C(=O)$OR^a$, —C(=O)N$(R^a)_2$, —C(=O)NHOR$^a$, or —OR$^a$, and X, $R^2$, $R^3$, $R^4$, $R^5$, $R^6$, $R^7$, and $R^a$ are as defined herein.

In some embodiments, the pharmaceutical preparation comprises a compound of the formula:
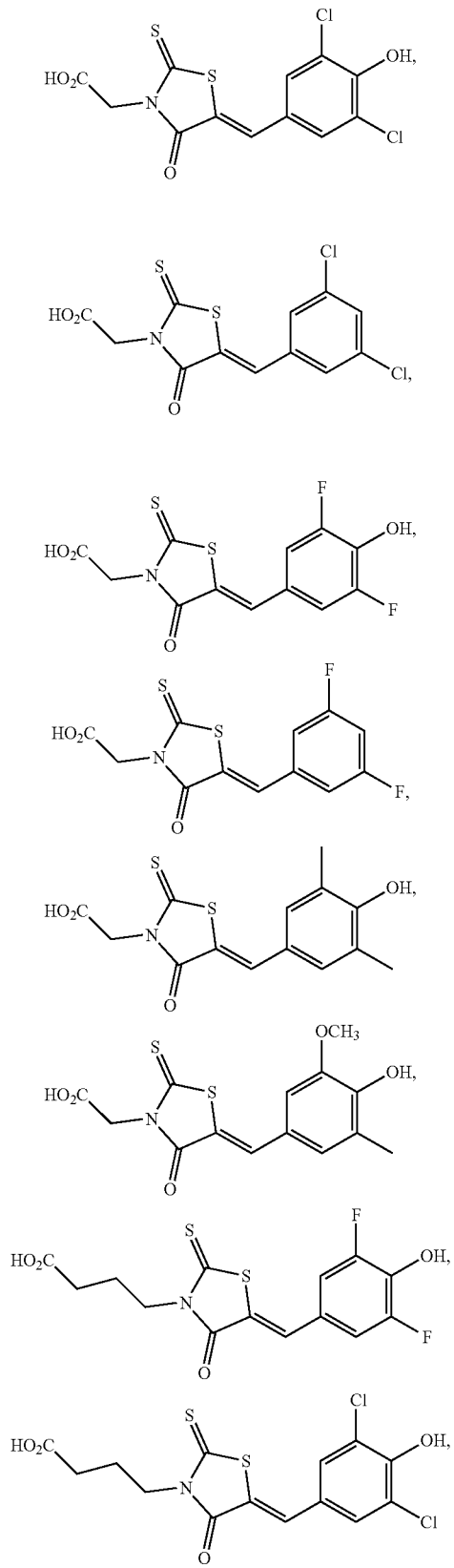
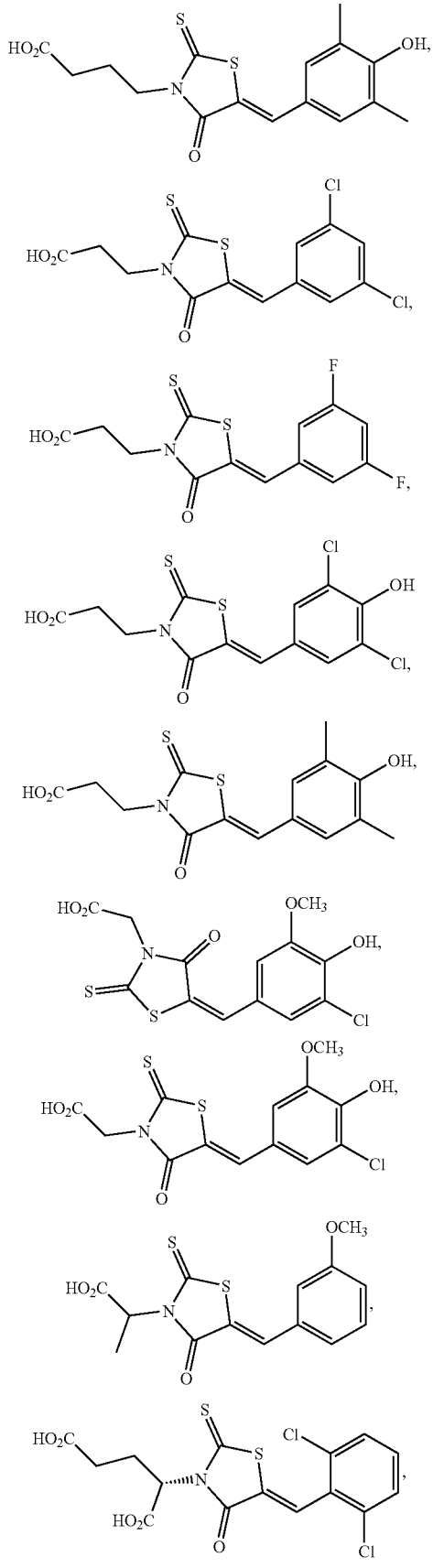

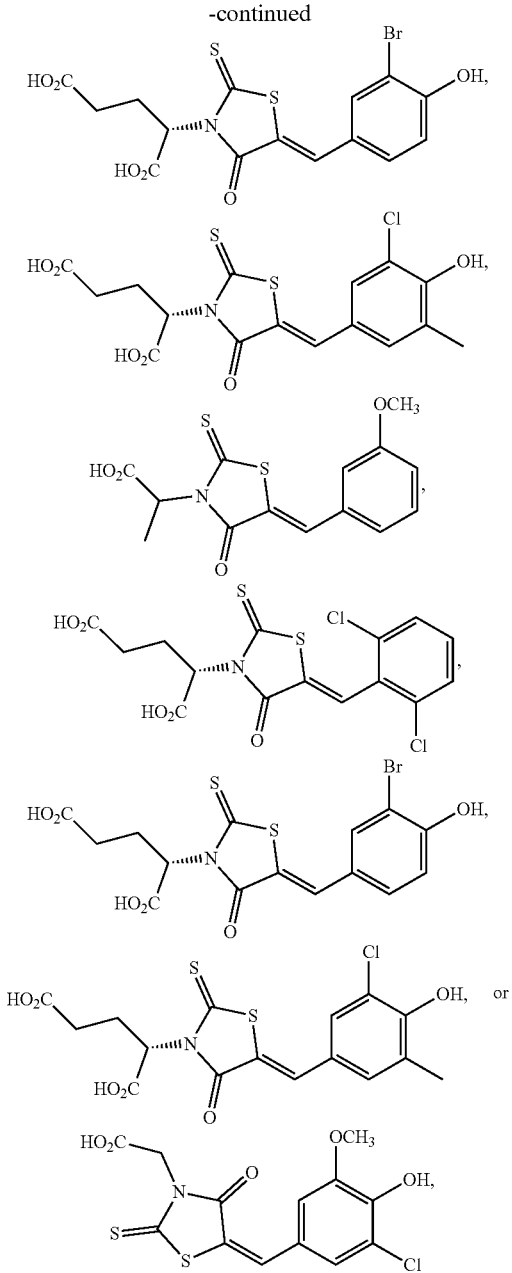

or a pharmaceutically acceptable salt, solvate, hydrate, tautomer, stereoisomer, or prodrug thereof.

In some embodiments, the pharmaceutical preparation comprises a compound, pharmaceutically acceptable salt, solvate, hydrate, tautomer, stereoisomer, or prodrug thereof as described elsewhere herein. In some embodiments, the pharmaceutical preparation comprises a chemical delivery system (CDS), for example, comprised in or conjugated to the compound, pharmaceutically acceptable salt, solvate, hydrate, tautomer, stereoisomer, or prodrug thereof. In some embodiments, the CDS enhances delivery of the compound to the central nervous system, e.g., to the brain. In some embodiments, the CDS enhances delivery of the compound across the blood brain barrier.

In some embodiments, the preparation is for administration to a human subject. In some embodiments, the preparation is sterile. In some embodiments, the preparation is essentially pyrogen-free. In some embodiments, the preparation is pyrogen-free.

Typically, the pharmaceutical preparations provided herein comprise an amount of the active ingredient, e.g., of a compound described herein, that is effective to achieve a desired effect in a subject after administration to the subject.

For example, in some embodiments, the preparation comprises the compound, or the pharmaceutically acceptable salt, solvate, hydrate, tautomer, stereoisomer, or prodrug thereof in an amount effective to inhibit amyloid fibril formation in a subject. In some embodiments, the amyloid fibril formation is transthyretin (TTR) amyloid fibril formation. In some embodiments, the preparation comprises the compound, or the pharmaceutically acceptable salt, solvate, hydrate, tautomer, stereoisomer, or prodrug thereof, in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the preparation comprises the compound, or the pharmaceutically acceptable salt, solvate, hydrate, tautomer, stereoisomer, or prodrug thereof, in an amount effective to increase TTR stability in the subject. In some embodiments, the preparation comprises the compound, or the pharmaceutically acceptable salt, solvate, hydrate, tautomer, stereoisomer, or prodrug thereof, in an amount effective to increase serum or plasma TTR stability in the subject. In some embodiments, the preparation comprises the compound, or the pharmaceutically acceptable salt, solvate, hydrate, tautomer, stereoisomer, or prodrug thereof, in an amount effective to increase the ratio of tetrameric TTR to monomeric TTR in the subject. In some embodiments, the preparation comprises the compound, or the pharmaceutically acceptable salt, solvate, hydrate, tautomer, stereoisomer, or prodrug thereof, in an amount effective to increase the level of tetrameric TTR in the subject and/or to decrease the level of monomeric TTR in the subject.

In some embodiments, the pharmaceutical preparation comprises the compound, or the pharmaceutically acceptable salt, solvate, hydrate, tautomer, stereoisomer, or prodrug thereof, in an amount effective to increase the stability of TTR, increase the level of tetrameric TTR, decrease the level of monomeric TTR, and/or increase the ratio of tetrameric to monomeric TTR in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In some embodiments, the pharmaceutical preparation comprises the compound, or the pharmaceutically acceptable salt, solvate, hydrate, tautomer, stereoisomer, or prodrug thereof, in an amount effective to inhibit interactions between TTR and Retinol Binding Protein 4 (RBP4) in the serum of a subject. In some embodiments, the term "interactions" in the context of TTR and RBP4 refers to binding of TTR to RBP4. In some embodiments, the preparation comprises the compound, or the pharmaceutically acceptable salt, solvate, hydrate, tautomer, stereoisomer, or prodrug thereof, in an amount effective to decrease the interactions of TTR with RBP4 in the serum of the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the interactions in the absence of the compound, the pharmaceutically acceptable salt, solvate, hydrate, tautomer, stereoisomer, or prodrug thereof. In some embodiments, the preparation comprises the compound, or the pharmaceutically acceptable salt, solvate, hydrate, tautomer, stereoisomer, or prodrug thereof, in an amount effective to increase renal clearance of RBP4 in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the renal clearance of RBP4 in the absence of the compound, the pharmaceutically acceptable salt, solvate, hydrate, tautomer, stereoisomer, or prodrug thereof.

In some embodiments, the preparation comprises the compound, or the pharmaceutically acceptable salt, solvate, hydrate, tautomer, stereoisomer, or prodrug thereof, in an amount effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in the subject. In some embodiments, the ratio of tetrameric to monomeric TTR in the subject before administration of the pharmaceutical preparation is lower than the ratio observed or expected in a healthy subject, lower than the average ratio observed in an age- and gender-matched population, or less than 0.72, less than 0.71, less than 0.7, less than 0.69, less than 0.68, less than 0.67, less than 0.66, less than 0.65, or less than 0.5. In some embodiments, the subject carries a TTR mutation associated with an amyloid disease. In some embodiments, the subject carries a TTR mutation associated with an amyloid disease but does not exhibit an abnormal TTR stability or a symptom of the amyloid disease.

In some embodiments, the preparation comprises the compound, or the pharmaceutically acceptable salt, solvate, hydrate, tautomer, stereoisomer, or prodrug thereof in an amount effective to ameliorate at least one symptom of an amyloid disease in the subject. In some embodiments, the symptom is neuropathy, neurological impairment, neurological dysfunction, cognitive deficiency, nutritional deficiency, and TTR stabilization. In some embodiments, the amyloid disease is AA amyloidosis, Alzheimer's disease, Light-Chain (AL) amyloidosis, Type-2 Diabetes, Medullary Carcinoma of the Thyroid, Parkinson's disease, Polyneuropathy, Spongiform Encephalopathy (Creutzfeldt Jakob disease), Familial Amyloid Polyneuropathy, Familial Amyloid Cardiomyopathy, or Senile Systemic Amyloidosis.

In some embodiments, the preparation comprises a dose of 0.1-1000 mg of the compound or the pharmaceutically acceptable salt, solvate, hydrate, tautomer, stereoisomer, or prodrug thereof per kg body weight of the subject. For example, in some embodiments, the preparation comprises a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg. In some embodiments, the preparation comprises a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg.

In some embodiments, the pharmaceutical preparation is provided in a dosage form, e.g., in a dosage form for parenteral or for oral administration. In some such embodiments, the pharmaceutical preparation is in the form of a dosage form for oral administration, e.g., in the form of a pill, tablet, capsule, lozenge, gel, or other suitable dosage form. In some embodiments, the dosage form for administration comprises 1 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 200 mg, 250 mg, 300 mg, 400 mg, 500 mg, 600 mg, 700 mg, 750 mg, 800 mg, 900 mg, or 1000 mg of the compound, or the pharmaceutically acceptable salt, solvate, hydrate, tautomer, stereoisomer, or prodrug thereof. In some embodiments, the dosage form comprises 0.1-10 mg, 0.1-100 mg, 1-10 mg, 1-100 mg, 1-1000 mg, 10-100 mg, 10-1000 mg, 100-1000 mg, 10-50 mg, 10-25 mg, 10-20 mg, 50-100 mg, or 100-250 mg of the compound, or the pharmaceutically acceptable salt, solvate, hydrate, tautomer, stereoisomer, or prodrug thereof.

In some embodiments, the preparation comprises a micronized form of the compound or of the pharmaceutically acceptable salt, solvate, hydrate, tautomer, stereoisomer, or prodrug thereof. Suitable methods for micronization of compounds are known to those of skill in the art and the disclosure is not limited in this respect.

In some embodiments, the pharmaceutical preparation further comprises at least one additional compound, or a pharmaceutically acceptable salt, solvate, hydrate, tautomer, stereoisomer, or prodrug thereof, wherein the at least one additional compound is approved for therapy of an amyloid disease. Such compositions allow for combination therapy of amyloid diseases. In some embodiments, such combination therapy is used to achieve an additive or synergistic effect of the therapeutic compounds used. In some such embodiments, the compounds are administered at their maximum tolerated dose to achieve the maximum therapeutic effect.

In other embodiments, the subject to be treated with the combination is a subject in which monotherapy has not yielded the desired effect. In some embodiments, administering a single compound to treat amyloid disease, e.g., a compound already approved for human treatment or in clinical trials, is not successful in the subject because the compound is toxic or causes inacceptable side effects when administered to the subject at effective doses. In such cases, a combination therapy may be employed in which two compounds targeted at ameliorating a symptom of the amyloid disease are administered at sub-toxic doses to yield an additive or synergistic therapeutic effect without the toxicity associated with single compound treatment regimen. For example, in some embodiments, the additional compound is Tafamidis, Tolcapone, Donepezil, Patisiran or Resuviran.

In some embodiments, a pharmaceutical preparation provided herein is for use in the treatment of an amyloid disease, for example, AA amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

In some embodiments, a compound, or a pharmaceutically acceptable salt, solvate, hydrate, tautomer, stereoisomer, or prodrug thereof, described herein is administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the active agent, e.g., the compound, or a pharmaceutically acceptable salt, solvate, hydrate, tautomer, stereoisomer, or prodrug thereof, can be administered to a subject by any mode that delivers the active agent to the desired surface. Administering the pharmaceutical preparation of the present invention may be accomplished by any means known to the skilled artisan. Preferred routes of administration include but are not limited to oral, parenteral, intramuscular, intranasal, sublingual, intratracheal, and inhalation.

For oral administration, the compounds (e.g., a compound of Formula (I) or Formula (II), or a pharmaceutically acceptable salt, solvate, hydrate, tautomer, stereoisomer, or prodrug thereof, or other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the active agent (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the active agent (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the active agent or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the active agents (or derivatives thereof). The active agent (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

Such devices use formulations suitable for the dispensing of active agent (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified active agent may also be prepared in different formulations depending on the type of chemical modification or the type of device employed.

Formulations suitable for use with a nebulizer, either jet or ultrasonic, will typically comprise active agent (or derivative) dissolved in water at a concentration of about 0.1 to 25 mg of biologically active agent per mL of solution. The formulation may also include a buffer and a simple sugar (e.g., for active agent stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device will generally comprise a finely divided powder containing the active agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing active agent (or derivative) and may also include a bulking agent, such as lactose, sorbitol, sucrose, or mannitol in amounts which facilitate dispersal of the powder from the device, e.g., 50 to 90% by weight of the formulation. The active agent (or derivative) should most advantageously be prepared in particulate form with an average particle size of less than 10 micrometers (μm), most preferably 0.5 to 5 μm, for most effective delivery to the distal lung.

Nasal delivery of a pharmaceutical preparation of the present invention is also contemplated. Nasal delivery allows the passage of a pharmaceutical preparation of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical preparation of the present invention solution into a chamber of defined volume, which chamber has an aperture dimensioned to aerosolize and aerosol formulation by forming a spray when a liquid in the chamber is compressed. The chamber is compressed to administer the pharmaceutical preparation of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds described herein, or the pharmaceutically acceptable salts, solvates, hydrates, tautomers, stereoisomers, or prodrugs thereof, may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical preparations for parenteral administration include aqueous solutions of the active agent(s) in water-soluble form. Additionally, suspensions of the active agent(s) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In some embodiments, the active agent(s) may be in powder form for constitution with a suitable vehicle, e.g., sterile, pyrogen-free water or a suitable buffer, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical preparations also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical preparations also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical preparations are suitable for use in a variety of drug delivery systems. For a brief review of methods for drug delivery, see Langer, *Science* 249:1527-1533, 1990, which is incorporated herein by reference.

The active agents and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including specifically but not limited to the active agent, may be provided in particles. Particles as used herein means nano or microparticles (or in some instances larger) which can consist in whole or in part of the active agent or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the active agent in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J.

A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Methods of Use

Some aspects of this disclosure provide methods of using the compounds, pharmaceutically acceptable salts, solvates, hydrates, tautomers, stereoisomers, and prodrugs provided herein for inhibiting amyloid fibril formation and for treating amyloid diseases including, but not limited to, Familial Amyloid Polyneuropathy, Familial Amyloid Cardiomyopathy, Senile Systemic Amyloidosis, AA amyloidosis, Alzheimer's disease, Light-Chain (AL) amyloidosis, Type-2 Diabetes, Medullary Carcinoma of the Thyroid, Parkinson's disease, Polyneuropathy, and Spongiform Encephalopathy (Creutzfeldt Jakob disease).

Some aspects of this disclosure provide methods for inhibiting amyloid fibril formation in a subject. The methods comprise administering to a subject in need thereof a compound as provided herein, e.g., a compound of Formula (I) or Formula (II), or a pharmaceutically acceptable salt, solvate, hydrate, tautomer, stereoisomer, or prodrug thereof, or a pharmaceutical preparation provided herein. In some embodiments, the subject exhibits an increased level of amyloid fibril formation as compared to a reference level. In some embodiments, the reference level is a level observed or expected in a healthy subject or a population of healthy subjects. In some embodiments, the amyloid fibril formation is transthyretin amyloid fibril formation. In some embodiments, the subject has or has been diagnosed with an amyloid disease. In some embodiments, the amyloid disease is a transthyretin amyloid disease. In some embodiments, he amyloid disease is Familial Amyloid Polyneuropathy. In some embodiments, the amyloid disease is Familial Amyloid Cardiomyopathy. In some embodiments, the amyloid disease is Senile Systemic Amyloidosis. In some embodiments, the amyloid disease is Alzheimer's Disease.

Some aspects of this disclosure provide methods for treating an amyloid disease. In some embodiments, the method comprising administering to a subject in need thereof a compound provided herein, or a pharmaceutically acceptable salt, solvate, hydrate, tautomer, stereoisomer, or prodrug thereof, or a pharmaceutical preparation provided herein. Typically, such methods comprise administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the amyloid disease in the subject. In some embodiments, the amyloid disease is AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease). In some embodiments, the amyloid disease is Familial Amyloid Polyneuropathy, Familial Amyloid Cardiomyopathy, Senile Systemic Amyloidosis.

In some embodiments, the method for inhibiting amyloid fibril formation or for treating an amyloid disease comprises administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the amyloid disease in the subject. In some embodiments, the method comprises administering the compound, the pharmaceutically acceptable salt, solvate, hydrate, tautomer, stereoisomer, or prodrug thereof, or the pharmaceutical preparation at a dosage of 0.1-1000 mg of the compound or the pharmaceutically acceptable salt, solvate, hydrate, tautomer, stereoisomer, or prodrug thereof per kg body weight of the subject per day. In some embodiments, the method comprises administering a dose as provided herein. For example, in some embodiments, the method comprises administering a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg to the subject. In some embodiments, the method comprises administering a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg to the subject. In some embodiments, the method comprises administering a pharmaceutical preparation as provided herein via a parenteral or an oral administration route. For example, in some embodiments, the method comprises administering an oral dosage form, e.g., in the form of a pill, tablet, capsule, lozenge, gel, or other suitable oral dosage form, comprising 1 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 200 mg, 250 mg, 300 mg, 400 mg, 500 mg, 600 mg, 700 mg, 750 mg, 800 mg, 900 mg, or 1000 mg of a compound, or a pharmaceutically acceptable salt, solvate, hydrate, tautomer, stereoisomer, or prodrug thereof as provided herein to the subject. In some embodiments, the method comprises administering a dosage form comprises 0.1-10 mg, 0.1-100 mg, 1-10 mg, 1-100 mg, 1-1000 mg, 10-100 mg, 10-1000 mg, 100-1000 mg, 10-50 mg, 10-25 mg, 10-20 mg, 50-100 mg, or 100-250 mg of the compound, or the pharmaceutically acceptable salt, solvate, hydrate, tautomer, stereoisomer, or prodrug thereof.

In some embodiments, the dose or dosage form is administered to the subject once a day, twice a day, or three times a day. In other embodiments, the dose is administered to the subject once a week, once a month, once every two months, four times a year, three times a year, twice a year, or once a year.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation at a dosage effective to increase the stability of TTR, increase the level of tetrameric TTR, decrease the level of monomeric TTR, and/or increase the ratio of tetrameric to monomeric TTR in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation at a dosage effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in the subject.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the method for inhibiting amyloid fibril formation or for treating an amyloid disease further comprises administering at least one additional compound to the subject, wherein the at least one additional compound is approved for therapy of an amyloid disease. In some embodiments, the additional compound is Tafamidis, Tolcapone, Donepezil, Patisiran or Resuviran. In some embodiments, the method comprises administering the additional compound at the dosage commonly used for that compound when administered alone. In some embodiments, the additional compound is administered at a dosage below the dosage commonly used in single therapy with the compound. In some embodiments, both the compound, the pharmaceutically acceptable salt, solvate, hydrate, tautomer, stereoisomer, or prodrug thereof, or the pharmaceutical preparation described herein and the additional compound are administered at dosages that are below the maximum effective dose when administered alone.

In some embodiments, the method for inhibiting amyloid fibril formation or for treating an amyloid disease comprises identifying the subject as exhibiting an increased level of amyloid fibril formation as compared to a reference level or as having an amyloid disease. In some embodiments, the subject is identified as exhibiting an increased level of amyloid fibril formation as compared to a reference level, as having an amyloid disease, or as being at an above-average risk of developing an amyloid disease by performing an analysis of a sample obtained of the subject. In some embodiments, the sample is a body fluid, cell, or tissue sample obtained from the subject. In some embodiments, the analysis comprises detecting the presence of amyloid fibrils, a level of transthyretin expression, and/or a mutation in the transthyretin gene in the sample, analysis of abdominal fat, and/or imaging studies of the heart of the subject.

In some embodiments, the method for treating an amyloid disease is aimed to ameliorate an existing condition, for example, an existing amyloid disease in a subject. In some embodiments, the treatment is aimed to prevent a condition, e.g., an amyloid disease, or a symptom of such a condition, e.g., cognitive dysfunction or neuropathology, from occurring or from recurring. For example, in some embodiments, a compound, composition, or preparation as described herein is administered to a subject having an amyloid disease or exhibiting a decreased level of TTR in order to inhibit TTR amyloid fibril formation. For another example, in some embodiments, a compound, composition, or preparation as described herein is administered to a subject having an amyloid disease in addition to another clinical intervention to treat the amyloid disease, e.g., in addition to a liver transplant in a subject having a mutated TTR gene, in order to prevent or delay recurrence of the disease, e.g., via TTR from non-liver sources. In other embodiments, a compound, composition, or pharmaceutical preparation as described herein is administered to a subject not showing symptoms of an amyloid disease, such as cognitive dysfunction or neuropathology, but known to be predisposed or at an elevated risk to develop an amyloid disease, for example, based on familial history or genetic testing. In such embodiments, the administration may delay or prevent the onset of a symptom associated with an amyloid disease.

Some embodiments disclosed herein include a choice of treatment, referring to a selection of a clinical intervention from a number of alternatives, e.g., from the various compounds, compositions, or pharmaceutical preparations described herein, or further including additional treatment options for amyloid disease, e.g., treatment with Tafamidis or Donepezil, or via liver transplantation. In some embodiments, a choice of treatment involves the design of a personalized therapeutic approach for a subject having an amyloid disease based on the results from diagnostic methods. For example, in some embodiments, a choice of treatment includes administering to a subject having an amyloid disease a specific compound, composition, or pharmaceutical preparation described herein, based on a determination that the subject exhibits decreased TTR stability, e.g., as measured by a ratio of tetrameric to monomeric TTR in the plasma of the subject being below a threshold level indicating normal TTR stability, or based on determining that the subject carries a TTR mutation associated with an amyloid disease, e.g., by performing genetic analysis on a biological sample obtained from the subject. In some embodiments, a choice of treatment includes the determination of an appropriate treatment and dosage regimen. Some embodiments further include carrying out the selected treatment, e.g., by administering a compound, composition, or pharmaceutical preparation described herein according to an appropriate treatment and dosage regimen.

In some embodiments, the method of treating an amyloid disease comprises administering a compound, the pharmaceutically acceptable salt, solvate, hydrate, tautomer, stereoisomer, or prodrug thereof, or a pharmaceutical preparation as described herein at a dosage effective to ameliorate a symptom of the amyloid disease, e.g., a neuropathy, neurological impairment, neurological dysfunction, impairment of motor function, impairment of sensory function, impairment of memory, or cognitive deficiency in the subject. In some embodiments, the method further comprises monitoring at least one symptom associated with the amyloid disease in the subject during the treatment or after treatment has been administered. This may include, in some embodiments, testing motor function, sensory function, cognitive function, or memory function in the subject. While some exemplary symptoms of amyloid disease are described herein, other symptoms will be apparent to those of skill in the art. In addition, the skilled artisan will be able to identify suitable tests for monitoring such symptoms in a subject, e.g., by administering a suitable test for motor function, sensory function, cognitive function, or memory function in the subject. The disclosure is not limited in this respect.

In some embodiments, this disclosure provides a method comprising administering a compound provided herein, e.g., a compound of Formula (I) or a compound of Formula (II), or a pharmaceutically acceptable salt, solvate, hydrate, tautomer, stereoisomer, or prodrug thereof, to a subject in an amount effective to inhibit interactions between TTR and Retinol Binding Protein 4 (RBP4) in the serum of the subject. In some embodiments, the interactions are binding. In some embodiments, the method comprises administering the compound, or the pharmaceutically acceptable salt, solvate, hydrate, tautomer, stereoisomer, or prodrug thereof, in an amount effective to decrease the interactions of TTR with RBP4 in the serum of the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the interactions in the absence of the compound, the pharmaceutically acceptable salt, solvate, hydrate, tautomer, stereoisomer, or prodrug thereof. In some embodiments, the method comprises administering the compound, or the pharmaceutically acceptable salt, solvate, hydrate, tautomer, stereoisomer, or prodrug thereof, in an amount effective to increase renal clearance of RBP4 in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the renal clearance of RBP4 in the absence of the compound, the pharmaceutically acceptable salt, solvate, hydrate, tautomer, stereoisomer, or prodrug thereof. In some embodiments, the method comprises administering the compound, or the pharmaceutically acceptable salt, solvate, hydrate, tautomer, stereoisomer, or prodrug thereof in an amount effective to ameliorate at least one symptom of Macular degeneration or Stargardt's disease or a related oculopathy. In some embodiments, the Macular Degeneration is Age-Related Macular Degeneration.

Some embodiments of this disclosure provide methods of treating Macular Degeneration, Stargardt's disease, or a related oculopathy. In some embodiments, the method comprises administering to a subject in need thereof a compound provided herein, e.g., a compound of Formula (I) or a compound of Formula (II), or a pharmaceutically acceptable salt, solvate, hydrate, tautomer, stereoisomer, or prodrug thereof, or a pharmaceutical preparation provided herein. In some embodiments, the method comprises administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the Macular Degeneration, Stargardt's disease, or a related oculopathy. In some embodiments, the Macular Degeneration is Age Related Macular Degeneration. In some embodiments, the method comprises administering the compound, the pharmaceutically acceptable salt, solvate, hydrate, tautomer, stereoisomer, or prodrug thereof, or the pharmaceutical preparation at a dosage of 0.1-1000 mg of the compound or the pharmaceutically acceptable salt, solvate, hydrate, tautomer, stereoisomer, or prodrug thereof per kg body weight of the subject per day. In some embodiments, the method comprises administering the compound, the pharmaceutically acceptable salt, solvate, hydrate, tautomer, stereoisomer, or prodrug thereof, or the pharmaceutical preparation at a dosage effective to increase TTR stability, to inhibit TTR interactions with RBP4 in the serum of the subject, or to increase renal clearance of RBP in the subject. In some embodiments, the method further comprises administering at least one additional compound to the subject, wherein the at least one additional compound is approved for therapy of Macular Degeneration, Stargardt's Disease, or a related oculopathy. In some embodiments, the method further comprises identifying the subject as having Macular Degeneration, Stargardt's disease, or a related oculopathy.

The present invention is further illustrated by the following Examples, which are provided to illustrate some embodiments of this disclosure and are not to be construed as limiting. The entire contents of all of the references (including literature references, issued patents, published patent applications, and co-pending patent applications, if any) cited throughout this application are hereby expressly incorporated by reference.

EXAMPLES

Example 1

Figure 4:
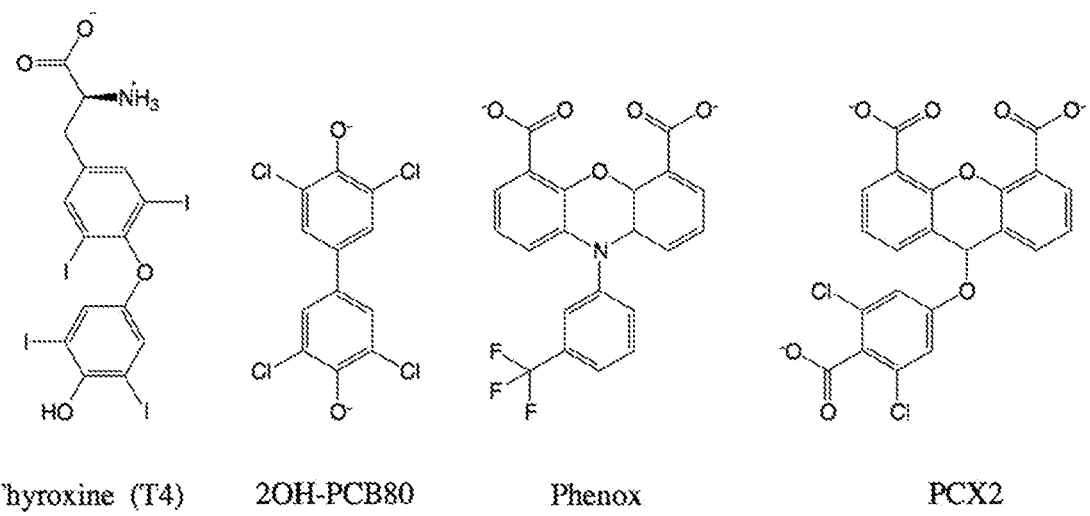
FIG. 4. Chemical formulae of compounds used as template for ligand-based virtual screening. Thyroxine (T4) is a thyroid hormone and the main endogenous transthyretin (TTR) binder; 2OH-PCB80 belongs to an important class of toxic organic pollutants and is one of the most potent TTR-amyloid inhibitor known to date; Phenox is a known TTR ligand resulting from structure-based design; PCX2 is a modeled compound, a concatamer, which attempts to combine key pharmacophoric features found in all three TTR ligands: T4, 2OH-PCB80 and Phenox.

Selection of 2-hydroxy-3-[(4-methoxyphenyl)carbonylamino]benzoic acid for Biochemical Evaluation Prioritization of 2-hydroxy-3-[(4-methoxyphenyl)carbonylamino]benzoic acid (here labeled AT12-A00) for biochemical evaluation of inhibitory activity against amyloid formation by transthyretin (TTR) proceeded as follows. A virtual chemical library containing 2,259,573 small organic molecules deposited in the ZINC database was screened using a ligand-based virtual screening (VS) protocol and Phenox as template/query (Phenox is represented in FIG. 4).

Figure 5:
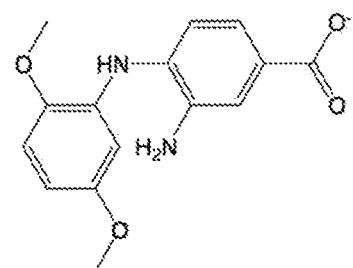
FIG. 5. Chemical formulae and corresponding ZINC codes of the top-10 virtual screening (VS) hits predicted to be soluble, very or highly soluble. Phenox was used as template ligand in this screening run. Compound AT12-A00 (ZINC code 01429477) is ranked third within this set of VS solutions.
Figure 5:
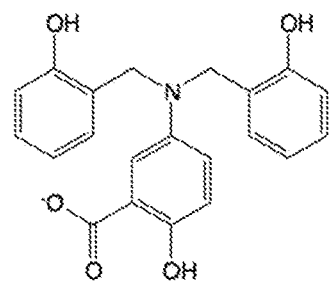
Figure 5:
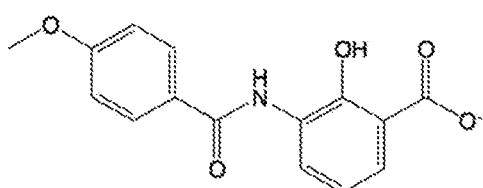
Figure 5:
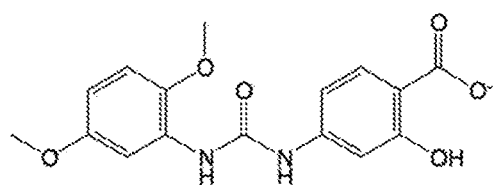
Figure 5:
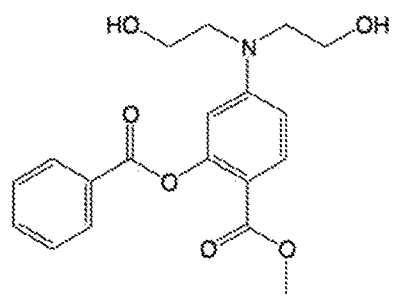
Figure 5:
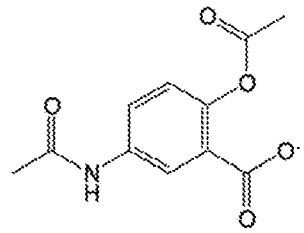
Figure 5:
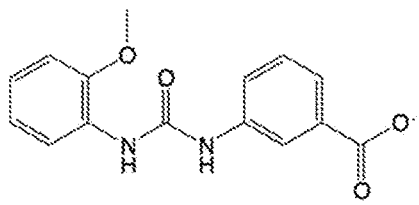
Figure 5:
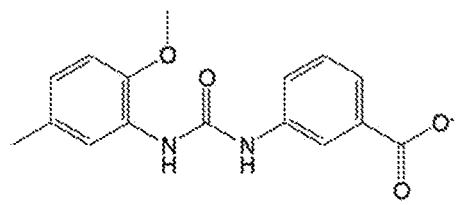
Figure 5:
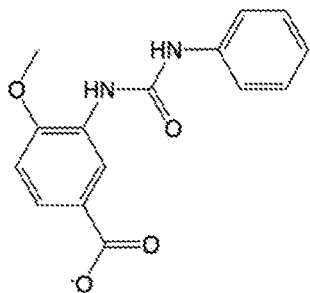
Figure 5:
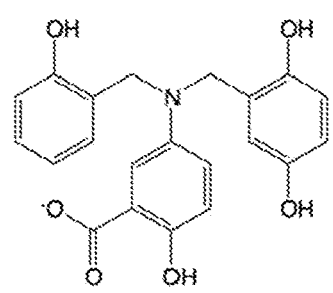

Compound 2-hydroxy-3-[(4-methoxyphenyl)carbonylamino]benzoic acid (AT12-A00) was discovered among the top-hundred VS solutions, more precisely at position 26 of the ranked chemical library, with ZINC code 01429477. Because Phenox is predicted "insoluble", holding a predicted Log P (x Log P) of 4.71, and an aggregator in solution, a strict set of criteria for physicochemical properties described in the discovery workflow (Materials and Methods section) were applied as post-screening filter of the top-thousand VS solutions. This filtering procedure placed compound ZINC01429477 among the top-ten VS hits predicted as soluble, very soluble or highly soluble. These solutions are listed in Table 1 and represented in FIG. 5.

Figure 6:
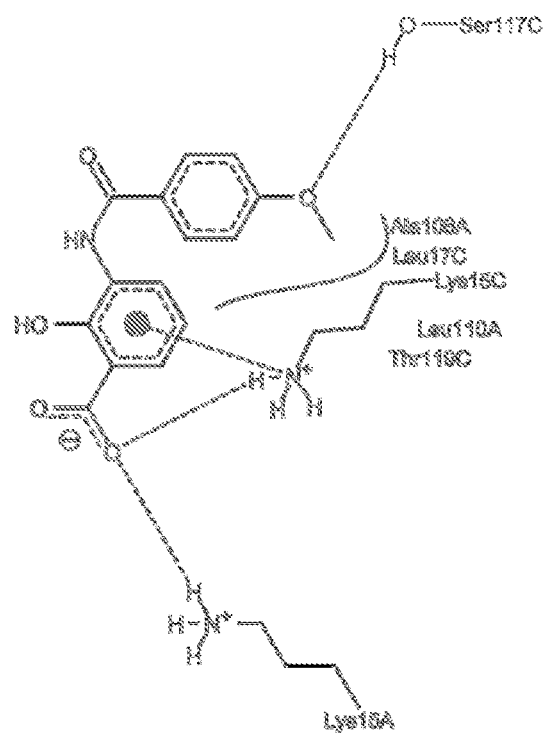
FIG. 6. Predicted interactions between the protein transthyretin (TTR) and compound AT12-A00 (ZINC code 01429477) studied by molecular docking. Dashed lines denote polar interactions such as hydrogen bonds, charge-charge interactions or cation-pi interactions. Grey lines represent non-polar interactions. This figure was generated with PoseView (BioSolveIT).

Visual inspection of compound poses of the top-100 VS solutions upon docking into TTR's T4 binding sites allowed for a structure-based analysis of shape and chemical complementarity of the compounds with the biological target, thus guiding the selection of compounds for biochemical evaluation. Unlike many VS solutions retrieved, compound ZINC01429477 is predicted to engage in a variety of favorable interactions with the receptor's amino acid side chains (FIG. 6): Both Lysine-15 residues seem to establish charge-charge and cation-pi interactions with the compound's benzoic acid moiety, while one Serine-117 residue can hydrogen-bond with the compound's methoxy group. As shown in FIG. 6, other apolar residues in TTR's T4 binding sites like Leucine-17, Alanine-108, Leucine-110 and Threonine-119 seem to contribute to ligand binding via hydrophobic/nonpolar interactions. Furthermore, compound ZINC01429477 passed all filters of physicochemical and pharmacological predictors, showing no violations of Lipinski's rule-of-five for bioavailability [21], an xLogP of 1.57, a polar surface area (PSA) of 98.69 $Å^2$ and a sum of formal charges of 1. The compound is devoid of halogen atoms and predicted "very soluble".

Compound ZINC01429477 was acquired from TimTec LLC, 301 Ruthar Drive, Suite A, Newark, Del. 19711, USA, under catalog code ST4113287 and in the amount of 10 milligrams. Results of activity evaluation are provided in Section G.

TABLE 1

Top-ten virtual screening hits predicted soluble, very or highly soluble and retrieved using a ligand-based VS protocol with Phenox as template. Compound 2-hydroxy-3-[(4-methoxyphenyl)carbonylamino]benzoic acid (ZINC01429477, here labeled AT12-A00) is found at the third position of the (post-screening) filtered set and at the twenty-sixth position of the entire ranked chemical library of 2,259,573 compounds.

| ZINC Code | Ranking within top-100 "soluble" VS hits | Ranking across entire chemical library |
| --- | --- | --- |
| ZINC04638817 | 1 | 5 |
| ZINC02504634 | 2 | 15 |
| ZINC01429477 | 3 | 26 |
| ZINC01753456 | 4 | 35 |
| ZINC01691128 | 5 | 44 |
| ZINC04713400 | 6 | 45 |
| ZINC06726214 | 7 | 46 |
| ZINC05041243 | 8 | 49 |
| ZINC06170657 | 9 | 58 |
| ZINC03873083 | 10 | 72 |

Example 2

Figure 7:
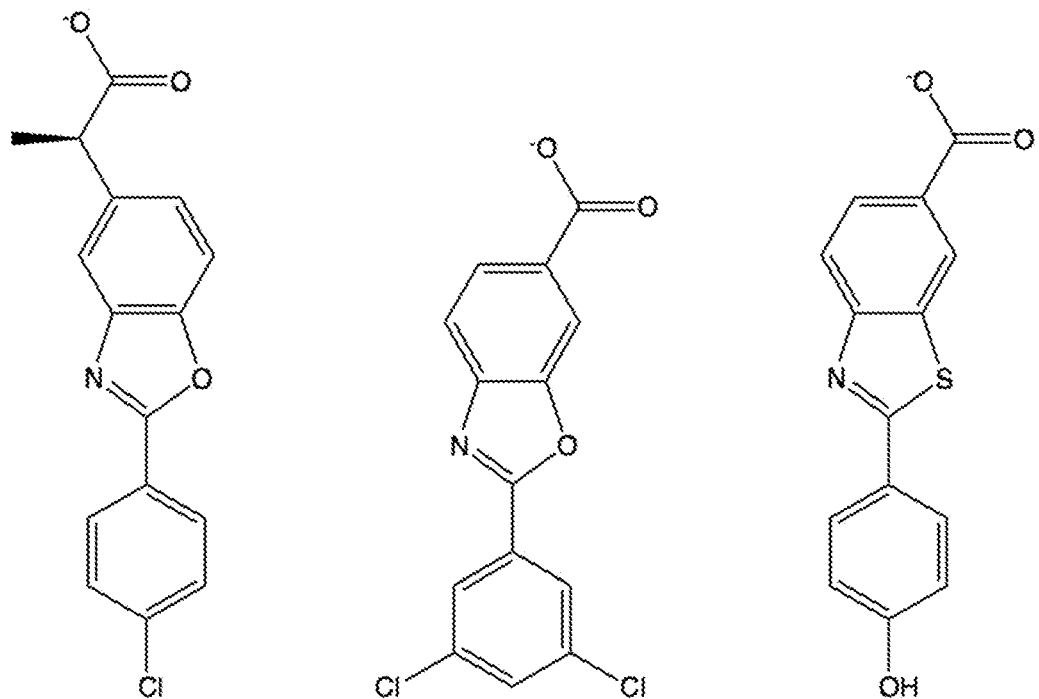
FIG. 7. Chemical formulae of compounds Benoxaprofen, Tafamidis and ZINC00310685. Benoxaprofen is a non-steroidal anti-inflammatory drugs withdrawn from market due to hepatotoxicity and reported cases of fatal cholestatic jaundice. Tafamidis is currently the only drug available for the treatment of familial amyloid polyneuropathy (FAP). ZINC00310685 is an example compound retrieved among the top-100 virtual screening hits (of a chemical library comprising 2,259,573 compounds) employing a ligand-based protocol and the PCX2 query.

Selection of 2-(4-hydroxy-phenyl)-benzothiazole-6-carboxylic Acid for Biochemical Evaluation Prioritization of 2-(4-hydroxy-phenyl)-benzothiazole-6-carboxylic acid (here labeled AT05-A00) for biochemical evaluation of inhibitory activity against amyloid formation by transthyretin (TTR) followed the application of another ligand-based virtual screening (VS) protocol described in reference [20]. A virtual chemical library containing 2,259,573 small organic molecules (described in the Materials and Methods section) was screened against compound PCX2, a template query represented in FIG. 4 and described in the Materials and Methods section. Remarkably, the application of this VS protocol allowed for the identification of a compound with a high level of structural similarity to Tafamidis. AT05-A00 (see FIG. 7) was identified with ZINC code 00310685 and ranked among the top hundred hits—more precisely at position 97. This position falls within the top 0.004% of the ranked chemical library, meaning it is reasonable to regard compound ZINC00310685 as clear suggestion of the applied virtual screening protocol—as opposed to "educated guessing". However, given the high similarity of compound ZINC00310685 with Tafamidis, it was selected for biochemical evaluation for protocol validation purposes only. It was acquired from TimTec LLC, 301 Ruthar Drive, Suite A, Newark, Del. 19711, USA, under catalog code ST082336 and in the amount of 10 milligrams. Results of activity evaluation are provided in Section G.

Example 3

Characterization and Optimization of N-Substituted Arylidenerhodanines
Mode of Action The virtual screening hits presented herein, namely compounds with codes AT50-A00, AT50-B00 and AT50-C00, were discovered using ligand-based virtual screening methodologies that take one or more reference (previously known) ligands and measure similarities in shape, chemistry and/or electrostatics within virtual libraries enriched with drug-like compounds. Because the reference compounds used in this work (represented in FIG. 4) are known TTR stabilizers acting through binding to the same TTR sites explored by the thyroid hormone (T4), it is reasonable to expect that the discovered screening hits, and subsequent optimization derivatives, also exert their stabilizing activity via binding to T4 binding sites.

As revealed in the "Evaluation of the Activity of the Compounds" section, compound AT50-A00 was subjected to an experimental assay based on T4 competition and gel electrophoresis. The results of this experiment showed that AT50-A00 competes with T4, thus supporting our prediction of a mode of action (MoA) based on binding to TTR's T4 binding sites.

While X-ray crystallography will provide additional verification of the MoA of AT50 compounds, at present we resort to structure-based molecular modeling techniques to further support our predictions and also obtain a picture of putative binding modes at the atomic level. All virtual screening hits and respective optimization derivatives (resulting from chemical synthesis) were docked into TTR's T4 binding sites, making use of selected X-ray derived three-dimensional TTR structures deposited in the Protein Data Bank. A description of the utilized TTR structures and molecular docking methodologies is given in reference [20], which reports the results of several re-docking and cross-docking experiments with more than 20 X-ray structures of TTR complexes.

Figure 8A:
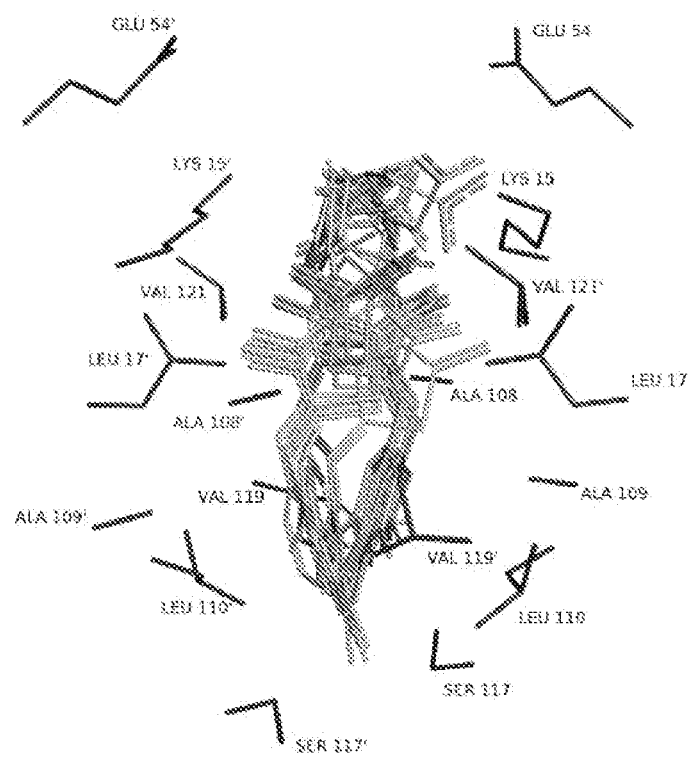
FIGS. 8A to 8B. Predicted docking poses for the Z stereoisomeric forms of the N-substituted arylidenerhodanines belonging to the AT50 series (grey stick representation). TTR's thyroxine binding site is represented by the side-chains of residues (darker sticks) that are known to interact with TTR stabilizers: top view (FIG. 8A) and side view (FIG. 8B) of the binding site.
Figure 8B:
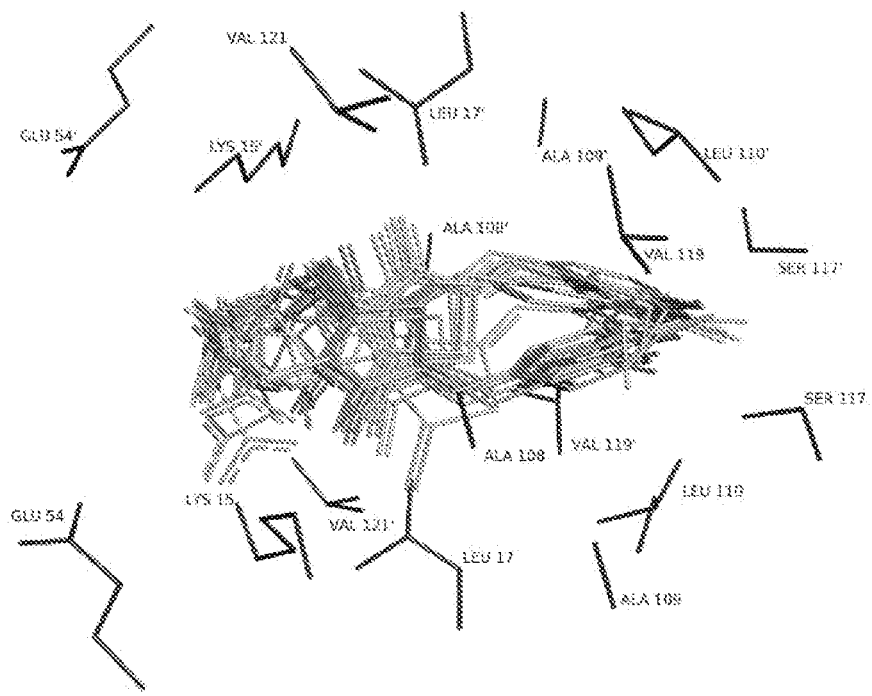

FIGS. 8A to 8B show the best predicted poses for the representative examples of the AT50 series disclosed herein, suggesting that the compounds neatly bind to thyroxine-binding sites of TTR. All poses depict the substituted benzene ring bound at the internal part of TTR binding sites, while the rhodanine ring is positioned at the external part of the sites. The N-attached hydroxycarbonyl or dihydroxycarbonyl alkyl groups "strategically" cover the wide "mouth" of TTR sites, while presenting sufficient flexibly for interaction with one or the two Lysine-15 residues belonging to the adjacent TTR domains. It is also clear that the compounds are allowed to bind in two alternative conformations (due to the C2 symmetry of T4 binding sites), while retaining the orientation of the key pharmacophoric features responsible for their affinity. Similar behavior has been experimentally observed in X-ray crystals of known TTR ligands, such as flufenamic acid (PDB entry 1BM7) [22].

AT50 series expansion and preliminary ligand optimization was driven by structure-based strategies, making use of our knowledge on TTR's structure and pharmacophore in attempt to maximize (specific) polar interactions and shape complementarity between the compounds and the protein. Lead series expansion was accompanied by application of several cheminformatics analyses in order to prioritize for chemical synthesis only compounds retaining drug-like properties, which are essential for bioavailability, metabolic and chemical stability, and safety.

TTR-Compound Interactions and Rationale Behind Optimization

Three virtual screening hits—AT50-A00, AT50-B00 and AT50-C00—were confirmed capable of inhibiting amyloid fibril formation by TTR, showing in vitro activity superior to that of reference compounds Tafamidis (all three hits) and, in one case (AT50-A00), the endogenous TTR binder thyroxine (T4). The results of in vitro evaluation of the compounds are presented in Table 2 and Table 3 ("Evaluation of the Activity of the Compounds" section). Compound AT50-A00 was selected for further evaluation of activity via a T4 binding competition assay, using radio-labeled T4, and an ex vivo assay based on isoelectric focusing (IEF) of plasma TTR—aimed at assessing the compound's ability to stabilize the tetrameric form of human TTR. The results of these assays are presented and discussed in detail in the "Evaluation of the Activity of the Compounds" section. The results confirmed the superior activity of the original virtual screening hit AT50-A00 detected through the fast, in vitro fibril formation assay, suggesting the utilization of the latter as an appropriate means to screening the activity of optimization analogues to be proposed.

Several modifications for all three virtual screening hits were proposed, resulting in a large series of compounds to be studied and tested in silico. Affinity for TTR and for other putative targets (selectivity), physicochemical properties, metabolic and chemical stability, and toxicity represent some of the key parameters that were considered to trim down the series of compounds to be prioritized for chemical synthesis. Disclosed in this document are some of the compounds holding the most balance profiles and that were shown to hold superior activity towards inhibition of TTR fibril formation compared with key reference compounds—namely thyroxine (T4), 2OH-PCB80 and Tafamidis.

Figure 9A:
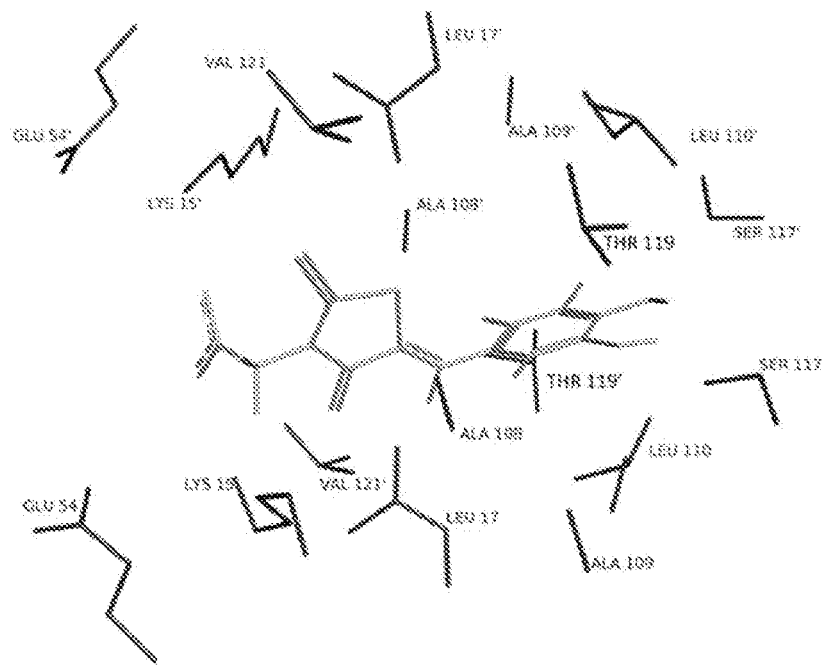
FIGS. 9A to 9C. Predicted docking pose for compound AT50-A01. In the top panels, TTR's thyroxine binding site is represented by the side-chains of residues (darker sticks) that are known to interact with TTR stabilizers: top view (FIG. 9A) and side view (FIG. 9B) of the binding site holding the docked compound. In the bottom panels (FIG. 9C), TTR:compound interactions are represented in a 2D diagram generated with the program PoseView.
Figure 9B:
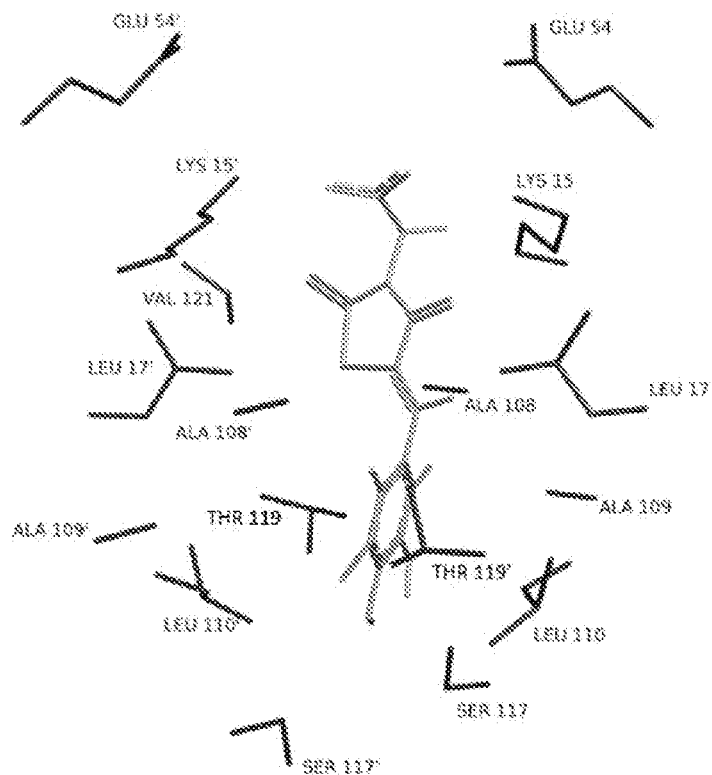
Figure 9C:
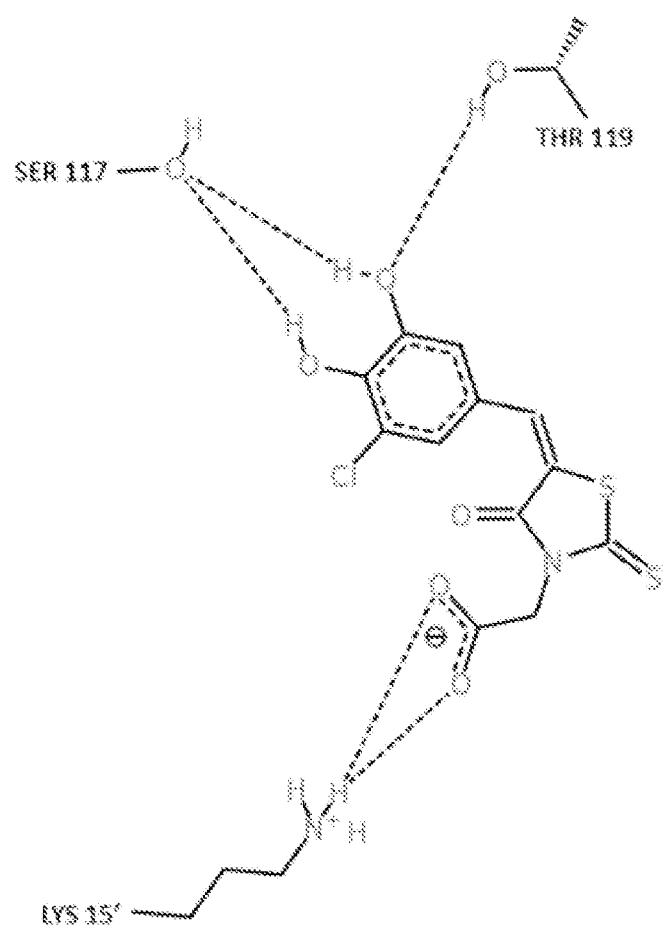
Figure 10A:
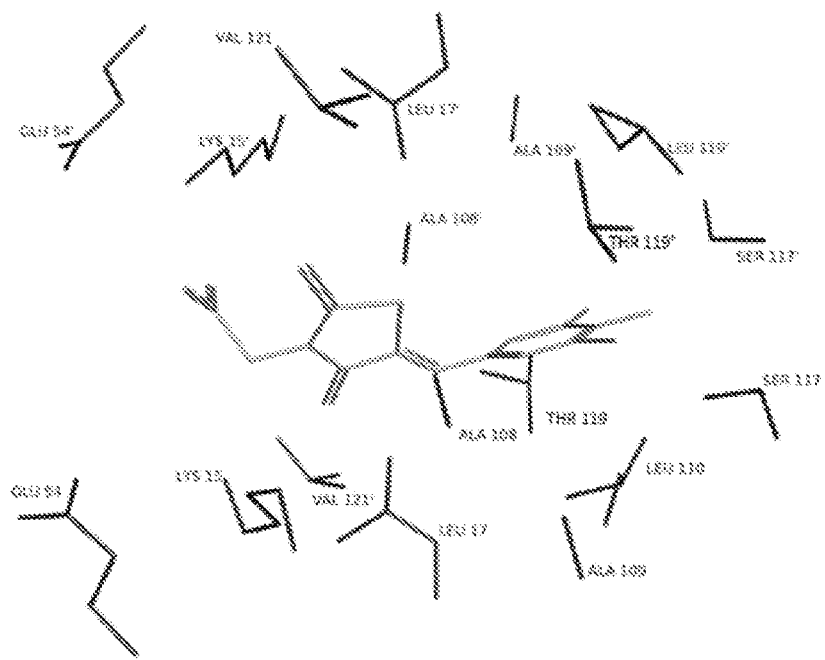
FIGS. 10A to 10C. Predicted docking pose for compound AT50-A03. In the top panels, TTR's thyroxine binding site is represented by the side-chains of residues (darker sticks) that are known to interact with TTR stabilizers: top view (FIG. 10A) and side view (FIG. 10B) of the binding site holding the docked compound. In the bottom panels (FIG. 10C), TTR:compound interactions are represented in a 2D diagram generated with the program PoseView.
Figure 10B:
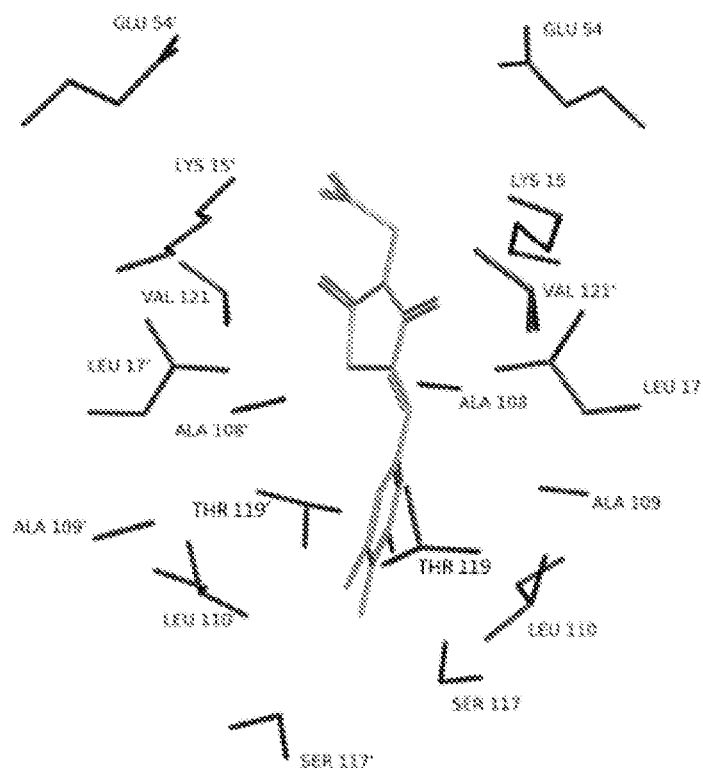
Figure 10C:
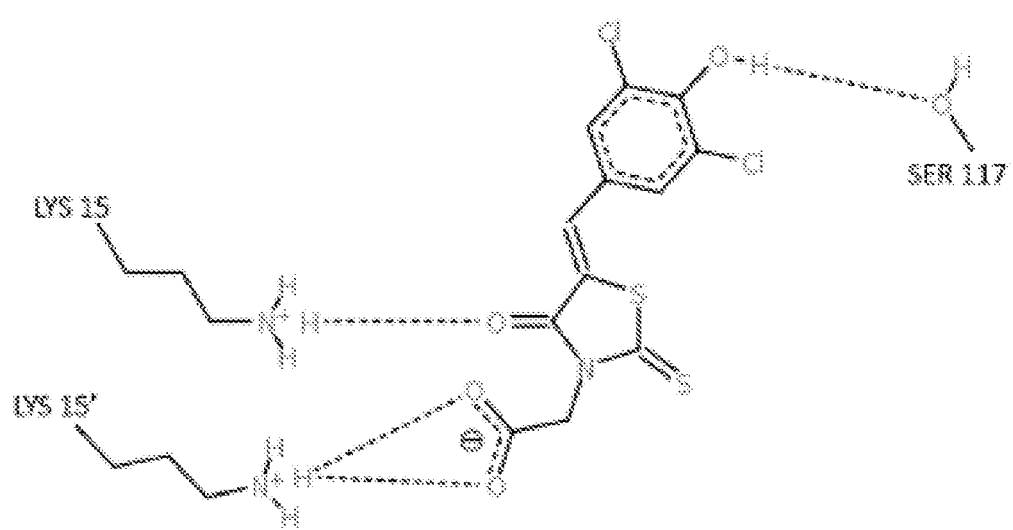

Compound AT50-A01 illustrates one first optimization derivative of compound AT50-A00 wherein the methoxy group attached at the meta position of the benzene ring is replaced by an hydroxyl group. This substitution renders compound AT50-A01 less bulky than the original hit, while retaining the ability to favorably interact with TTR's Serine-117 and Threonine-119 residues (FIGS. 9A to 9C), resulting in a significant increase in activity (see Table 2 and Table 3 in "Evaluation of the Activity of the Compounds"). Compound AT50-A03 results from an attempt of exploring the inner halogen binding pockets of TTR's T4 binding site, wherein a second chlorine atom replaces the methoxy group present in compound AT50-A00 (FIGS. 10A to 10C). This substitution has also resulted in a highly active analogue (AT50-A03; see Table 2 and Table 3).

Figure 11A:
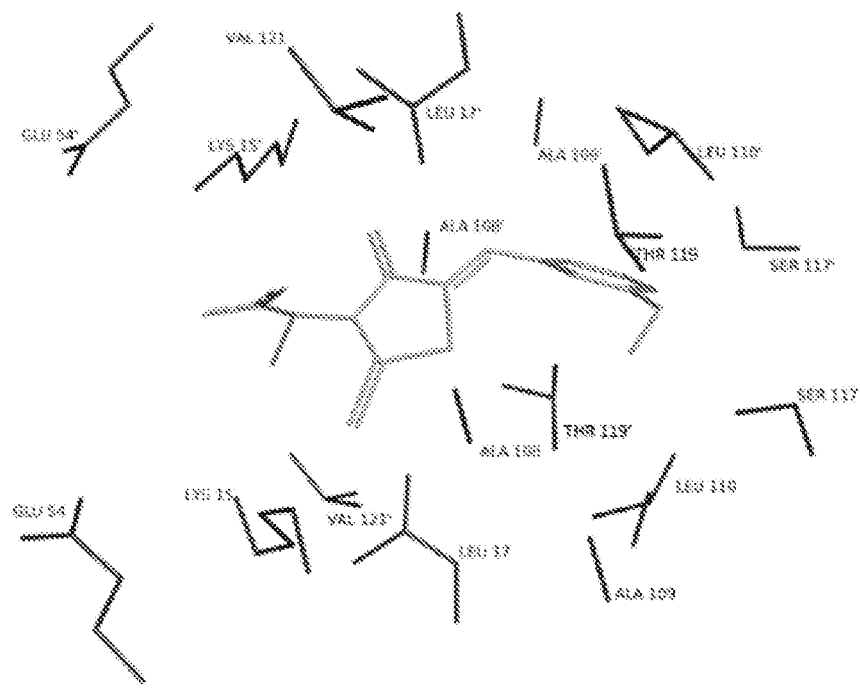
FIGS. 11A to 11C. Predicted docking pose for compound AT50-B00. In the top panels, TTR's thyroxine binding site is represented by the side-chains of residues (darker sticks) that are known to interact with TTR stabilizers: top view (FIG. 11A) and side view (FIG. 11B) of the binding site holding the docked compound. In the bottom panels (FIG. 11C), TTR:compound interactions are represented in a 2D diagram generated with the program PoseView.
Figure 11B:
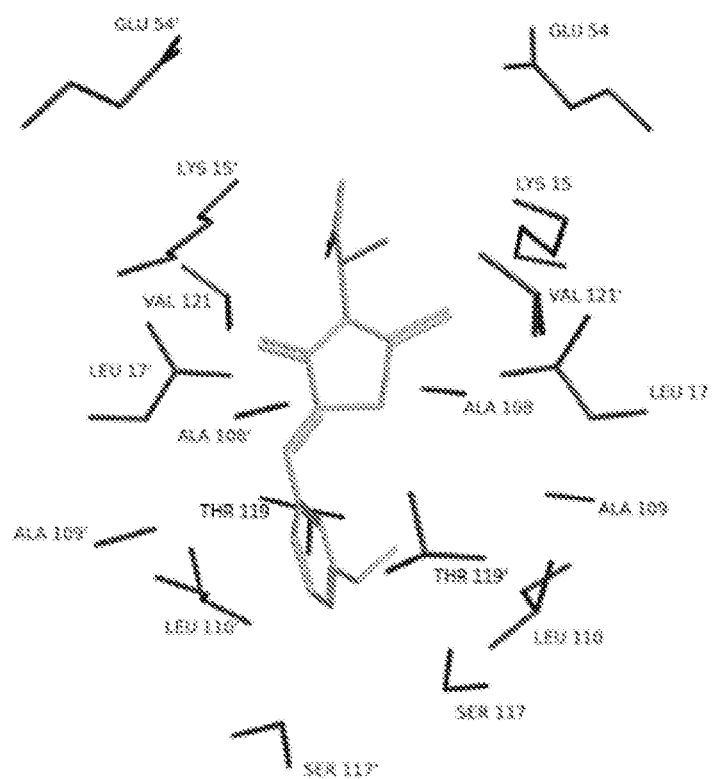
Figure 11C:
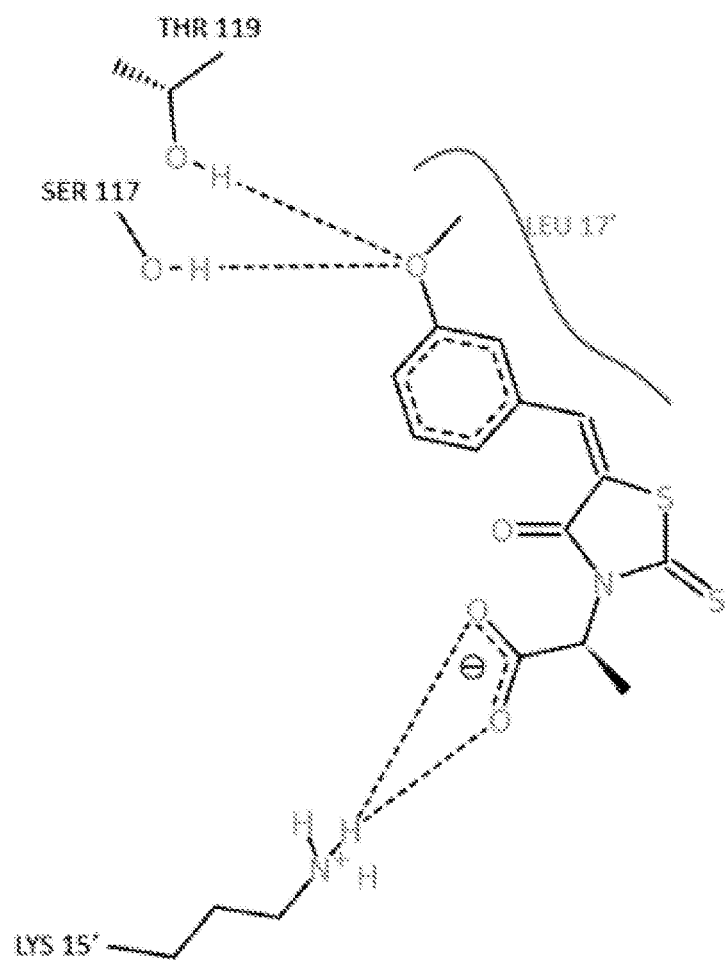

Even though the virtual screening hits AT50-B00 and AT50-C00 appear to lack a favorable set of substituents to the benzene ring of the scaffold, both compounds display promising inhibitory activity. This shifted the focus of our optimization efforts to the substitution of the rhodanine ring positioned at the external part of TTR's T4 binding sites. In these compounds, the presence of a hydroxycarbonyl establishes a strong charge-charge interaction with one or two of TTR's Lysine-15 residues (see FIGS. 11A to 11C). However, the positioning of Lys-15 side-chains at the entrance of TTR's T4 binding site, in rapid interactions with the highly-mobile solvent molecules, results in a higher, localized structural flexibility—a notion sustained by the higher thermal factors of the X-ray crystal structures of TTR and atomic-level studies based on Molecular Dynamics simulations (data not shown). This led us to hypothesize that the use of longer, bulkier "tails" attached to the nitrogen atom of the rhodanine ring could compensate for that extra flexibility and stabilize the protein-ligand complex. Furthermore, our modeling studies based on the docking of compounds into putative targets of thyroxine- and NSAID-like molecules (including thyroxine-binding globulin, thyroid hormone receptors and the cyclooxygenases) led us to think that such "tails" could also have a beneficial effect on the selectivity of compounds for TTR. Therefore, several "tails" of different sizes were proposed, synthesized and tested.

Figure 12A:
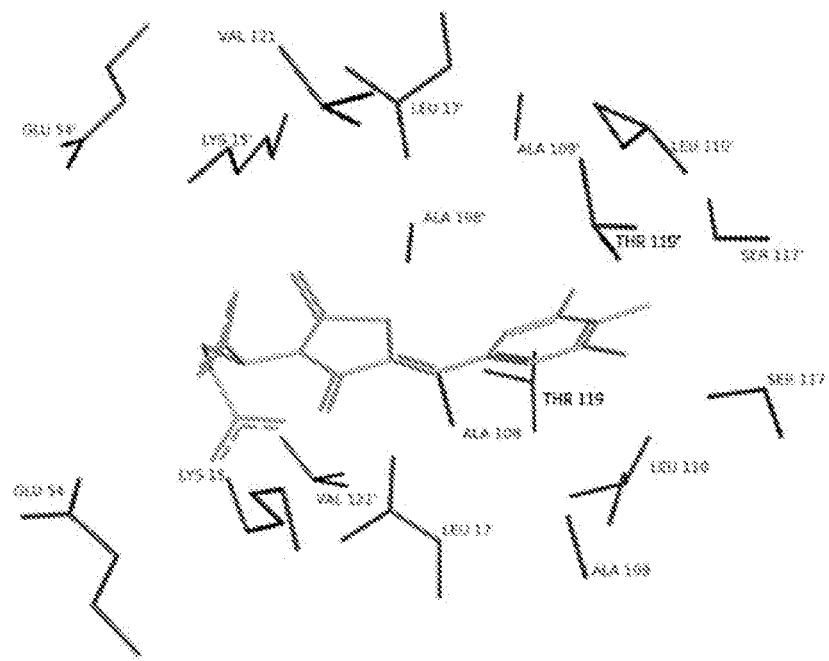
FIGS. 12A to 12C. Predicted docking pose for compound AT50-C02. In the top panels, TTR's thyroxine binding site is represented by the side-chains of residues (darker sticks) that are known to interact with TTR stabilizers: top view (FIG. 12A) and side view (FIG. 12B) of the binding site holding the docked compound. In the bottom panels (FIG. 12C), TTR:compound interactions are represented in a 2D diagram generated with the program PoseView.
Figure 12B:
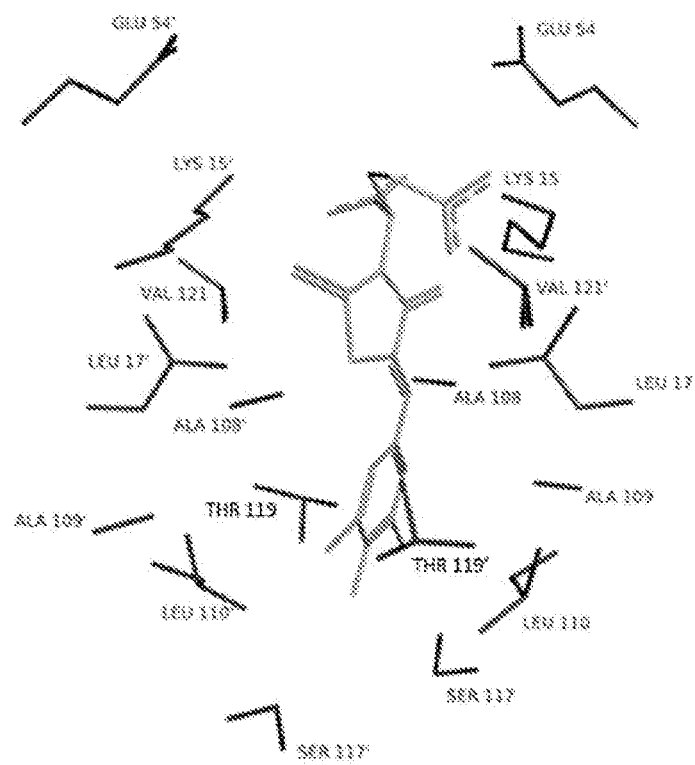
Figure 12C:
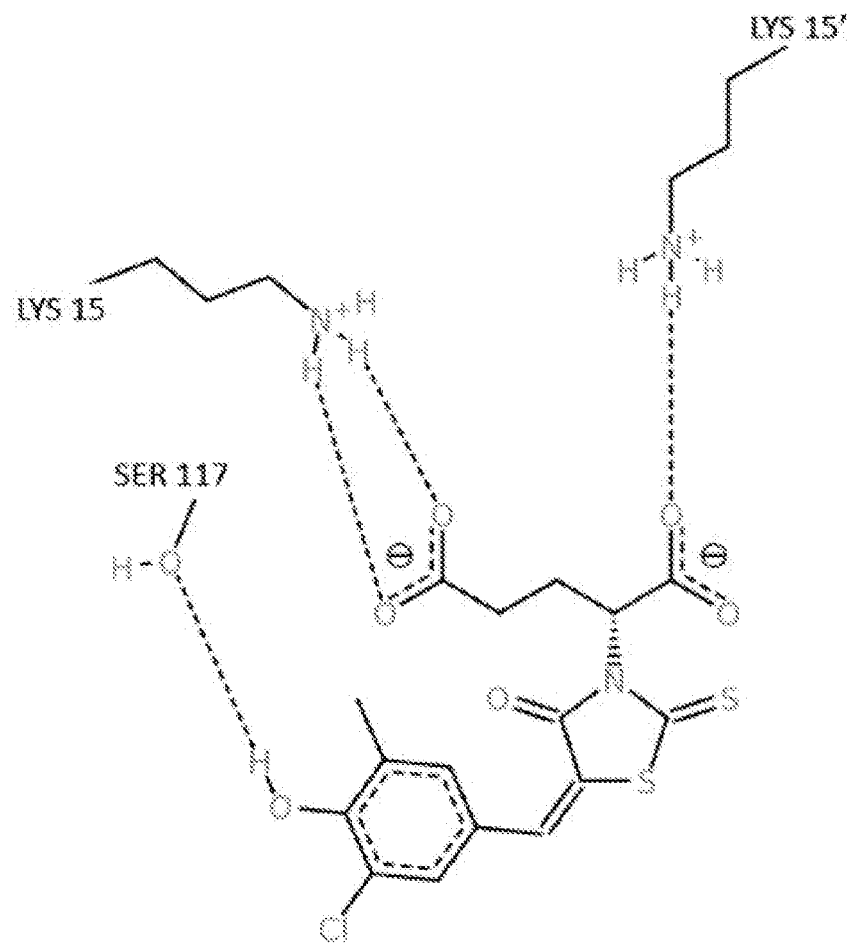
Figure 13A:
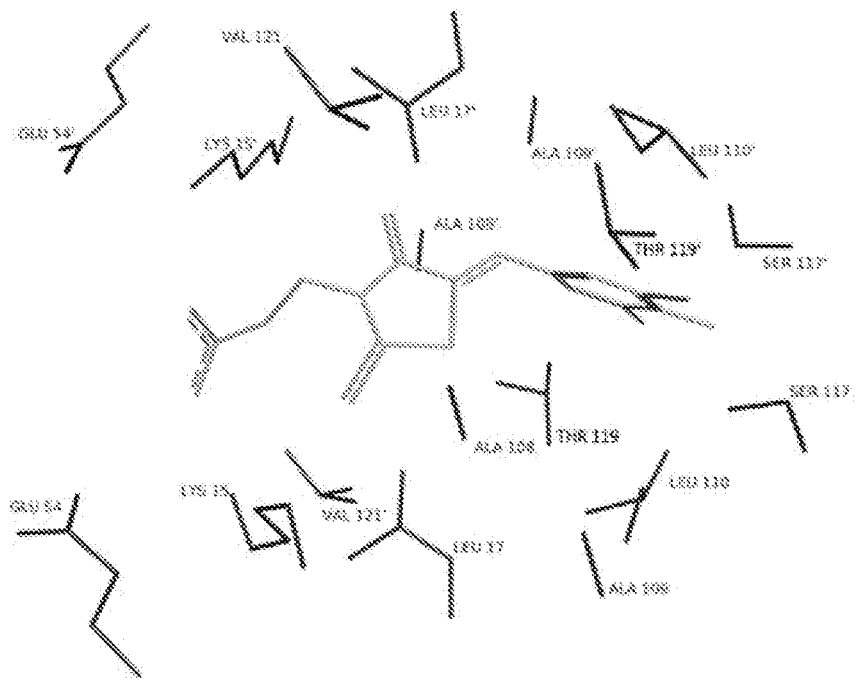
FIGS. 13A to 13C. Predicted docking pose for compound AT50-C15. In the top panels, TTR's thyroxine binding site is represented by the side-chains of residues (darker sticks) that are known to interact with TTR stabilizers: top view (FIG. 13A) and side view (FIG. 13B) of the binding site holding the docked compound. In the bottom panels (FIG. 13C), TTR:compound interactions are represented in a 2D diagram generated with the program PoseView.
Figure 13B:
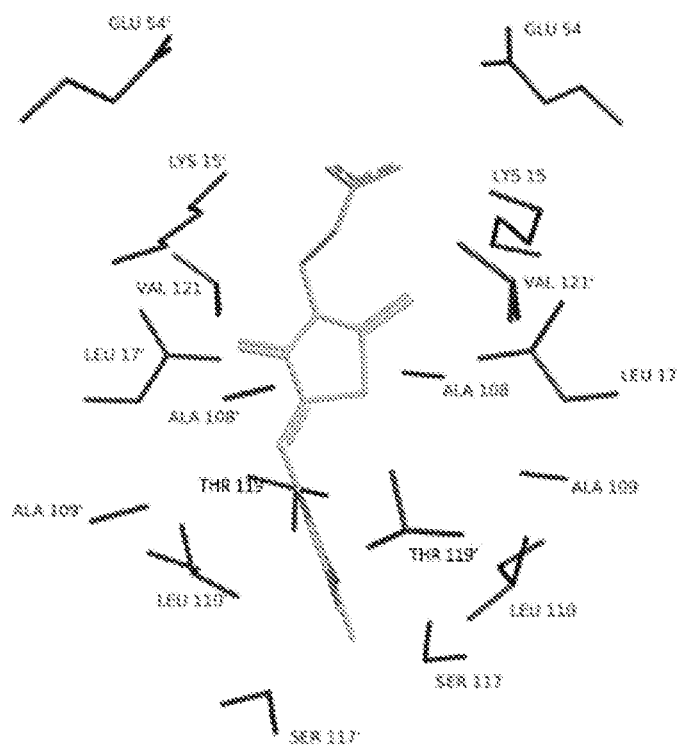
Figure 13C:
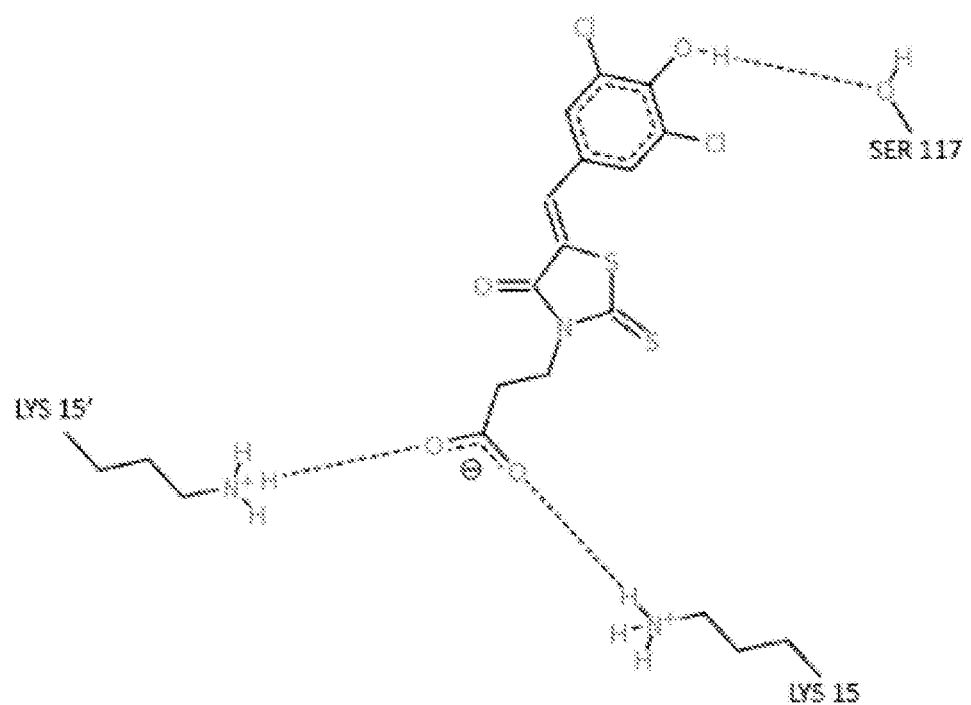

Compounds AT50-C02 (FIGS. 12A to 12C) and AT50-C15 (FIGS. 13A to 13C) represent the most successful examples of dihydroxycarbonyl-alkyl and hydroxycarbonyl-alkyl substituents to the N atom of the rhodanine ring, respectively, with the latter (AT50-C15) corresponding to one of the strongest TTR-amyloid inhibitors identified to date.

Activity of E Stereoisomers

TTR is biologically active as a homotetramer displaying 2,2,2 molecular symmetry and features two equivalent, C2-symmetric, thyroxine binding sites that extend across the center of the protein. The fact that these two binding sites display two-fold symmetry led us to hypothesize that, besides the Z stereoisomeric form of the compounds presented herein, the corresponding E stereoisomers could also strongly bind TTR's thyroxine binding sites and thus stabilize the protein. This hypothesis was tested by 1) performing molecular docking of both Z and E stereoisomers of each compound belonging to the AT50 series into the binding sites of TTR (using selected X-ray derived structures deposited in the Protein Data Bank), and 2) acquiring and experimentally testing the commercially-available E stereoisomer of the original virtual screening hit, AT50-A00 (results are discussed in more detail in section "Evaluation of the Activity of the Compounds").

Figure 14A:
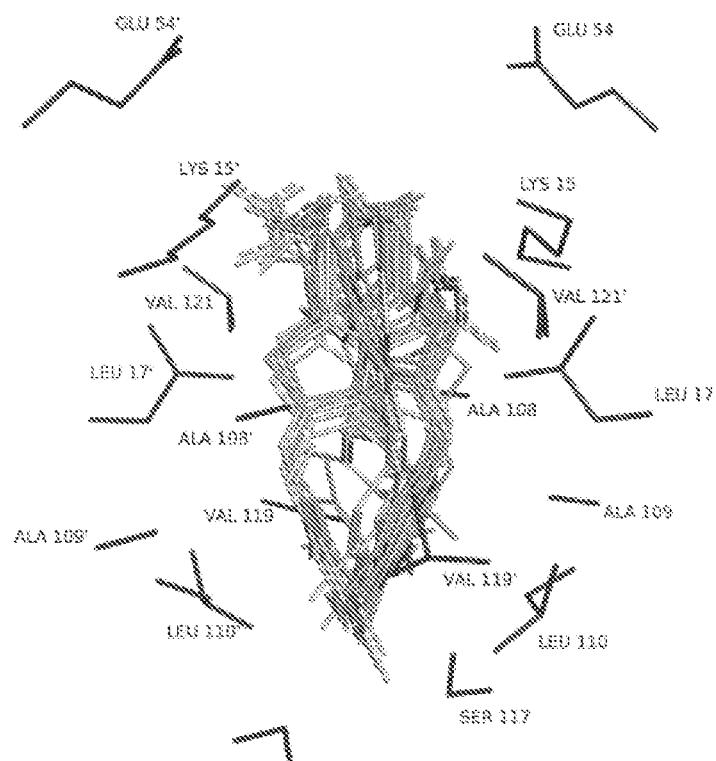
FIGS. 14A to 14B. Predicted docking poses for the E stereoisomeric forms of the N-substituted arylidenerhodanines belonging to the AT50 series (grey stick representation). TTR's thyroxine binding site is represented by the side-chains of residues (darker sticks) that are known to interact with TTR stabilizers: top view (FIG. 14A) and side view (FIG. 14B).
Figure 14B:
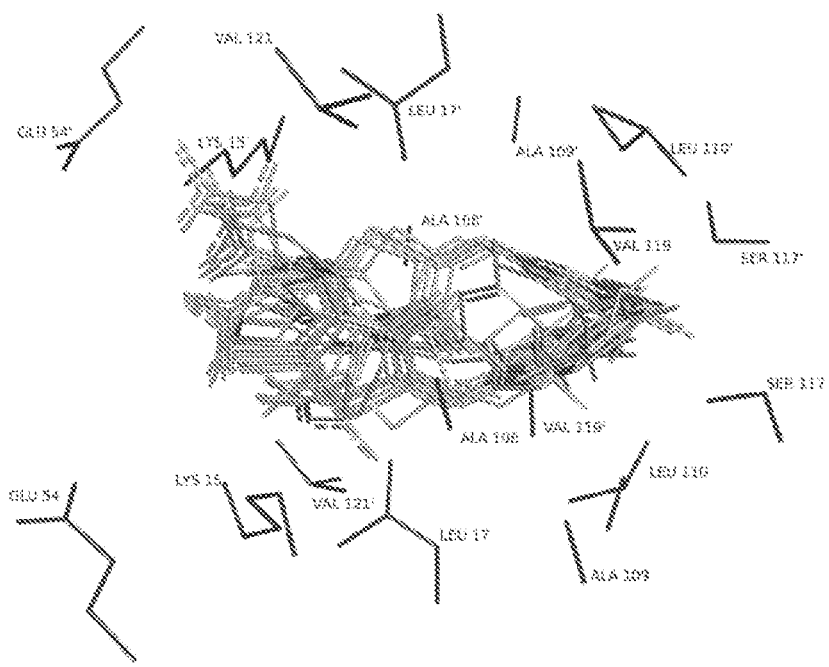
Figure 15A:
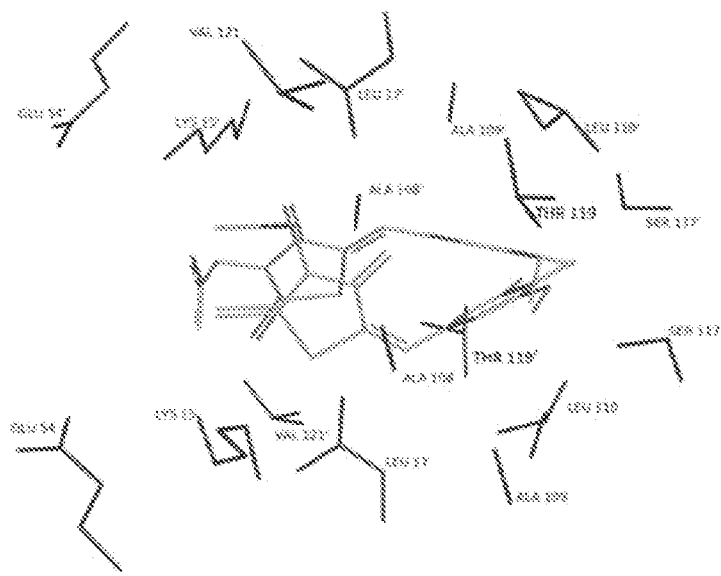
Figure 15B:
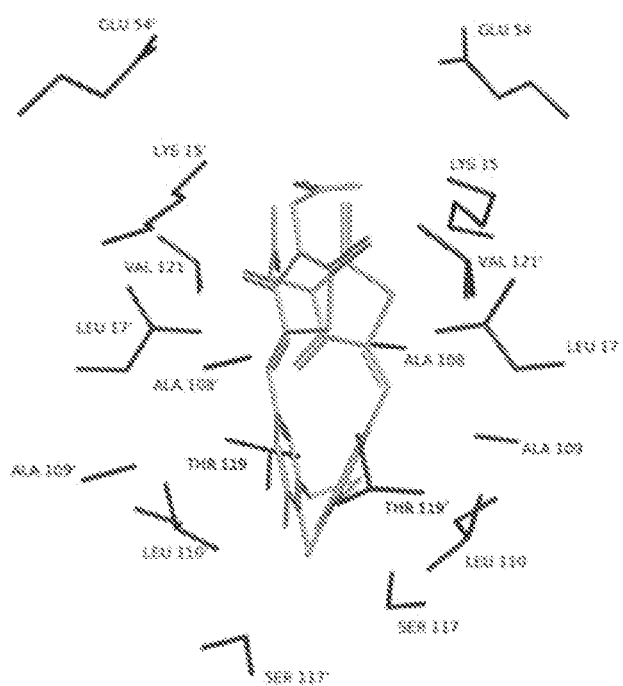
Figure 16:
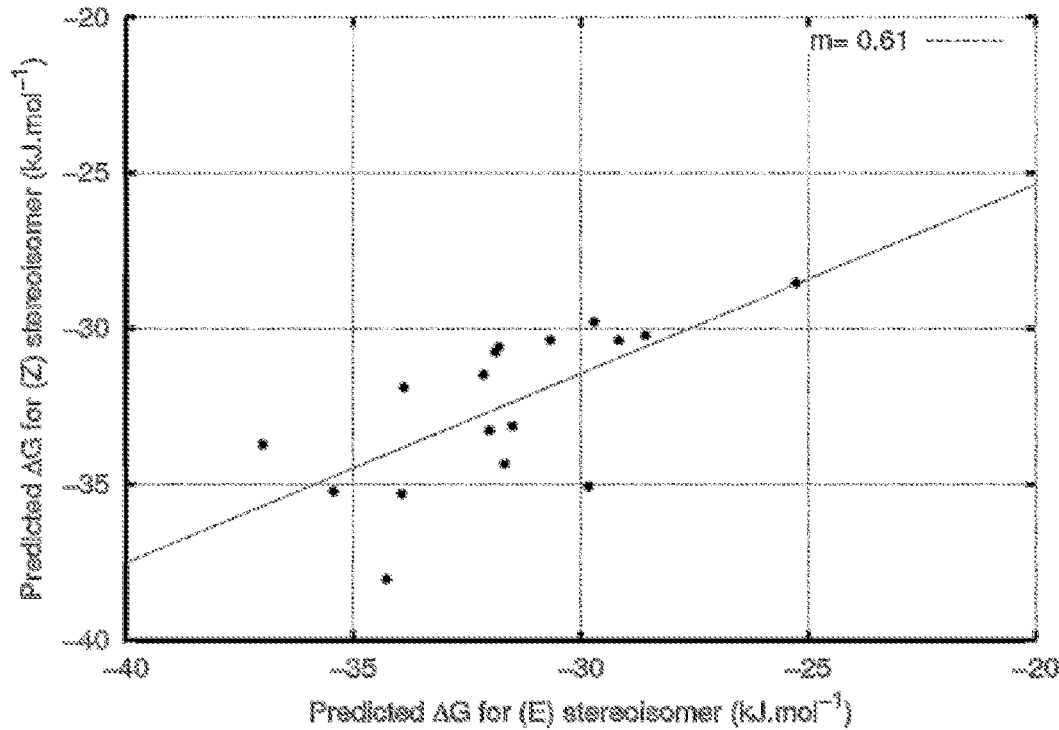
FIG. 16. Estimated free energy of binding (AG) for E and Z stereoisomers of seventeen compounds belonging to the AT50 series. The slope of the fit line (m=0.61) indicates a positive correlation between binding affinities of the stereoisomers. AG values were predicted using molecular docking.

FIGS. 14A to 14B show the best predicted poses obtained by molecular docking for the E stereoisomers of AT50 compounds on the thyroxine-binding sites of TTR, disclosing a bind mode that is analogous to the one predicted for the corresponding Z stereoisomers (compare with FIGS. 8A to 8B). Once more, all poses depict the substituted benzene ring bound at the internal part of TTR binding sites, while the rhodanine ring is positioned at the external part of the sites, with the hydroxycarbonyl and dihydroxycarbonyl alkyl groups attached to the rhodanine ring ideally placed at the entrance of TTR T4 sites. As observed in the docking experiments with the corresponding Z stereoisomers, the compounds are allowed to interact with T4 binding sites in two alternative/symmetrical conformations, while preserving their critical orientation within the sites.

The propensity for interaction of E stereoisomers of AT50 compounds was further studied by comparing binding free energies predicted by molecular docking scoring functions for both E and Z stereoisomeric forms (as illustrated in FIG.

16). Despite the poor performance of docking scoring functions at predicting experimentally-determined ligand affinities, in this study we use the same basis reference, both theoretical in nature and estimated using the exact same methodology, which seems an acceptable approach to drawing the comparison. The results show there is a positive correlation between the estimated free energies of binding for the E and Z stereoisomers, denoted by the positive slope of the fit line (0.61), which is line with the equivalent interactions predicted for the E and Z stereoisomers (FIGS. 15A to 15D provide an adequate illustration based on compound AT50-A00).

The experimental evaluation of the in vitro activity of the E stereoisomer of the original virtual screening hit, AT50-A00 (as discussed in section "Evaluation of the Activity of the Compounds"), confirmed the non-stereoselective nature of the association between AT50 compounds and the protein TTR (see FIGS. 15A to 15D), emphasizing the utility of both E and Z stereoisomers as TTR stabilizers.

Evaluation of the Activity of the Compounds

The activity of compounds towards the inhibition of amyloid fibril formation by transthyretin (TTR) may be assessed by several biochemical assays. Within the context of this work, the term "activity" denotes one compound's ability to bind to TTR, stabilize the native tetrameric form of the protein and thus prevent the formation of amyloid fibrils. Amongst the available assays reported in the literature are a fibril formation assay, the determination of the three-dimensional structure of a TTR:compound complex by means of X-ray crystallography, and the determination of the stoichiometry and energetics of TTR:compound interactions by isothermal titration calorimetry (ITC).

Some of the characteristics of an effective TTR stabilizer are 1) high affinity for TTR, in order to promote a strong binding and thus stabilization of the protein in plasma, and 2) high selectivity, in order to partition into TTR in the presence of all of the other plasma proteins (namely those that may transport thyroxine-like molecules, including thyroxine-binding globulin and albumin). Therefore, in this work two sets of evaluations, with varying levels of complexity, are used to evaluate the activity and the selectivity of the compounds. These are described briefly here and in greater detail in the "Materials and Methods" section.

The first set of evaluations is based on a fast, stagnant fibril formation assay that is used for the early screening of compounds, be they virtual screening hits or newly synthesized analogues. In this assay, a solution of the compound under test at 1.8, 3.6 or 7.2 µM is added to a solution of TTR at 3.6 µM, so that there is enough compound to bind to either one or both of TTR's binding sites. The pH of the resulting solution is then lowered to 4.4 to promote amyloidogenesis. The process of amyloid fibril formation over time is assessed by turbidimetry measurements at three different wavelengths (405, 450 and 490 nm, or at 550, 600 and 650 nm when the compound absorbs light at the previous wavelengths), using a spectrophotometer endowed with a BioTek microplate reader. The extent of fibril formation of each mixture is determined by normalizing a sample with the protein (TTR), in absence of compounds, which, at the end of 72 hours, represents 100% of amyloid fibril formation. In each experiment, each compound concentration is tested in triplicate. For each compound concentration and incubation time, the arithmetic mean of the triplicate experiments is calculated, as well as the arithmetic mean of the three measured wavelengths. High activity can be defined as a percentage of fibril formation below 10% at compound concentration 7.2 µM (TTR:compound stoichiometry 1:2) and below 40% at 3.6 µM (TTR:compound stoichiometry 1:1).

Compound concentrations inhibiting TTR amyloid fibril formation by 50% ($IC_{50}$ values) were determined for confirmed screening hits and successful optimization derivatives, by monitoring the effect of increasing concentrations of the compounds on the inhibition values. Ten different compound concentrations were used for each $IC_{50}$ assay, along with a fixed TTR concentration (3.6 µM).

The second set of evaluations, involving assays of higher complexity/cost, is meant to evaluate both the activity and selectivity (versus other plasma proteins) of selected compounds. At the moment, these assays have been applied only to one confirmed virtual screening hit, labeled AT50-A00, in order to define a basis level prior to lead series expansion and optimization. Tafamidis was used as the main reference compound. One assay is based on binding competition with thyroxine (T4) for TTR and is performed by T4 binding gel electrophoresis as described in reference [23]. Briefly, upon incubation of human plasma in the presence of the test compounds and radio-labeled T4 ([125I]T4), the samples are subjected to native PAGE. After electrophoresis, the gels are dried, subjected to phosphor imaging, and the intensity of the protein bands is then compared. Two or three bands of different intensity should be visualized in plasma samples, corresponding to the major T4-binding plasma proteins, namely albumin (ALB), transthyretin (TTR) and thyroxine-binding globulin (TBG). The intensity of the bands decreases, as compared to the control samples (absence of compound), if the compound binds to the protein(s) competing with T4.

In another assay, TTR stability is assessed by isoelectric focusing (IEF) of plasma TTR as described in references [23,24] and in further detail in the "Evaluation of tetrameric TTR stability by IEF" subsection of the "Materials and Methods" section. To perform the assay, 30 µL of human plasma are incubated with 5 µL of a 10 mM solution of test compounds and control compounds overnight at 4° C. followed by a 1 hour incubation at room temperature. The preparations are subjected to native PAGE. The gel band containing TTR is then excised and applied to an IEF gel and IEF is carried out in semi-denaturing conditions. Proteins are stained with Coomassie Blue, the gels are scanned and subjected to densitometry. The results are expressed as the ratio of TTR tetramer over the total TTR species present, reflecting TTR stability.

In Vitro Inhibition of Transthyretin Amyloid Fibril Formation

The in vitro activity of the compounds was assessed through a biochemical assay based on turbidimetry measurements, in which fibril formation is induced by acidification of the solution to pH 4.4 after incubation with the hit compound to be tested. The amount of amyloid fibrils formed is then monitored throughout 72 hours. Further details on this assay are provided in the "Evaluation of amyloid inhibition in vitro" subsection in "Materials and Methods".

Figure 17:
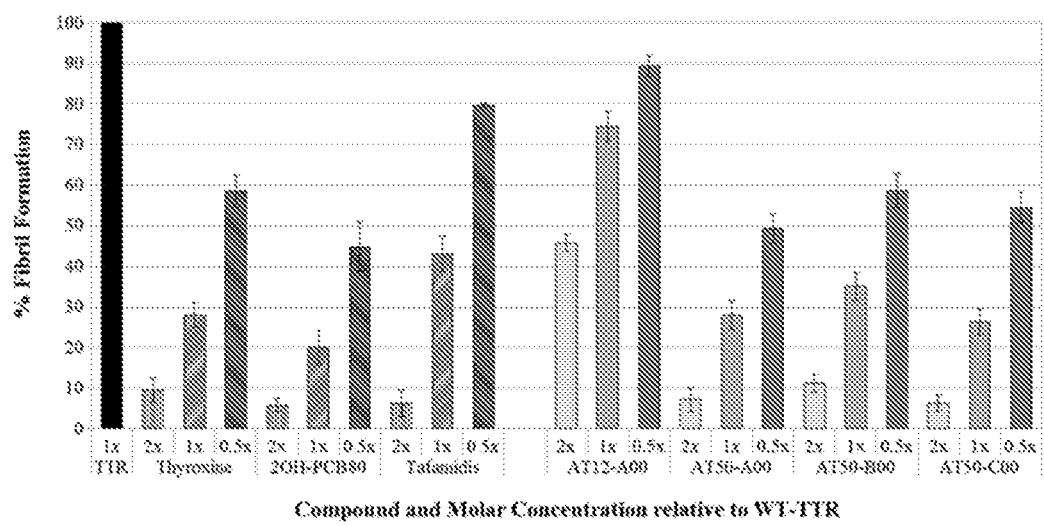
FIG. 17. In vitro activity of three reference transthyretin (TTR) stabilizers and four virtual screening (VS) hits against amyloid fibril formation, at three distinct stoichiometries of compound versus wild type TTR (WT-TTR)—2:1 (2×), 1:1 (1×) and 1:2 (0.5×). In this assay, fibril formation of TTR at 3.6 μM concentration is induced by acidification of the solution to pH 4.4 in the presence of a stabilizer compound. The amount of amyloid fibrils formed is monitored over 72 hours by turbidimetry measurements taken at 405 nm, 450 nm and 490 nm (or at 550 nm, 600 nm and 650 nm when the compound absorbs light at the previous wavelengths), and at 37° C. All values are normalized to the negative control (black bar), i.e. 100% of fibril formation, which in turn corresponds to the amount of formed TTR fibrils quantified after 72 hours of incubation in absence of compound. Here, three reference compounds are contrasted with four virtual screening hits. On the left, the reference compounds thyroxine (T4), 2OH-PCB80 and Tafamidis are shown. On the right, the inhibitory activities of compounds AT12-A00, AT50-A00, AT50-B00 and AT50-C00, all identified by virtual screening, are shown. The error bars correspond to standard deviations.

FIG. 17 summarizes the results of the in vitro evaluation of the activity of four virtual screening hits presented herein towards the inhibition of amyloid fibril formation by TTR. The results are contrasted with three reference compounds, including thyroxine (the endogenous TTR binder), 2OH-PCB80 (one of the strongest TTR amyloid inhibitor identified to date) and Tafamidis (the first and only drug treatment for FAP). All three virtual screening hits belonging to the AT50 series display inhibitory activity superior to Tafamidis, comparable to thyroxine, yet inferior to 2OH-PCB80. Remarkably, even at lower compound concentrations (1:2 compound-protein stoichiometry), AT50 hits produced high inhibition of fibril formation; AT50-A00, in particular, produced an inhibition above 70%. These results underlie the decision to conduct further experimental evaluation with AT50-A00 compounds and to enrich the AT50 compound series with optimized derivatives.

Figure 18:
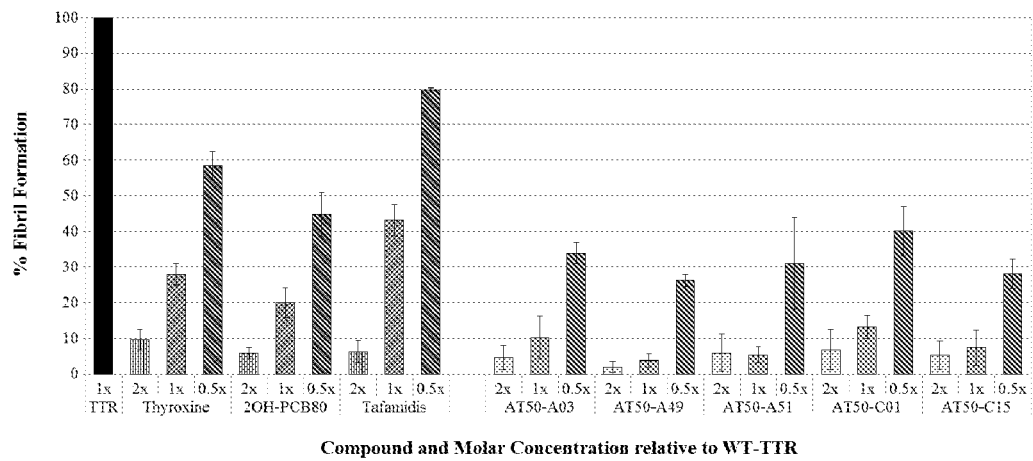
FIG. 18. In vitro activity of three reference transthyretin (TTR) stabilizers and five AT50 compounds against amyloid fibril formation, at three distinct stoichiometries of compound versus TTR—2:1 (2×), 1:1 (1×) and 1:2 (0.5×). In this assay, fibril formation of TTR at 3.6 μM concentration is induced by acidification of the solution to pH 4.4 in the presence of a stabilizer compound. The amount of amyloid fibrils formed is monitored over 72 hours by turbidimetry measurements taken at 405 nm, 450 nm and 490 nm (or at 550 nm, 600 nm and 650 nm when the compound absorbs light at the previous wavelengths), and at 37° C. All values are normalized to the negative control (black bar), i.e. 100% of fibril formation, which in turn corresponds to the amount of formed TTR fibrils quantified after 72 hours of incubation in absence of compound. Here, three reference compounds are contrasted with five of the most active compounds belonging to the AT50 series. On the left, the reference compounds thyroxine (T4), 2OH-PCB80 and Tafamidis are shown. On the right, the inhibitory activities of the optimized, "short-tailed" analogues AT50-A01, AT50-A03 and AT50-A06, and the "long-tailed" analogues AT50-C02 and AT50-C15 are shown. The error bars correspond to standard deviations.
Figure 19:
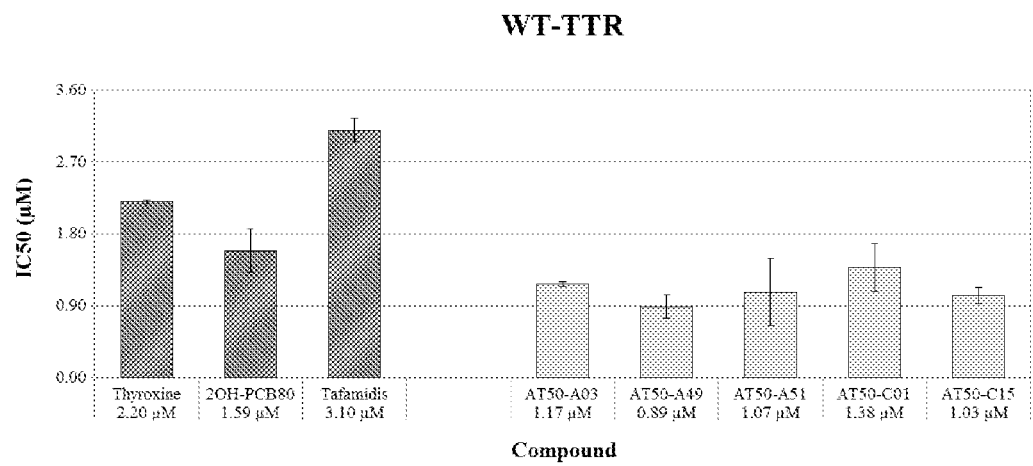
FIG. 19. Concentration of test compounds capable of inhibiting wild type TTR (WT-TTR) amyloid fibril formation by 50% (here denoted by an $IC_{50}$). The values were determined by monitoring the effect of increasing concentrations of the compounds on the inhibition patterns. Ten different compound concentrations were used for each $IC_{50}$ determination, while WT-TTR concentration was kept fix at 3.6 μM. Three reference compounds are contrasted with five of the most active compounds belonging to the AT50 series. On the left, the reference compounds thyroxine (T4), 2OH-PCB80 and Tafamidis are shown. On the right, the $IC_{50}$ values corresponding to the inhibitory activities of optimized, "short-tailed" arylidenerhodanines (AT50-A03) and arylidenethiazolidinediones (AT50-A49 and AT50-51), as well as "long-tailed" arylidenerhodanine analogues (AT50-C01 and AT50-C15) are plotted. When present, the error bars correspond to standard deviations.

FIG. 18 illustrates the results obtained for some of the strongest TTR amyloid inhibitors belonging to the AT50 series and herein described as examples—employing the same biochemical assay that was explored to confirm our virtual screening hits. In general, AT50 compounds offer inhibition profiles equal to or better than Tafamidis and T4. Compound AT50-C15, in particular, display, to the best of our knowledge, unprecedented inhibitory activity against amyloid fibril formation by TTR, superior to that of 2OH-PCB80. FIG. 19 provides a complementary analysis of fibril inhibition based on determination of the concentration of compounds capable of inhibiting TTR amyloid fibril formation by 50% (herein denoted by an "$IC_{50}$"). The values were determined by monitoring the effect of increasing concentrations of the compounds on the inhibition patterns. Ten different compound concentrations were used for each $IC_{50}$ determination, while TTR concentration was kept fix at 3.6 µM.

Table 2 summarizes the results of the in vitro evaluation of the most active compounds belonging to the AT50 series against amyloid fibril formation by wild type TTR, while Table 3 summarizes the results of the most active compounds belonging to the AT50 series against amyloid fibril formation by Val122Ile-TTR.

TABLE 2

| Compound | Structure | WT-TTR amyloid inhibition in vitro | |
|---|---|---|---|
| | | Fibril Formation (%) | $IC_{50}$ (µM) |
| AT50-A00 (Z) | [structure: rhodanine-type core with N-CH₂-CO₂H, C=S, and 5-ylidene-benzyl bearing OCH₃, OH, Cl substituents] | 28 | 1.77 ± 0.24 |
| AT50-A00 (E) | [structure: E-isomer of above] | 26 | 1.73 ± 0.06 |
| AT50-A01 | [structure: with Cl, OH, OH on aryl ring] | 12 | 1.45 ± 0.04 |
| AT50-A03 | [structure: with Cl, OH, Cl on aryl ring] | 10 | 1.17 ± 0.03 |
| AT50-A05 | [structure: with Cl, Cl on aryl ring] | 17 | 1.62 ± 0.13 |

TABLE 2-continued

| Compound | Structure | WT-TTR amyloid inhibition in vitro | |
|---|---|---|---|
| | | Fibril Formation (%) | IC$_{50}$ (μM) |
| AT50-A06 | 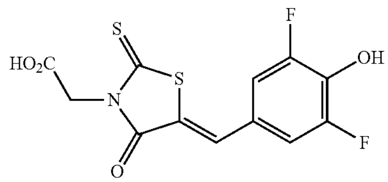 [SMILES: O=C(O)CN1C(=O)/C(=C/c2cc(F)c(O)c(F)c2)SC1=S] | 28 | 1.81 ± 0.40 |
| AT50-A11 | 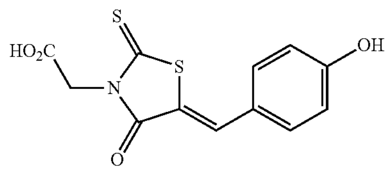 [SMILES: O=C(O)CN1C(=O)/C(=C/c2ccc(O)cc2)SC1=S] | 35 | NA |
| AT50-A12 | 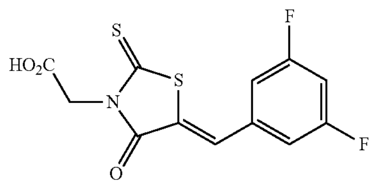 [SMILES: O=C(O)CN1C(=O)/C(=C/c2cc(F)cc(F)c2)SC1=S] | 44 | 2.88 ± 0.24 |
| AT50-A17 | 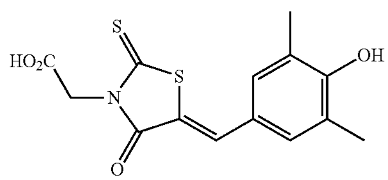 [SMILES: Cc1cc(/C=C2\SC(=S)N(CC(=O)O)C2=O)cc(C)c1O] | 27 | 2.37 ± 0.47 |
| AT50-A35 | 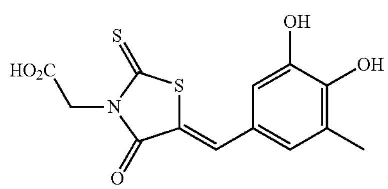 [SMILES: Cc1cc(/C=C2\SC(=S)N(CC(=O)O)C2=O)cc(O)c1O] | 21 | 2.23 |
| AT50-A47 | 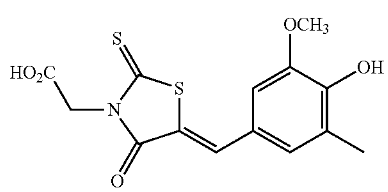 | 21 | 2.05 |
| AT50-A49 | 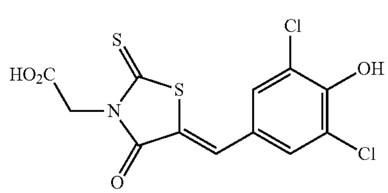 [SMILES: O=C(O)CN1C(=O)/C(=C/c2cc(Cl)c(O)c(Cl)c2)SC1=S] | 4 | 0.89 ± 0.15 |
| AT50-A50 | 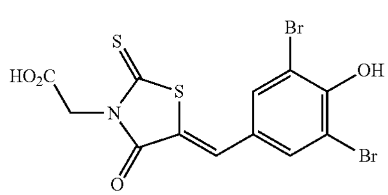 [SMILES: O=C(O)CN1C(=O)/C(=C/c2cc(Br)c(O)c(Br)c2)SC1=S] | 8 | 0.90 |

TABLE 2-continued

| Compound | Structure | WT-TTR amyloid inhibition in vitro Fibril Formation (%) | IC$_{50}$ (μM) |
|---|---|---|---|
| AT50-A51 | 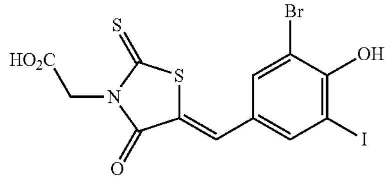 [SMILES: O=C(O)CN1C(=O)/C(=C/c2cc(Br)c(O)c(I)c2)SC1=S] | 5 | 1.07 ± 0.42 |
| AT50-B00 | 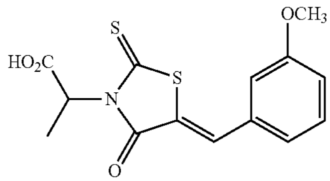 [SMILES: COc1cccc(/C=C2\SC(=S)N(C(C)C(=O)O)C2=O)c1] | 35 | 2.38 ± 0.17 |
| AT50-B01 | 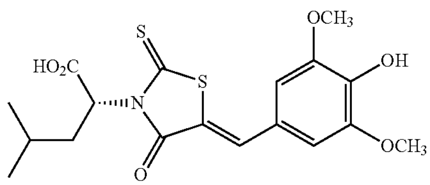 [SMILES: COc1cc(/C=C2\SC(=S)N([C@H](CC(C)C)C(=O)O)C2=O)cc(OC)c1O] | 10 | 0.95 ± 0.45 |
| AT50-C00 | 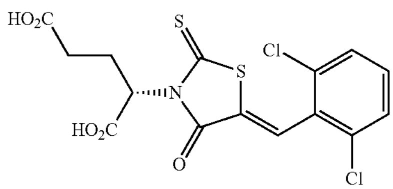 [SMILES: O=C(O)CC[C@@H](C(=O)O)N1C(=O)/C(=C/c2c(Cl)cccc2Cl)SC1=S] | 26 | 2.05 ± 0.04 |
| AT50-C01 | 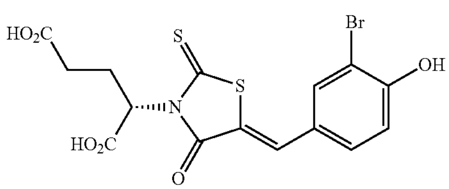 [SMILES: O=C(O)CC[C@@H](C(=O)O)N1C(=O)/C(=C/c2ccc(O)c(Br)c2)SC1=S] | 13 | 1.38 ± 0.30 |
| AT50-C02 | 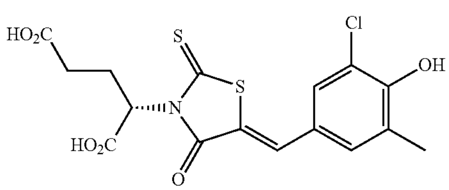 [SMILES: Cc1cc(/C=C2\SC(=S)N([C@@H](CCC(=O)O)C(=O)O)C2=O)cc(Cl)c1O] | 18 | 1.79 ± 0.13 |
| AT50-C09 | 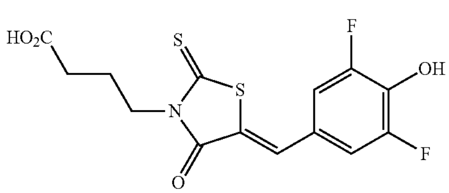 [SMILES: O=C(O)CCCN1C(=O)/C(=C/c2cc(F)c(O)c(F)c2)SC1=S] | 33 | 2.45 ± 0.35 |
| AT50-C10 | 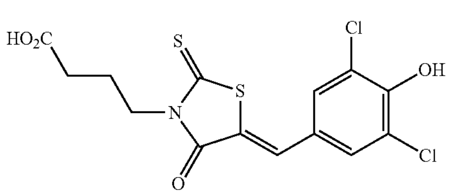 [SMILES: O=C(O)CCCN1C(=O)/C(=C/c2cc(Cl)c(O)c(Cl)c2)SC1=S] | 27 | 1.87 ± 0.16 |

TABLE 2-continued

| Compound | Structure | WT-TTR amyloid inhibition in vitro Fibril Formation (%) | IC$_{50}$ (μM) |
|---|---|---|---|
| AT50-C11 | 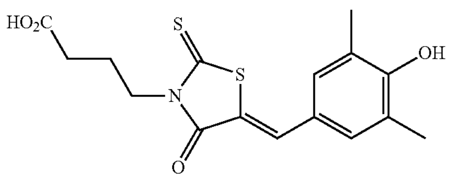 [SMILES: Cc1cc(/C=C2\SC(=S)N(CCCC(=O)O)C2=O)cc(C)c1O] | 26 | 2.43 ± 1.25 |
| AT50-C13 | 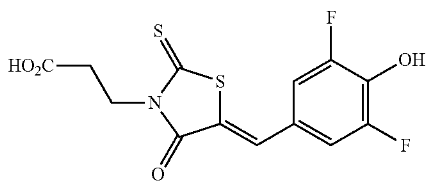 [SMILES: O=C(O)CCN1C(=O)/C(=C/c2cc(F)c(O)c(F)c2)SC1=S] | 32 | 2.31 ± 0.45 |
| AT50-C14 | 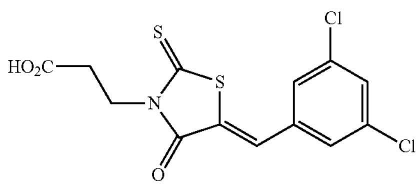 [SMILES: O=C(O)CCN1C(=O)/C(=C/c2cc(Cl)cc(Cl)c2)SC1=S] | 26 | 1.95 ± 0.26 |
| AT50-C15 | 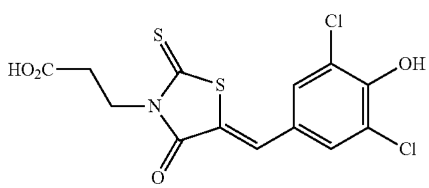 [SMILES: O=C(O)CCN1C(=O)/C(=C/c2cc(Cl)c(O)c(Cl)c2)SC1=S] | 7 | 1.03 ± 0.10 |
| AT50-C16 | 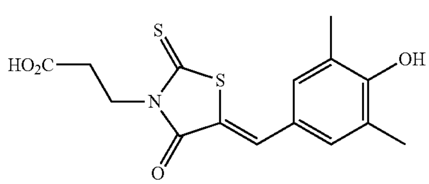 [SMILES: Cc1cc(/C=C2\SC(=S)N(CCC(=O)O)C2=O)cc(C)c1O] | 24 | 2.29 ± 0.13 |
| AT50-C18 | 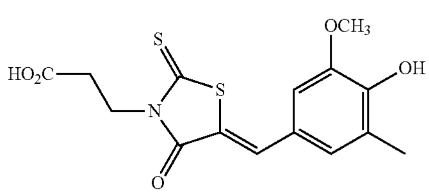 [SMILES: COc1cc(/C=C2\SC(=S)N(CCC(=O)O)C2=O)cc(C)c1O] | 30 | NA |
| AT50-C19 | 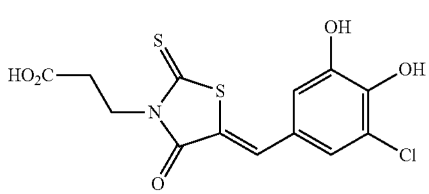 [SMILES: O=C(O)CCN1C(=O)/C(=C/c2cc(O)c(O)c(Cl)c2)SC1=S] | 33 | NA |
| AT50-C20 | 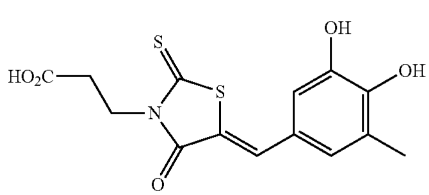 [SMILES: Cc1cc(/C=C2\SC(=S)N(CCC(=O)O)C2=O)cc(O)c1O] | 39 | NA |

TABLE 2-continued

| Compound | Structure | WT-TTR amyloid inhibition in vitro | |
|---|---|---|---|
| | | Fibril Formation (%) | $IC_{50}$ (μM) |
| Reference compounds | | | |
| Thyroxine | 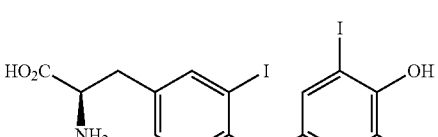 | 28 | 2.20 ± 0.03 |
| 2OH-PCB80 | 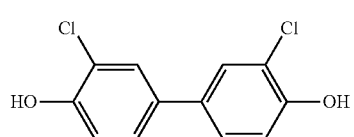 | 20 | 1.59 ± 0.27 |
| Tafamidis | 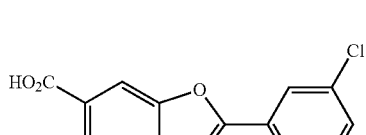 | 43 | 3.10 ± 0.15 |

In vitro activity of the N-substituted arylidenerhodanines and arylidenethiazolidinediones against amyloid fibril formation by wild type transthyretin (WT-TTR). Fibril formation of WT-TTR (at 3.6 μM concentration) is induced by acidification of the solution to pH 4.4 in the presence of the test compound. The amount of amyloid fibrils formed is monitored over 72 hours by turbidimetry measurements taken at 405 nm, 450 nm and 490 nm (or at 550 nm, 600 nm and 650 nm when the compound absorbs light at the previous wavelengths), and at 37° C. The tabulated percentages of fibril formation correspond to 1:1 TTR-compound stoichiometry and are normalized to the negative control, which corresponds to the amount of formed WT-TTR fibrils quantified after 72 hours of incubation in absence of compound (i.e. 100% of fibril formation). Compound concentrations inhibiting amyloid fibril formation by 50% ($IC_{50}$) values were determined by monitoring the effect of increasing concentrations of the compounds on the inhibition patterns. Ten different compound concentrations were used for each $IC_{50}$ determination, while WT-TTR concentration was kept fix at 3.6 μM. Values that are still under determination and thus unavailable at the moment are denoted by "NA".

TABLE 3

| Compound | Structure | V122I-TTR amyloid inhibition in vitro | |
|---|---|---|---|
| | | Fibril Formation (%) | $IC_{50}$ (μM) |
| AT50-A00 (Z) | 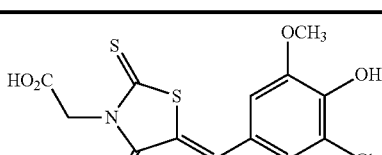 | 52 | 3.73 |
| AT50-A00 (E) | 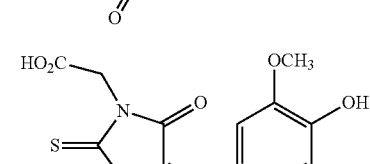 | 45 | 3.06 |

TABLE 3-continued

| Compound | Structure | V122I-TTR amyloid inhibition in vitro | |
|---|---|---|---|
| | | Fibril Formation (%) | IC$_{50}$ (μM) |
| AT50-A01 | 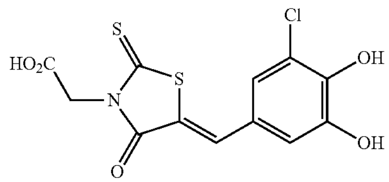 [SMILES: O=C(O)CN1C(=O)/C(=C/c2cc(O)c(O)c(Cl)c2)SC1=S] | 29 | 2.34 |
| AT50-A03 | 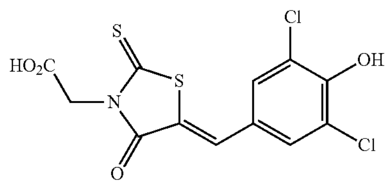 [SMILES: O=C(O)CN1C(=O)/C(=C/c2cc(Cl)c(O)c(Cl)c2)SC1=S] | 19 | 1.61 |
| AT50-A05 | 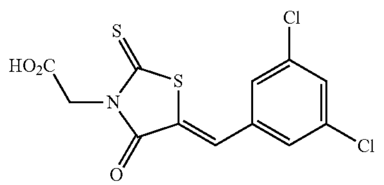 [SMILES: O=C(O)CN1C(=O)/C(=C/c2cc(Cl)cc(Cl)c2)SC1=S] | 28 | 2.32 |
| AT50-A12 | 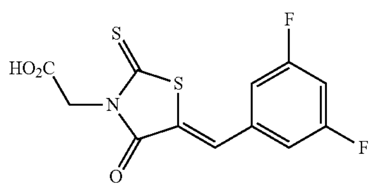 [SMILES: O=C(O)CN1C(=O)/C(=C/c2cc(F)cc(F)c2)SC1=S] | 91 | 7.80 |
| AT50-A17 | 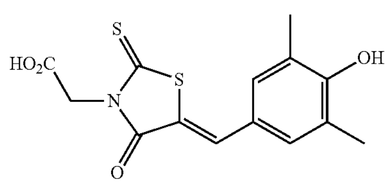 [SMILES: Cc1cc(/C=C2\SC(=S)N(CC(=O)O)C2=O)cc(C)c1O] | 51 | 3.16 |
| AT50-A49 | 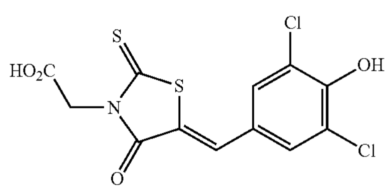 | 12 | 1.32 |
| AT50-B01 | 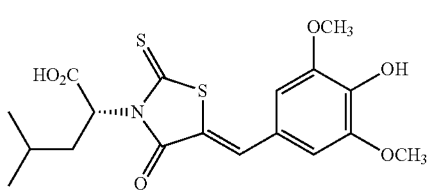 [SMILES: COc1cc(/C=C2\SC(=S)N([C@H](CC(C)C)C(=O)O)C2=O)cc(OC)c1O] | 20 | 1.48 |
| AT50-C01 | 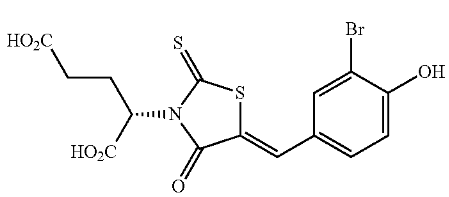 [SMILES: O=C(O)CC[C@@H](C(=O)O)N1C(=O)/C(=C/c2ccc(O)c(Br)c2)SC1=S] | 39 | 2.66 |

TABLE 3-continued
| Compound | Structure | V122I-TTR amyloid inhibition in vitro | |
|---|---|---|---|
| | | Fibril Formation (%) | IC$_{50}$ (μM) |
| AT50-C09 | 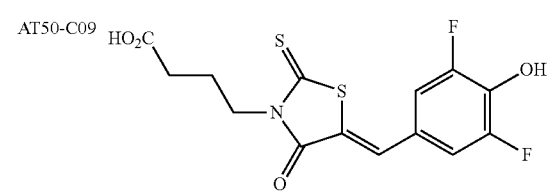 | 48 | 3.19 |
| AT50-C10 | 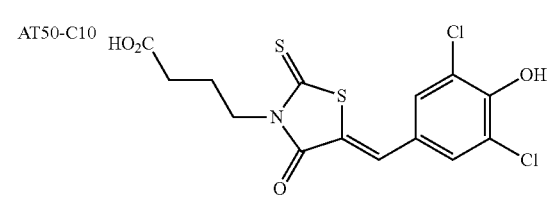 | 37 | 2.46 |
| AT50-C11 | 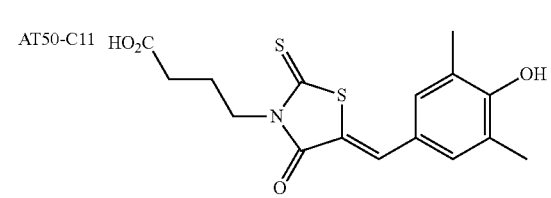 | 66 | 4.52 |
| AT50-C13 | 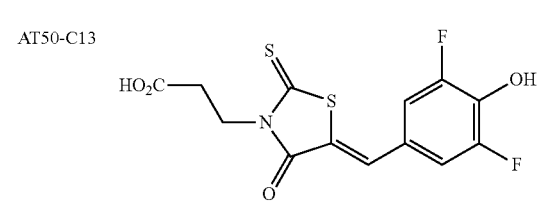 | 36 | 2.60 |
| AT50-C14 | 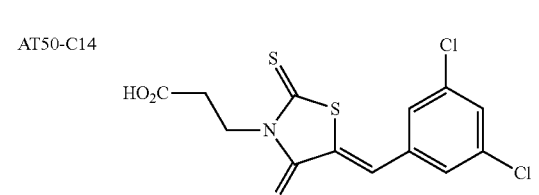 | 55 | 4.37 |
| AT50-C15 | 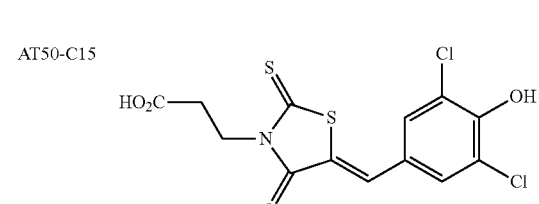 | 17 | 1.62 |
| AT50-C16 | 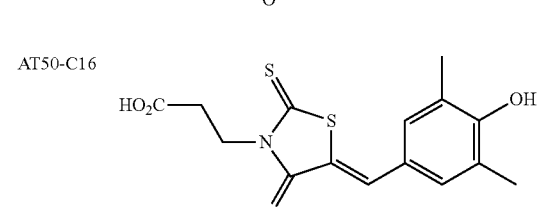 | 41 | 2.71 |

TABLE 3-continued

| Compound | Structure | V122I-TTR amyloid inhibition in vitro | |
|---|---|---|---|
| | | Fibril Formation (%) | IC$_{50}$ (µM) |
| Reference compounds | | | |
| Thyroxine | 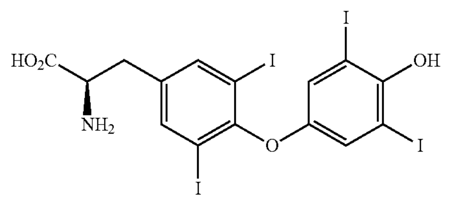 [SMILES: N[C@H](Cc1cc(I)c(Oc2cc(I)c(O)c(I)c2)c(I)c1)C(=O)O] | 42 | 3.22 |
| 2OH-PCB80 | 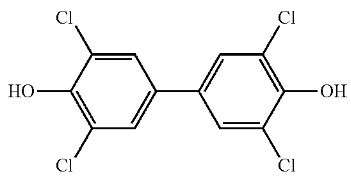 [SMILES: Oc1c(Cl)cc(-c2cc(Cl)c(O)c(Cl)c2)cc1Cl] | 24 | 1.45 |
| Tafamidis | 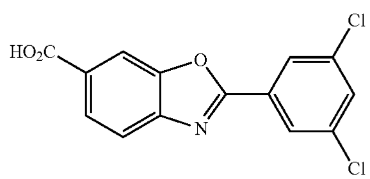 [SMILES: O=C(O)c1ccc2nc(-c3cc(Cl)cc(Cl)c3)oc2c1] | 49 | 3.70 |

In vitro activity of the N-substituted arylidenerhodanines and arylidenethiazolidinediones against amyloid fibril formation by the Val130Ile transthyretin variant (V122I-TTR) involved in FAC. Fibril formation of V122I-TTR (at 3.6 µM concentration) is induced by acidification of the solution to pH 4.4 in the presence of the test compound. The amount of amyloid fibrils formed is monitored over 72 hours by turbidimetry measurements taken at 405 nm, 450 nm and 490 nm (or at 550 nm, 600 nm and 650 nm when the compound absorbs light at the previous wavelengths), and at 37° C. Compound concentrations inhibiting amyloid fibril formation by 50% (IC$_{50}$) values were determined by monitoring the effect of increasing concentrations of the compounds on the inhibition patterns. Ten different compound concentrations were used for each IC$_{50}$ determination, while V122I-TTR concentration was kept fix at 3.6 µM.

Figure 23:
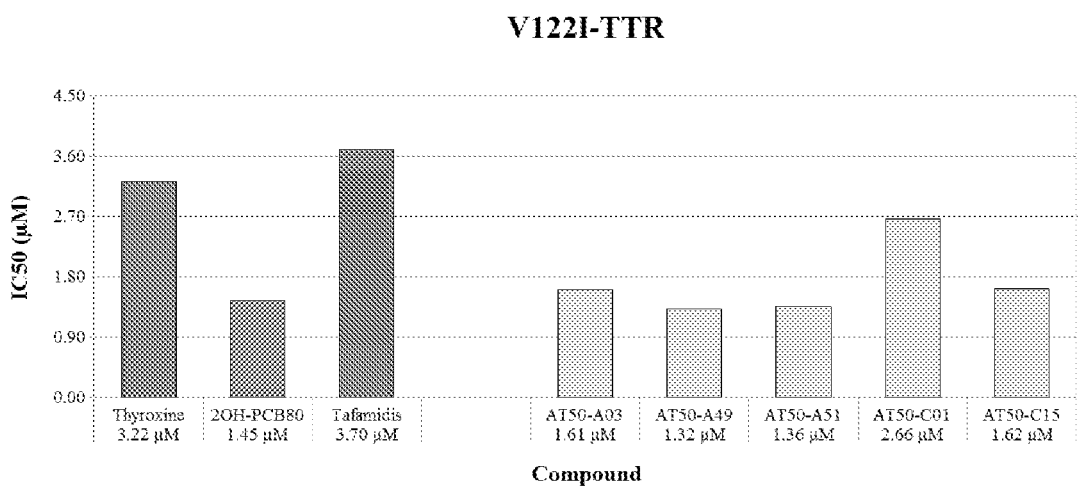
FIG. 23. Concentration of test compounds capable of inhibiting Val122Ile transthyretin (V122I-TTR) amyloid fibril formation by 50% (here denoted by an $IC_{50}$). The values were determined by monitoring the effect of increasing concentrations of the compounds on the inhibition patterns. Ten different compound concentrations were used for each $IC_{50}$ determination, while V122I-TTR concentration was kept fix at 3.6 µM. Three reference compounds are contrasted with five of the most active compounds belonging to the AT50 series. On the left, the reference compounds thyroxine (T4), 2OH-PCB80 and Tafamidis are shown. On the right, the $IC_{50}$ values corresponding to the inhibitory activities of optimized, "short-tailed" arylidenerhodanines (AT50-A03) and arylidenethiazolidinediones (AT50-A49 and AT50-51), as well as "long-tailed" arylidenerhodanine analogues (AT50-C01 and AT50-C15) are plotted. When present, the error bars correspond to standard deviations.

FIG. 19 and FIG. 23 respectively show the concentration of test compounds capable of inhibiting amyloid fibril formation by wild type TTR (WT-TTR) and by the Val122Ile transthyretin variant (V122I-TTR)—by 50% (denoted by an IC$_{50}$). The values were determined by monitoring the effect of increasing concentrations of the compounds on the inhibition patterns. Ten different compound concentrations were used for each IC$_{50}$ determination, while WT-TTR concentration was kept fix at 3.6 µM. In both figures, three reference compounds are contrasted with five of the most active compounds belonging to the AT50 series. On the left, the reference compounds thyroxine (T4), 2OH-PCB80 and Tafamidis are shown. On the right, the IC$_{50}$ values corresponding to the inhibitory activities of the optimized, "short-tailed" arylidenerhodanines (AT50-A03) and arylidenethiazolidinediones (AT50-A49 and AT50-51), as well as "long-tailed" arylidenerhodanine analogues (AT50-C01 and AT50-C15), are plotted. When present, the error bars correspond to standard deviations.

As previously underlined, TTR is prone to bind lipophilic compounds, such as its natural endogenous binder, thyroxine (T4), and a known pollutant, a polychlorinated biphenyl, herein referred to as 2OH-PCB. Highly lipophilic compounds, however, are associated with the several problems, such as liver-cell toxicity, bioaccumulation or difficult pharmaceutical formulation in dosage forms. Therefore, there is interest in discovering and developing TTR stabilizers capable of inhibiting amyloid formation but also holding appropriate physicochemical properties.

Figure 20:
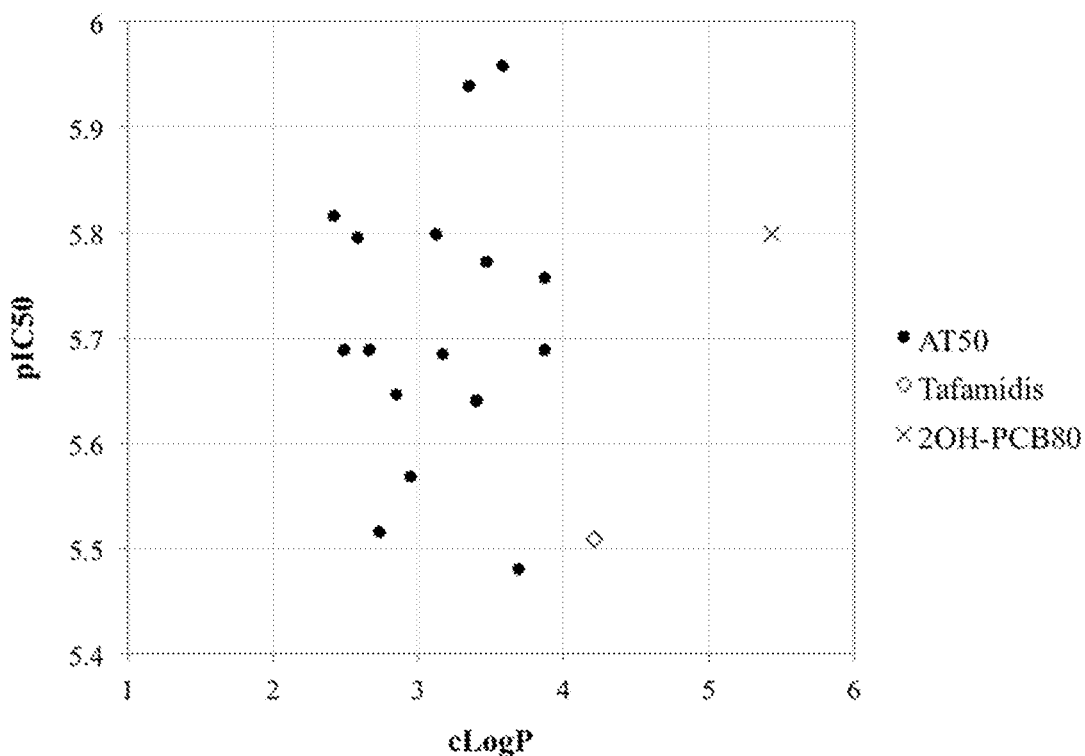
FIG. 20. Activity versus (predicted) lipophilicity plot for some of the AT50 compounds compared with two reference compounds, Tafamidis and 2OH-PCB80. The plotted activity values represent the negative logarithm of the concentration inhibiting amyloid fibril formation by WT-TTR by 50% ($pIC_{50}$), while cLogP values are computationally predicted octanol-water partition-coefficients.

While we are currently assembling a protocol for experimentally measuring/quantifying the solubility of AT50 compounds, we resort to computational methodologies to provide an estimation of the lipophilicity of the compounds and contrast it with their amyloid inhibitory activity. FIG. 20 provides an interesting picture of the relationship between the activity of the compounds and their predicted lipophilicity. Interestingly, all represented AT50 compounds positioned within an acceptable lipophilicity range, with cLogP values inferior to 2OH-PCB80 and Tafamidis, while still showing promising activity values (as reported in Table 2).

Activity of E Stereoisomers

Figure 21:
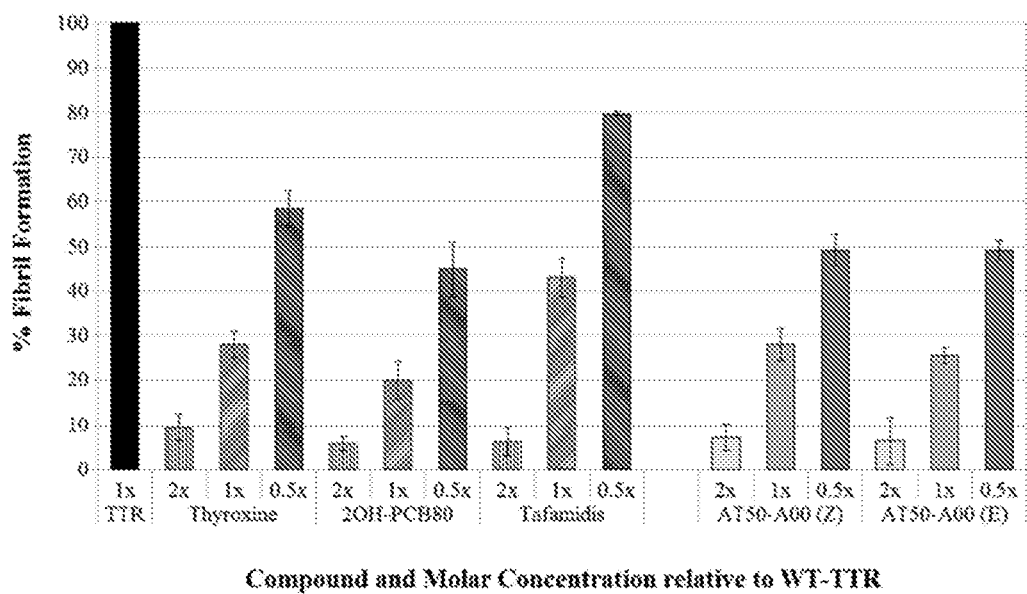
FIG. 21. In vitro activity of stereoisomers E and Z of AT50-A00 against amyloid fibril formation by TTR, at three distinct stoichiometries of compound versus wild type TTR (WT-TTR)—2:1 (2×), 1:1 (1×) and 1:2 (0.5×). In this assay, fibril formation of WT-TTR at 3.6 μM concentration is induced by acidification of the solution to pH 4.4 in the presence of a stabilizer compound. The amount of amyloid fibrils formed is monitored over 72 hours by turbidimetry measurements taken at 405 nm, 450 nm and 490 nm (or at 550 nm, 600 nm and 650 nm when the compound absorbs light at the previous wavelengths), and at 37° C. All values are normalized to the negative control (black bar), i.e. 100% of fibril formation, which in turn corresponds to the amount of formed WT-TTR fibrils quantified after 72 hours of incubation in absence of compound. Here, the inhibitory activity of the two stereoisomers of the original virtual screening hit, AT50-A00 (Z) and AT50-A00 (E) (on the right), are contrasted with that of three reference compounds, thyroxine (T4), 2OH-PCB80 and Tafamidis (on the left). The error bars correspond to standard deviations.
Figure 22:
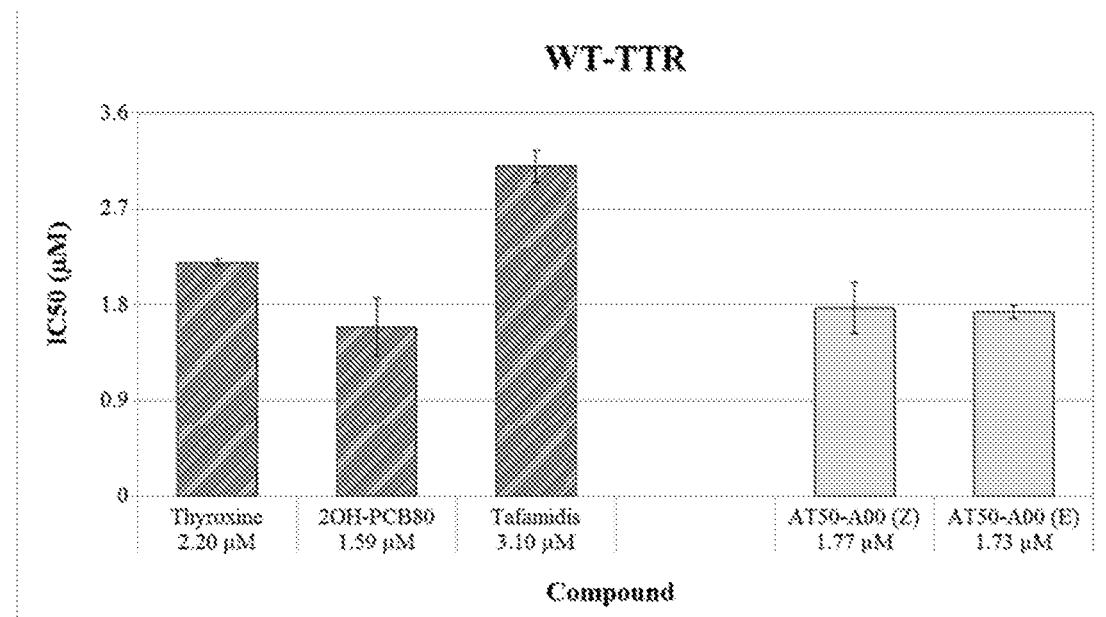
FIG. 22. Compound concentrations inhibiting amyloid fibril formation by TTR by 50% ($IC_{50}$). $IC_{50}$ values were determined by monitoring the effect of increasing concentrations of the compounds on the inhibition values. Ten different compound concentrations were used for each $IC_{50}$ assay, along with a fixed TTR concentration (3.6 µM). Ten different compound concentrations were used for each $IC_{50}$ assay, along with a fix TTR concentration (3.6 µM). Here, the $IC_{50}$ values of the two stereoisomers of the original virtual screening hit, AT50-A00 (Z) and AT50-A00 (E) (on the right), are contrasted with those of three reference compounds, thyroxine (T4), 2OH-PCB80 and Tafamidis (on the left). The error bars correspond to standard deviations.

The hypothesis that E stereoisomeric forms of AT50 compounds are equally active as the Z stereoisomeric forms was experimentally tested upon acquisition of the commercially-available compound (E)-3-hydroxycarbonylmethyl-5-(3'-chloro-4'-hydroxy-5'-methoxyphenylmethylidene)-2-thioxothiazolidin-4-one, the E stereoisomer of the virtual screening hit AT50-A00. FIG. 21 and FIG. 22 show that the Z-stereoisomeric form of AT50-A00 and the corresponding E-stereoisomeric form of AT50-A00 share the same level of activity towards the inhibition of amyloid fibril formation by TTR, thus providing experimental evidence of the activity of the E stereoisomer of AT50-A00.

The example provided herein, supplemented by both molecular modeling and experimental data, supports the notion that E stereoisomers of the AT50 compounds described herein are as capable of stabilizing TTR and preventing fibril formation as their Z-stereoisomeric counterparts.

Binding Competition with T4 for TTR (and Other T4 Carriers in Plasma)

Binding competition with thyroxine (T4) for TTR and other T4-binding plasma proteins (namely, albumin and thyroxine-binding globulin) was studied through an assay based on gel electrophoresis described in the "Materials and Methods" section. The assay was applied to the confirmed virtual screening hit AT50-A00, in order to validate its mode of action based on binding to TTR's T4 binding sites and also to obtain a preliminary (indirect) assessment of the compounds selectivity for TTR versus the other main carrier proteins present in plasma that hold affinity for T4-like molecules. Here, Tafamidis and with Iododiflunisal were used as reference.

Figure 24:
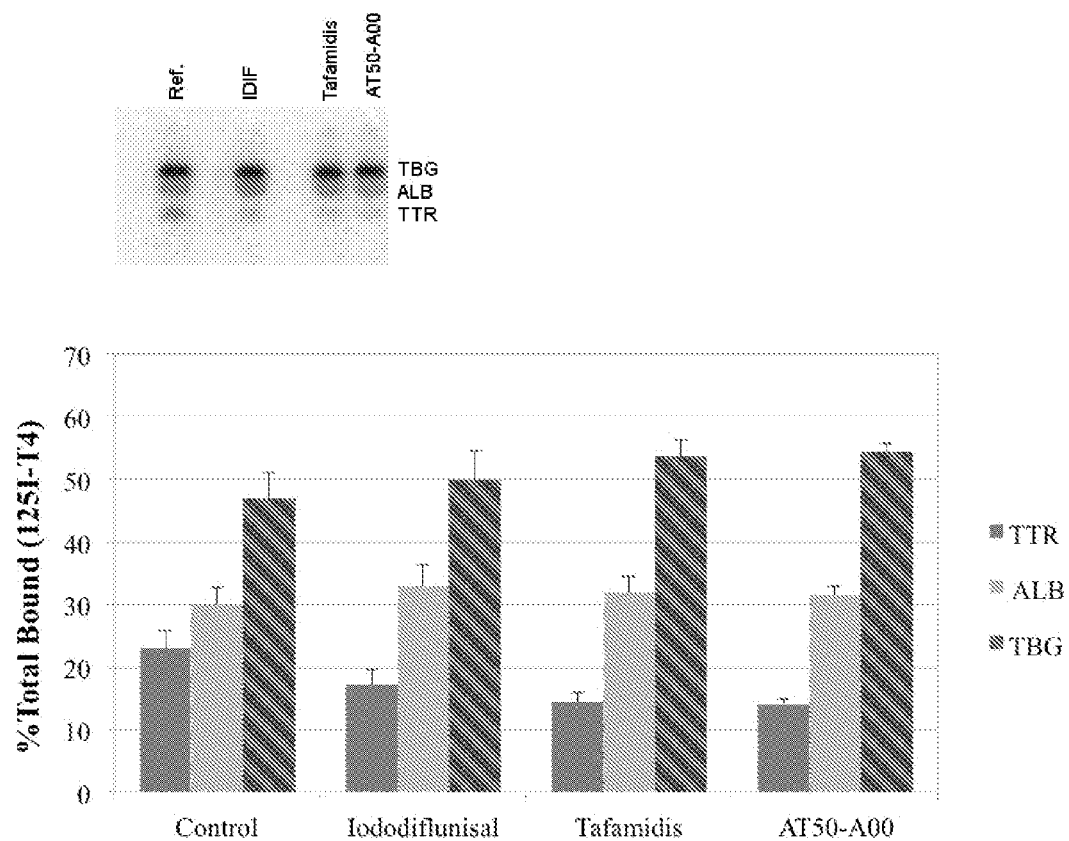
FIG. 24. Binding competition with thyroxine (T4) for TTR and other T4-binding plasma proteins, studied through an assay based on gel electrophoresis, for the original virtual screening hit AT50-A00. Iododitlunisal (IDIF) and Tafamidis are used as reference, incubated in equal amount as the test compound. In the upper panel, the bands correspond to the major T4 binding plasma proteins, namely albumin (ALB), transthyretin (TTR) and thyroxine-binding globulin (TBG). The intensity of the bands decreases, as compared to the control samples (absence of compound), if the compound binds to the protein(s) competing with T4. The results are analyzed by calculation of the TTR/total (TTR+ALB+TBG) ratio for each sample collected at different time points. In the lower panel, the displacement of T4 from TTR is calculated and plotted as the difference between the average of ratios of TTR/total protein for each control sample and the average of the ratios of TTR/total protein.

FIG. 24 presents the results of these experiments, where the bands in the gel correspond to the major T4 binding plasma proteins. The intensity of the bands decreases, as compared to the control samples (absence of compound), if the compound binds to the protein(s) competing with T4. The results were analyzed by calculation of the TTR/total (TTR+ALB+TBG) ratio for each sample collected at different time points. The displacement of T4 from TTR is calculated and plotted as the difference between the average of ratios of TTR/total protein for each control sample and the average of the ratios of TTR/total protein. As can be seen through the control, thyroxine-binding globulin (TBG) holds the highest affinity for T4, followed by albumin and lastly by TTR. Competition with T4 by a test compound holding higher affinity for TTR is expected to alter the T4's binding profile observed in the control experiment, decreasing the amount of T4 bound to TTR and, consequently, increasing the amount of T4 (dislocated from TTR) that binds to ALB and TBG. As can be seen in FIG. 24, this is change is observed with all tested compounds, with Tafamidis (14.4%, 32.0% and 53.6% of T4 bound to TTR, ALB and TBG, respectively) and AT50-A00 (14.2%, 31.5% and 54.3% of T4 bound to TTR, ALB and TBG, respectively) achieving the best affinity/selectivity profiles.

The fact that compound AT50-A00 offered results comparable to Tafamidis, prior to any optimization efforts, was another positive indication on the promise of the new N-substituted arylidenerhodanine scaffold described herein towards the development of TTR amyloid inhibitors.

Example 4

Evaluation of TTR Stabilizer Activity of Compounds

Figure 25:
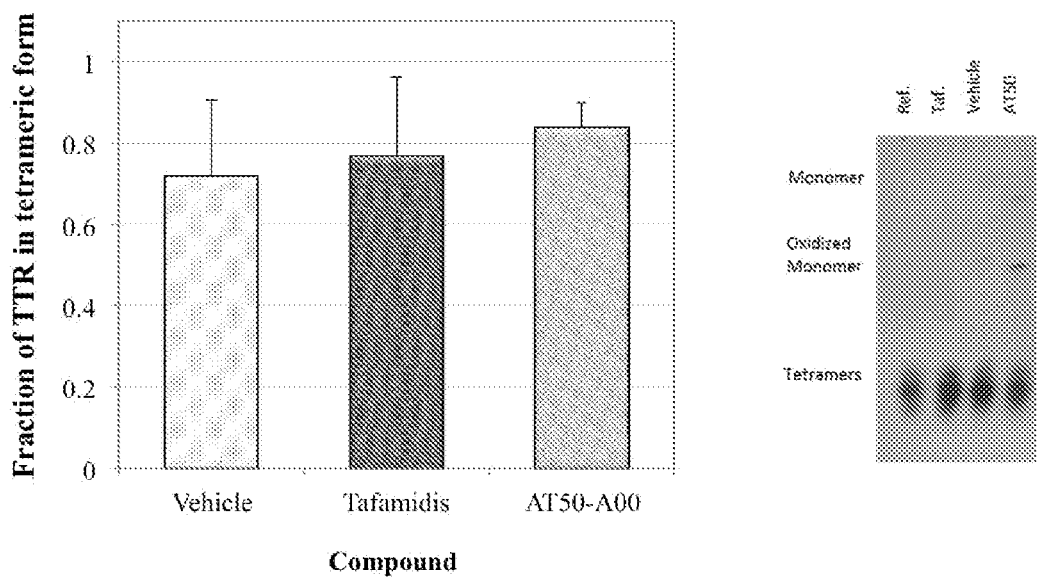
FIG. 25. Fraction of plasma TTR in tetrameric form upon incubation with Tafamidis and the original virtual screening hit AT50-A00. After treatment with compounds, TTR was separated by PAGE and the isolated protein was analyzed by IEF. The molecular species identified in the IEF gel after Coomassie Blue staining are denoted in the right panel. In the presence of Tafamidis and AT50-A00 stronger bands corresponding to TTR tetramers were observed and the bands corresponding to monomeric species were reduced or absent. The histogram shows the result of IEF densitometric analysis of isolated TTR incubated with the compounds, expressed as the tetramer/monomer ratio (left panel).

TTR stability in presence of Tafamidis and compound AT50-A00 was independently assessed using an ex vivo assay based on isoelectric focusing (IEF) with human plasma TTR, as described in references [23,24] and in the "Evaluation of tetrameric TTR stability by IEF" subsection of the "Materials and Methods" section. After treatment with the test compounds, TTR was separated by PAGE and the isolated protein was analyzed by IEF. As shown in FIG. 25 (right panel), in the presence of Tafamidis and AT50-A00 stronger bands corresponding to TTR tetramers were observed and the bands corresponding to monomeric species were reduced or absent. The histogram (left panel) shows the result of IEF densitometric analysis of isolated TTR incubated with the compounds, expressed as the tetramer/monomer ratio. Samples incubated with Tafamidis and AT50-A00 yielded a tetramer/monomer ratio of 0.767 and 0.838, respectively, compared with 0.717 of the control (vehicle).

The results confirm the TTR stabilizing activity of the original virtual screening hit AT50-A00, implying an agreement with the results of in vitro evaluation of activity against amyloid fibril formation. The results also offered confidence to carry out expansion/optimization of the AT50 compound series.

Example 5

Evaluation of the Cytotoxicity of the Compounds

Throughout lead series expansion and optimization of the AT50 series, preliminary toxicology was carried out via broad toxicity predictions and cheminformatics workflows powered by the Derek Nexus expert system (Lhasa Limited), and also via experimental evaluation of the cytotoxicity of the most active optimization derivatives using cell-based assays. Cell viability of HepG2 hepatoma cells was quantified in order to assess the toxicity of the compounds at increasing concentrations. The used assay is described in detail in the "Experimental Evaluation of Cytotoxicity of Compounds using Cell-based Assays" section in "Materials and Methods". This is a relevant assessment not just to discard potential concerns of liver damage (which is a problem reported for many drugs) but also because of the long-term nature of the treatments that patients suffering from TTR-mediated amyloidoses need to undertake.

Figure 26:
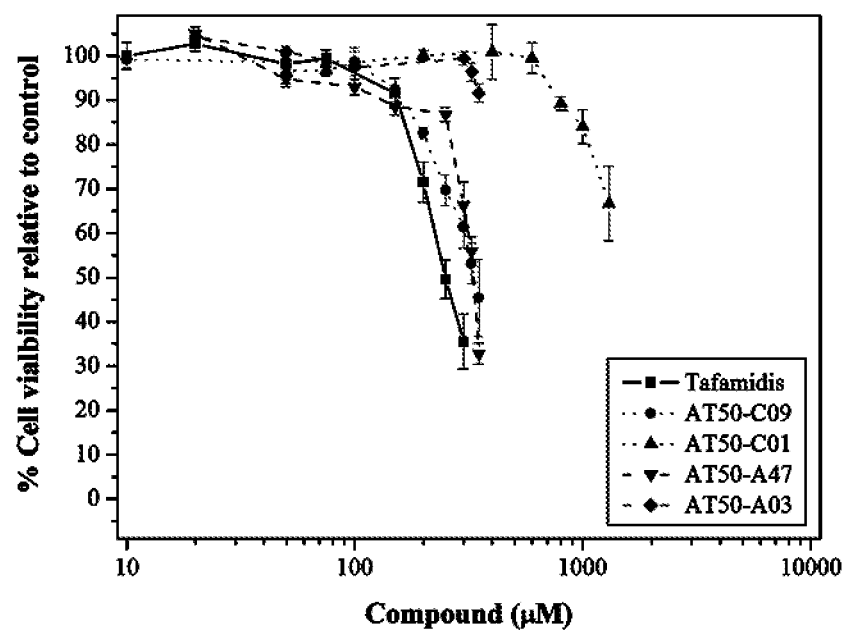
FIG. 26. Viability of HepG2 (hepatoma) cells in the presence of increasing concentrations of selected compounds belonging to the AT50 series and Tafamidis. The cell viability was assessed by the resazurin reduction assay. Quantification of the reduction of resazurin to resorufin proceeded by microplate absorbance readings taken at two wavelengths, 540 nm (reduced form) and 630 nm (oxidized form), in a Biotek spectrophotometer microplate reader, and was followed by calculation of the percentage of viable cells. The lines in the plots correspond to trend lines obtained by either linear fitting (AT50 compounds) or simply connecting the different measurements (Tafamidis).

FIG. 26 shows the results of cell viability studies conducted with compounds AT50-A03 and AT50-A06, two very active TTR-amyloid inhibitors. The plot shows that these compounds are relatively harmless to HepG2 cells, even at high concentrations, especially when compared with Tafamidis. Indeed, while an inhibitory dose ($ID_{50}$) of approximately 250 µM was obtained with Tafamidis, compounds AT50-A00, AT50-A03 and AT50-A06 (some of the most active examples) all displayed $ID_{50}$ values above 400 µM. These results represented a promising indication on the safety of the compounds belonging to the AT50 series.

Example 6

Combination Therapy

The compounds provided herein may be administered as a monotherapy or in combination with other active ingredients. For example, the compounds may be administered in combination with other compounds used in the treatment of amyloidoses and amyloid disorders. Active ingredients for combination therapy may include but are not limited to tafamidis meglumine (brand name VYNDAQEL), donepezil hydrochloride (brand name ARICEPT), tolcapone (brand name TASMAR), patisiran (currently experimental), resuviran (currently experimental) and other products approved for treatment of amyloidoses, including but not limited to Familial Amyloid Polyneuropathy, Familial Amyloid Cardiomyopathy or Senile Systemic Amyloidosis, AA amyloidosis, Alzheimer's disease, Light-Chain (AL) amyloidosis, Type-2 Diabetes, Medullary Carcinoma of the Thyroid, Parkinson's disease, Polyneuropathy, Spongiform Encephalopathy (Creutzfeldt Jakob disease).

Example 7

Materials and Methods
Workflow for Discovery of Novel TTR-Amyloid Inhibitors

One basic premise of this discovery program was the definition of protocols for the discovery of novel, potent TTR-amyloid inhibitors devoid of hormonal activity as in thyroxine, cyclooxygenase inhibitory activity as in the NSAIDs, or risks of bioaccumulation and carcinogenic effects as in the PCBs. Of equal importance was the selection of inhibitors holding pharmacological properties and safety profiles appropriate for the long-term therapies required by some patients suffering from TTR-mediated amyloidoses.

1. Assembly of Virtual Screening Library

A tailored virtual library including a total of 2,259,573 compounds was assembled by filtering of an original set comprised of 10,962,930 small organic molecules deposited in the ZINC database (2008 version), purchasable from various chemical vendors worldwide. The filtering criteria included a set of predefined rules for drug-likeness and bioavailability, as well as rules derived from analysis of physicochemical properties of known TTR stabilizers. Pharmacokinetic predictors included Lipinski's rule-of-five [25], allowing up to one violation and defining hydrogen-bond donors and acceptors as outlined in the work of Mills and Dean [26], Veber's (GSK) rules [27], Martin's (Abbott) bioavailability score [28], and Pharmacopeia's "Egan egg" bioavailability rule [29]. Aggregators are small molecules respectively known or predicted to aggregate and sequester protein in solution, thus interfering with biochemical assay results [30,31]. Compounds classified or predicted as "aggregators" were filtered out. Molecules predicted insoluble or poorly soluble in water were also discarded. Furthermore, to ensure that no redundant molecules were included and that no potential TTR stabilizers were filtered out at early stages of the library filtering process, a number of definitions were defined based on the distribution of various physicochemical properties of known TTR stabilizers.

2. Ligand-Based Virtual Screening

Several ligand-based virtual screening (VS) protocols were assessed for their ability to discriminate active TTR stabilizers from decoy molecules. Reference [20] illustrates the type of ligand-based virtual screening protocols considered in this work. Several VS runs employing some of the best-performing protocols, alone and in combinations (using consensus scoring approaches), were performed and library compounds were sorted according to their VS scores. The top-thousand molecules in each rank, holding the highest VS scores, were selected for further cheminformatics analysis.

The choice of reference TTR stabilizers to use as query for ligand-based virtual screening was based on previously reported TTR-amyloid inhibitory activity [32-36]. In the virtual screening experiments reported here, four compounds were critical to the selection and modeling of template queries (see FIG. 4). The natural, endogenous TTR binder, (2S)-2-amino-3-[4-(4-hydroxy-3,5-diiodophenoxy)-3,5-diiodophenyl]propanoic acid (commonly referred to as thyroxine and abbreviated as T4), is known to stabilize TTR and prevent amyloid fibril formation to some extent [33]; compound 2,6-dichloro-4-(3,5-dichloro-4-oxidophenyl)benzen-1-olate, an hydroxylated polychlorinated biphenyl (often referred to as 4,4'-dihydroxy-PCB80 or simply 2OH-PCB80) is known as one of the most potent TTR ligands and TTR-amyloid inhibitor [32,36]; compound 10-[3-(trifluoromethyl)phenyl]-10,10a-dihydro-4aH-phenoxazine-4,6-dicarboxylate (known as Phenox) is a TTR ligand that has been based on flufenamic acid (a non-steroidal anti-inflammatory drug discovered to bind TTR) and optimized using structure-based design [34,35]; PCX2 is a modeled compound reported in reference [20] as compound number 27 (FIG. 2 of reference [20]), which attempts to combine key pharmacophoric features of the previous ligands in a single query for virtual screening. Phenox served as a template scaffold for the modeling of missing features thought as important for both shape complementarity with TTR binding sites and direct interaction with the hydroxyl side chains of two serine residues located at the inner portion of the sites [35,37,38]. The resulting compound is thus a concatamer of ligands T4, 2OH-PCB80 and Phenox, where a carboxyl group was added at the para position of the benzene ring that is placed deeper inside TTR ligand-binding sites; a trifluoromethyl (present at the meta position of the same benzene ring) was replaced by a chlorine atom; an extra chlorine atom was added at position 5 of the ring (thus creating symmetry around the benzene ring); and an oxygen linker connecting the two ring systems of the molecule was introduced (as in T4).

The atom coordinates of the known TTR ligands were extracted from the corresponding X-ray structures deposited in the Protein Data Bank (PDB) [39]: PDB entry 2ROX for thyroxine, 2G5U for 2OH-PCB80 and 1DVY for Phenox. By contrast, the modeled structure of PCX2 was energy minimized, and conformational sampling was performed to identify low-energy configurations, retaining the one holding closest similarity to the X-ray conformation of Phenox (PDB entry 1DVY).

3. Post-Screening Filtering and Analysis

The top thousand compounds retrieved by virtual screening (VS) were further filtered using tighter criteria for physicochemical and pharmacokinetic predictors. For example, the maximum octanol-water partition coefficient (quantified using the XlogP method) allowed was set to 3.0 and minimum polar surface area (PSA) was set to 90. Subsets comprised by the top-100 compounds predicted to be soluble, very soluble or highly soluble were assembled. The structural alignment of each compound against the chosen template molecule was visually inspected, with emphasis on the analysis of the overlapping of chemical/pharmacophoric features. Furthermore, all top ranked compounds were docked into the T4-binding sites of TTR, as exemplified in reference [20] with known TTR ligands deposited in the Protein Data Bank (PDB). The structures of TTR in complex with flufenamic acid (1BM7) and 2OH-PCB80 (2G5U) were selected for providing reliable pose predictions against a variety of ligands, as concluded through the cross-docking studies reported in reference [20]. Visual inspection of the docked poses for each of the top hundred (predicted soluble) compounds allowed for a final selection of virtual screening hits to be acquired from chemical vendors and experimentally evaluated through a biochemical assay described in this document. Only compounds showing an appropriate (predicted) binding mode within T4 binding sites were purchased to undergo biochemical evaluation.

4. Acquisition from Chemical Vendors

Compounds selected through in silico screening were purchased from various suppliers of chemicals spread around the world, in order to be evaluated for anti-amyloid activity. All purchased compounds were of the highest purity commercially available. For each ZINC code corresponding to the selected virtual screening hits (VS hits), a short list of suppliers was obtained from the ZINC database. The choice of supplier was influenced by distinct criteria such as high chemical purity, adequate confidentiality policies, best price and availability of multiple virtual screening hits in shelve.

5. Screening of Experimental Activity

Experimental evaluation of the in vitro activity of virtual screening hits against amyloid fibril formation by TTR was carried out using a biochemical assay based on turbidimetry measurements. In this assay, fibril formation is induced by acidification of the solution to pH 4.4 after incubation with the hit compound to be tested. The amount of amyloid fibrils formed is monitored over 72 hours. Further details on the assay are provided in the "Evaluation of amyloid inhibition in vitro" subsection below.

Protein Expression and Purification

Recombinant human wild-type TTR was expressed in BL21 (DE3) E. coli cells (NZYTech) transformed with pET23a plasmid containing the TTR and ampicillin-resistance genes. The transformed cells were grown in Luria Broth and the TTR expression was achieved by induction with 1 mM IPTG for 4 hours. After cell harvesting and a freeze/thaw cycle, the cells are sonicated and the insoluble materials pelleted by centrifugation. The protein purification protocol comprises an initial precipitation step with ammonium sulphate, followed by anionic exchange chromatography and size exclusion chromatography.

The concentrations of TTR solutions were determined spectrophotometrically at 280 nm, using an extinction coefficient of $7.76 \times 10^4$ $M^{-1}.cm^{-1}$, based on a 55 kDa molecular mass for the TTR tetramer [40].

Evaluation of Amyloid Inhibition In Vitro

Purchased virtual screening hits and all synthesized (optimization) derivatives were dissolved in DMSO to a final concentration of 10.8 mM to provide a primary stock solution. Several secondary stock solutions were prepared in DMSO by dilution of the primary stock solution and the concentrations were chosen depending on the effectiveness of the compound in inhibiting the TTR amyloid fibril formation.

The fibril formation assay was adapted to run in a high-throughput screening mode. For this purpose, 96-well microplates were used with a final assay volume of 100 µL.

One microLitre (µL) of different compound secondary stock solutions was added to 50 µL of a 7.2 µM wild type TTR (WT-TTR) or Val122Ile-TTR (V122I-TTR) solutions in 10 miliMolar (mM) sodium phosphate buffer, 100 mM KCl and 1 mM EDTA, pH 7.2, previously dialyzed against the same buffer solution. After 30 minutes of incubation at room temperature, the pH of the mixture was lowered to 4.4 with 49 µL of 200 mM acetate buffer, 100 mM KCl and 1 mM EDTA, pH 4.3. The final 100 µL solutions have DMSO 1%, 3.6 µM of TTR and a variety of compound concentrations which may range between 0.72 µM (0.2×TTR) to 36 µM (10×TTR).

The mixtures were incubated at 37° C. during 72 hours. Turbidity at 405 nm, 450 nm and 490 nm (or at 550, 600 and 650 nm when the test compound absorbs light at the previous wavelengths) was measured over time (0, 17, 24, 41, 48, 65 and 72 hours) using a BioTek Microplate Spectrophotometer to evaluate the extent of fibril formation. Immediately before the turbidity measurements, the mixtures were gently shacked during 1 minute to homogenize well and not damage the formed amyloid aggregates and fibrils. The final turbidity was calculated as an average of the three wavelengths measured.

In addition, control samples containing TTR with no inhibitor and 1% DMSO, as well as inhibitor in absence of TTR were tested and analyzed.

All compounds were found to be soluble throughout the course of the experiment, ensuring that turbidity was the result of TTR amyloid fibril formation.

The extent of amyloid fibril formation data was normalized to TTR in the absence of inhibitor, assigned to be 100% fibril formation (or 0% amyloid inhibition) at the end of the experiment.

Determination of $IC_{50}$

The concentration of test compounds that inhibited transsthyretin amyloid fibril formation by 50% (here denoted as $IC_{50}$) was determined by monitoring the effect of increasing concentrations of the compounds on the inhibition patterns. Ten different compound concentrations were used for each $IC_{50}$ determination, while TTR concentration was kept fixed at 3.6 µM. The extent of amyloid fibril formation throughout 72 hours was determined as described in the "Evaluation of amyloid inhibition in vitro" subsection above.

$IC_{50}$ values were calculated from the inhibition curves obtained by fitting the values by a nonlinear curve method using the OriginPro7 (OriginLab Corporation, USA).

Thyroxine Competition Assays by Gel Electrophoresis

The assay for the binding to TTR through competition with T4 is performed by T4 binding gel electrophoresis as previously described in reference [23].

Five (5) µL of human plasma plus 0.25-0.5 µL of [125I]T4 (specific radioactivity 1250 µCi/m; concentration 320 µCi/mL; Perkin Elmer, Boston, Mass., U.S.A.) plus 5 µL of PBS with glycerol 50% are incubated for 1 hour at room temperature (RT) and the samples are subjected to native PAGE. After electrophoresis, the gels are dried, subjected to phosphor imaging (Typhoon 8600; Molecular Diagnostics, Amersham Biosciences), and analyzed using the ImageQuant program version 5.1. The intensity of the protein bands is compared. Two or three bands of different intensity should be visualized in plasma samples.

The bands correspond to the major T4-binding plasma proteins, namely albumin (ALB), transthyretin (TTR) and thyroxine-binding globulin (TBG). The intensity of the bands should be decreased, as compared to the control samples (absence of compound), if the compound binds to the protein(s) competing with T4.

The results are analyzed by calculation of the TTR/total (TTR+ALB+TBG) ratio for each sample collected at different time points. The displacement of T4 from TTR is calculated as the difference between the average of ratios of TTR/total protein for each control sample and the average of the ratios of TTR/total protein.

Evaluation of Tetrameric TTR Stability by IEF

TTR stability is assessed by isoelectric focusing (IEF) of plasma TTR as described in references [23,24]. To perform the assay, 30 µL of human plasma are incubated with 5 µL of a 10 mM solution of test compounds and control compounds overnight at 4° C. followed by a 1 hour incubation at RT. The preparations are subjected to native PAGE and the gel band containing TTR is excised and applied to an IEF gel. IEF is carried out in semi-denaturing conditions (4 M urea), containing 5% (v/v) ampholytes pH 4-6.5 (GE Healthcare), at 1200 V for 6 hours. Proteins are stained with Coomassie Blue, the gels are scanned and subjected to densitometry using the ImageQuant program. The results are expressed as the ratio of TTR tetramer over total TTR.

Experimental Evaluation of Cytotoxicity of Compounds Using Cell-Based Assays

Preliminary toxicology was conducted on AT50 compounds throughout lead series expansion and optimization was based on the use of theoretical cheminformatics approaches and workflows powered by Derek Nexus (Lhasa Limited) but also on the experimental evaluation of the cytotoxicity of the most active optimization derivatives using cell-based assays. Here, we describe the procedures to conduct such evaluation.

Cell Culture

Adherent human hepatoma cells HepG2 were cultured in DMEM (Dulbecco's Modified Eagle's Medium) with 10% fetal bovine serum (FBS), 100 U/mL penicillin, 100m/mL streptomycin, and 1 mM sodium pyruvate. The cells were grown in 75 cm² culture flasks at 37° C., in an atmosphere of 5% $CO_2$, and subcultured twice a week using a trypsin-EDTA solution.

Cell-Based Assay

Upon 3 to 4 days of growth and reaching approximately 90% confluence, HepG2 cells were plated in 96-well microplates with cell density of 12×103 cells/well and in a volume of 100 µL per well. Preliminary studies indicated that this cell density is optimal for HepG2 cells show a linear increase over 72 hours of incubation at 37° C. and 5% $CO_2$.

The compounds are dissolved in DMSO and subsequently diluted in DMEM (in 9 intermediate cell concentrations). After adhesion of HepG2 cells to the microplates, more than 100 µL of each solution of intermediate compound concentration were added to each well (in quadruplicate). Positive controls were done with 10 wells containing only cells; solvent controls resulted from the analysis of the three highest DMSO concentrations tested and were carried out in triplicate.

After addition of the compounds to the cells, the microplates were incubated for approximately 72 hours at 37° C. in an atmosphere of 5% $CO_2$ until the cell viability assay was performed.

Cytotoxicity Assay

The cell viability of HepG2 cells in the presence of test compounds was assessed by the resazurin reduction assay. Resazurin is a redox indicator that is converted into resorufin through reduction reactions of metabolically active cells. In the oxidized form it presents a purplish blue color, while the reduced form presents a purple-pink color.

A stock solution of 0.01% resazurin in PBS is diluted 1:10 in incomplete RPMI 1640 cell medium (without addition of antibiotics and FBS). After washing the cells with 200 µL PBS containing $Ca^{2+}$ and $Mg^{2+}$, 200 µL of resazurin 0.001% are added to the wells. Control runs with incomplete RPMI 1640 medium only and (without cells) are done in triplicate. The microplates are incubated at 37° C. and 5% $CO_2$ for approximately 2 to 4 hours.

To quantify the reduction of resazurin to resorufin, microplate absorbance readings were taken at two wavelengths, 540 nm (reduced form) and 630 nm (oxidized form), in a Biotek spectrophotometer microplate reader. The percentage of viable cells at each compound concentration is determined using the formula:

$$\% \text{ viable cells} = \frac{(\varepsilon_{630\,nm} \times Abs_{540\,nm}) - (\varepsilon_{540\,nm} \times Abs_{630\,nm})}{(\varepsilon_{630\,nm} \times Ctrl_{540\,nm}) - (\varepsilon_{540\,nm} \times Ctrl_{630\,nm})}$$

where ε is the molar extinction coefficient, Abs is the absorbance and Ctrl is the absorbance of the positive control (cells without compound).

Determination of $ID_{50}$ $ID_{50}$ values express the inhibitory dose of each test compound at 50% dose-response curve and were determined by nonlinear least square fitting to the experimental points using the program OriginPro7 (OriginLab Corporation, USA).

Experimental Procedures for the Preparation of Compounds

Most compounds belonging to the AT50 lead series were synthesized through a simple, fast and reliable microwave-assisted method, excellent isolated yields being obtained with minimal purification protocols (FIG. 1). Compounds with codes AT50-A50, AT50-A51, AT50-B00, AT50-B01, AT50-C00, AT50-C01, AT50-C02, as well as the E stereoisomer of the original virtual screening hit AT50-A00, were commercially acquired and used as received.

Regarding compounds with codes AT50-A01, AT50-A03, AT50-A05, AT50-A06, AT50-A11, AT50-A12, AT50-A35, AT50-A47, AT50-C09, AT50-C10 and AT-50-C15, the aldehyde starting materials were previously prepared via known methodologies, as shown in Scheme 1 and Scheme 2 of FIG. 2. Regarding compound AT50-A49, the thiazolidinedione starting material was previously prepared via known methodologies, as shown in Scheme 3 of FIG. 2. Regarding compounds with codes AT50-C09, AT50-C10 and AT50-C11, the rhodanine starting material was previously prepared via a known methodology (FIG. 3).

Example 8

General Procedure for the Synthesis of Compounds AT50-A01, AT50-A03, AT50-A05, AT50-A06, AT50-A11, AT50-A12, AT50-A17, AT50-A35 and AT50-A47

A mixture of the selected aldehyde (1.5 mmol), 3-hydroxycarbonylmethyl-2-thioxothiazolidin-4-one (1.5 mmol, 293 mg) and anhydrous sodium acetate (4.5 mmol, 373 mg) in glacial acetic acid (1.5 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid. See, e.g., FIG. 1.

Example 9

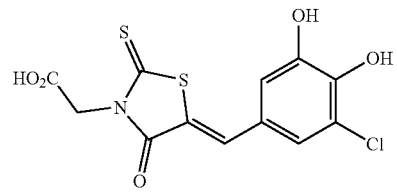

(Z)-5-(3'-chloro-4',5'-dihydroxyphenylmethylidene)-3-hydroxycarbonylmethyl-2-thioxothiazolidin-4-one, AT50-A01

Yield: 83%, 430 mg; mp (° C.): 241-242; FT-IR (v, cm⁻¹): 3195, 2984, 2942, 1742, 1733, 1682, 1588, 1568, 1493, 1418, 1407, 1321, 1282, 1183, 1109, 1064, 1012, 977, 949, 912, 880, 837, 815, 740, 705, 687, 612, 556, 542; UV-vis ($CH_3OH$): $\lambda_{max}$, nm (relative absorbance, %)=269 (37.6), 290 (43.7), 400 (100) 476 (18.2); ¹H NMR (400 MHz, $(CD_3)_2SO/CCl_4$): δ, ppm=10.13 (1H, bs, OH), 9.95 (1H, bs, OH), 7.62 (1H, s, CH), 7.10 (1H, s, ArH), 7.01 (1H, s, ArH), 4.69 (2H, s, $CH_2$); ¹³C NMR (100 MHz, $(CD_3)_2SO/CCl_4$): δ, ppm=192.5, 166.7, 166.1, 146.9, 145.6, 133.3, 124.4, 124.0, 121.0, 118.7, 114.7, 44.5; HR-MS (ESI): m/z=345.96020 ([M+H]⁺, $C_{12}H_9ClNO_5S_2$ required 345.96052).

Example 10

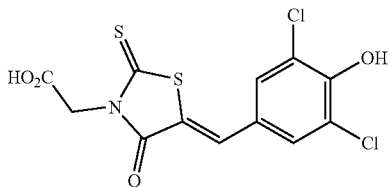

(Z)-3-hydroxycarbonylmethyl-5-(3',5'-dichloro-4'-hydroxyphenylmethylidene)-2-thioxothiazolidin-4-one, AT50-A03

Yield: 88%, 480 mg; mp (° C.): 262-264; UV-vis (CH$_3$OH): $\lambda_{max}$, nm (relative absorbance, %)=269.5 (100), 466.5 (51.3); $^1$H NMR (400 MHz, (CD$_3$)$_2$SO): δ, ppm=7.79 (1H, s, CH), 7.66 (2H, s, ArH), 4.73 (2H, s, CH$_2$); $^{13}$C NMR (100 MHz, (CD$_3$)$_2$SO): δ, ppm=192.5, 167.2, 166.2, 151.7, 131.6, 130.8, 125.6, 122.9, 120.9, 45.0; HR-MS (ESI): m/z=363.92655 ([M+H]$^+$, C$_{12}$H$_8$C$_{12}$NO$_4$S$_2$ required 363.92663).

Example 11

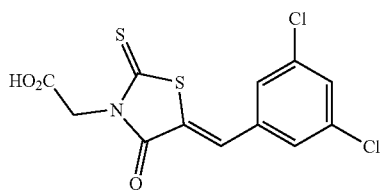 [SMILES: O=C(O)CN1C(=O)/C(=C/c2cc(Cl)cc(Cl)c2)SC1=S]

(Z)-3-hydroxycarbonylmethyl-5-(3',5'-dichlorophenylmethylidene)-2-thioxothiazolidin-4-one, AT-50-A05-Z Yield: 95%, 495 mg; mp (° C.): 272-273; $^1$H NMR (400 MHz, (CD$_3$)$_2$SO/CCl$_4$): δ, ppm=7.84 (1H, s, CH), 7.63 (1H, s, ArH), 7.62 (2H, s, ArH), 4.70 (2H, s, CH$_2$); $^{13}$C NMR (100 MHz, (CD$_3$)$_2$SO/CCl$_4$): δ, ppm=192.1, 166.8, 165.9, 136.3, 135.1, 130.3, 129.8, 128.3, 125.3, 45.0; HR-MS (ESI): m/z=369.91440 ([M+Na]$^+$, C$_{12}$H$_7$Cl$_2$NNaO$_3$S$_2$ required 369.91366).

Example 12

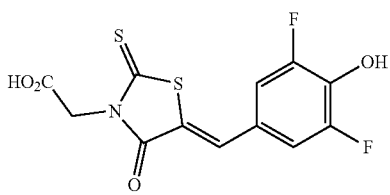

(Z)-3-hydroxycarbonylmethyl-5-(3',5'-difluoro-4'-hydroxyphenylmethylidene)-2-thioxothiazolidin-4-one, AT50-A06

Yield: 89%, 445 mg; mp (° C.): 221-222; UV-vis (CH$_3$OH): $\lambda_{max}$, nm (relative absorbance, %)=302 (41.5), 458 (100); $^1$H NMR (400 MHz, (CD$_3$)$_2$SO/CCl$_4$): δ, ppm=7.71 (1H, s, CH), 7.21 (2H, d, J=7.6 Hz, ArH), 4.69 (2H, s, CH$_2$); $^{13}$C NMR (100 MHz, (CD$_3$)$_2$SO/CCl$_4$): δ, ppm=191.9, 166.6, 166.1, 152.3 (dd, J=243.4 and 7.6 Hz), 137.4 (t, J=16.2 Hz), 131.9, 122.8 (t, J=8.7 Hz), 120.7, 113.9 (dd, J=15.0 and 7.2 Hz), 44.5; HR-MS (ESI): m/z=331.98565 ([M+H]$^+$, C$_{12}$H$_8$F$_2$NO$_4$S$_2$ required 331.98573).

Example 13

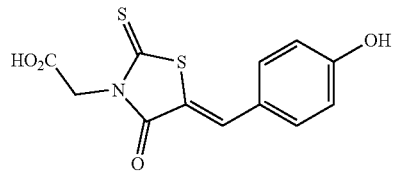 [SMILES: O=C(O)CN1C(=O)/C(=C/c2ccc(O)cc2)SC1=S]

(Z)-3-hydroxycarbonylmethyl-5-(4'-hydroxyphenylmethylidene)-2-thioxothiazolidin-4-one, AT50-A11

Yield: 65%, 290 mg; mp (° C.): 213-214; FT-IR (ν, cm$^{-1}$): 3375, 2975, 2937, 1700, 1598, 1576, 1509, 1441, 1405, 1366, 1350, 1312, 1277, 1261, 1213, 1189, 1174, 1122, 1115, 1096, 1061, 951, 897, 820, 799, 740, 733, 716, 682, 628, 608, 548, 540, 522, 495; UV-vis (CH$_3$OH): $\lambda_{max}$, nm (relative absorbance, %)=288.5 (41.3), 395.5 (100); $^1$H NMR (400 MHz, (CD$_3$)$_2$SO/CCl$_4$): δ, ppm=7.70 (1H, s, CH), 7.42 (2H, d, J=8.4 Hz, ArH), 6.89 (2H, d, J=8.4 Hz, ArH), 4.68 (2H, s, CH$_2$); $^{13}$C NMR (100 MHz, (CD$_3$)$_2$SO/CCl$_4$): δ, ppm=192.6, 166.8, 166.3, 160.8, 134.3, 132.9, 123.7, 117.2, 116.4, 44.5; HR-MS (ESI): m/z=296.00447 ([M+H]$^+$, C$_{12}$H$_{10}$NO$_4$S$_2$ required 296.00458).

Example 14

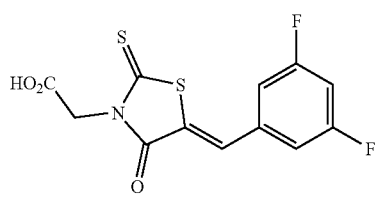 [SMILES: O=C(O)CN1C(=O)/C(=C/c2cc(F)cc(F)c2)SC1=S]

(Z)-3-hydroxycarbonylmethyl-5-(3',5'-difluorophenylmethylidene)-2-thioxothiazolidin-4-one, AT50-A12

Yield: 93%, 440 mg; mp (° C.): 225-227; $^1$H NMR (400 MHz, (CD$_3$)$_2$SO/CCl$_4$): δ, ppm=7.83 (1H, s, CH), 7.24 (2H, d, J=6.4 Hz, ArH), 7.09 (1H, t, J=8.8 Hz, ArH), 4.71 (2H, s, CH$_2$); $^{13}$C NMR (100 MHz, (CD$_3$)$_2$SO/CCl$_4$): δ, ppm=191.7, 166.5, 165.9, 162.7 (dd, J=248, 12.8), 136.2 (t, J=9.8), 130.6, 125.1, 112.9 (dd, J=19.1 and 7.3 Hz), 105.6 (t, J=25.6 Hz), 44.6; HR-MS (ESI): m/z=315.99078 ([M+H]$^+$, C$_{12}$H$_8$F$_2$NO$_3$S$_2$ required 315.99082).

Example 15

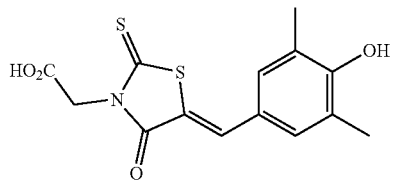 [SMILES: Cc1cc(/C=C2\SC(=S)N(CC(=O)O)C2=O)cc(C)c1O]

(Z)-3-hydroxycarbonylmethyl-5-(4'-hydroxy-3',5'-dimethylphenylmethylidene)-2-thioxothiazolidin-4-one, AT50-A17

Yield: 88%, 425 mg; mp (° C.): 261-263; UV-vis (CH$_3$OH): $\lambda_{max}$, nm (relative absorbance, %)=266 (34.7), 291.5 (41.9), 403 (100); $^1$H NMR (400 MHz, (CD$_3$)$_2$SO/CCl$_4$): δ, ppm=7.64 (1H, s, CH), 7.17 (2H, s, ArH), 4.69 (2H, s, CH$_2$), 2.25 (6H, s, CH$_3$); $^{13}$C NMR (100 MHz, (CD$_3$)$_2$SO/CCl$_4$): δ, ppm=192.7, 166.8, 166.3, 157.1, 134.5, 131.6, 125.2, 123.8, 117, 44.5, 16.6; HR-MS (EI): m/z=323.0286 (M$^+$, C$_{14}$H$_{13}$NO$_4$S$_2$ required 323.0286).

Example 16

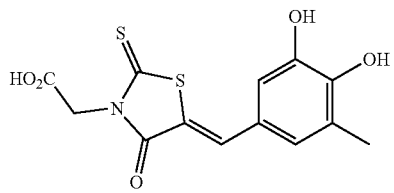 [SMILES: Cc1cc(/C=C2\SC(=S)N(CC(=O)O)C2=O)cc(O)c1O]

(Z)-5-(3',4'-dihydroxy-5'-methylphenylmethylidene)-3-hydroxycarbonylmethyl-2-thioxothiazolidin-4-one, AT50-A35

Yield: 80%, 390 mg; mp (° C.): 238-239; FT-IR (v, cm$^{-1}$): 3206, 3016, 2736, 2620, 2539, 1728, 1683, 1581, 1496, 1455, 1425, 1395, 1387, 1357, 1321, 1281, 1242, 1188, 1110, 1061, 1049, 972, 941, 916, 868, 832, 808, 729, 703, 692, 632, 612, 560, 544, 525; UV-vis (CH$_3$OH): $\lambda_{max}$, nm (relative absorbance, %)=270 (34.3), 291.5 (42.9), 416 (100); $^1$H NMR (400 MHz, (CD$_3$)$_2$SO/CCl$_4$): δ, ppm=9.62 (1H, bs, OH), 9.00 (1H, bs, OH), 7.59 (1H, s, CH), 6.92 (1H, d, J=2.0 Hz, ArH), 6.86 (1H, d, J=2.0 Hz, ArH), 4.69 (2H, s, CH$_2$), 2.21 (3H, s, CH$_3$); $^{13}$C NMR (100 MHz, (CD$_3$)$_2$SO/CCl$_4$): δ, ppm=192.9, 166.8, 166.3, 147.9, 145.3, 135.0, 126.4, 125.3, 123.3, 116.7, 114.4, 44.4, 15.8; HR-MS (EI): m/z=325.0069 (M$^+$, C$_{13}$H$_{11}$NO$_5$S$_2$ required 325.0079).

Example 17

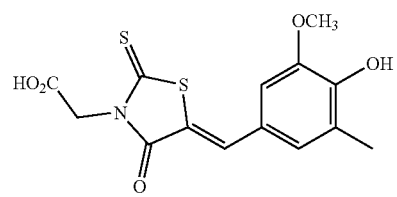 [SMILES: COc1cc(/C=C2\SC(=S)N(CC(=O)O)C2=O)cc(C)c1O]

(Z)-3-hydroxycarbonylmethyl-5-(4'-hydroxy-3'-methoxy-5'-methylphenylmethylidene)-2-thioxothiazolidin-4-one, AT50-A47

Yield: 85%, 430 mg; mp (° C.): 238-239; UV-vis (CH$_3$OH): $\lambda_{max}$, nm (relative absorbance, %)=267 (34.1), 293 (41.7), 411 (100); $^1$H NMR (400 MHz, (CD$_3$)$_2$SO/CCl$_4$): δ, ppm=9.26 (1H, bs, OH), 7.69 (1H, s, CH), 6.98 (2H, s, ArH), 4.69 (2H, s, CH$_2$), 3.91 (3H, s, OCH$_3$), 2.24 (3H, s, CH$_3$); $^{13}$C NMR (100 MHz, (CD$_3$)$_2$SO/CCl$_4$): δ, ppm=192.5, 166.7, 166.2, 148.4, 147.4, 134.7, 126.9, 125.2, 123.4, 117.2, 111.6, 55.7, 44.4, 15.7; HR-MS (ESI): m/z=340.03079 ([M+H]$^+$, C$_{14}$H$_{14}$NO$_5$S$_2$ required 340.03079).

Example 18

General Procedure for the Synthesis of Compound AT50-A49

A mixture of 3,5-dichloro-4-hydroxybenzaldehyde (0.75 mmol, 145 mg), 3-hydroxycarbonylmethyl-2,4-dioxothiazolidine (0.75 mmol, 134 mg) and anhydrous sodium acetate (2.25 mmol, 187 mg) in glacial acetic acid (0.75 mL) was thoroughly mixed in an appropriate 10 mL thick-walled glass vial. This was tightly sealed with a Teflon cap and the reaction mixture was stirred and heated at 140° C. for 30 minutes, under focused microwave irradiation, with an initial power setting of 75 W. After cooling to room temperature, the crude product mixture was poured over distilled water and crushed-ice and the yellowish solid that precipitated was filtered under reduced pressure, washed with distilled water, recrystallized from dichloromethane and dried at room temperature under vacuum, yielding the desired compound as a yellow solid.

Example 19

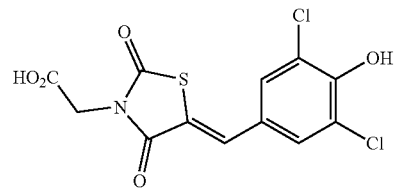 [SMILES: O=C(O)CN1C(=O)S/C(=C\c2cc(Cl)c(O)c(Cl)c2)C1=O]

(Z)-5-(3',5'-dichloro-4'-hydroxyphenylmethylidene)-3-hydroxycarbonylmethyl-2,4-dioxothiazolidine, AT50-A49

Yield: 57%, 150 mg; mp (° C.): 256-258; FT-IR (v, cm$^{-1}$): 3480, 3070, 2990, 2945, 1753, 1712, 1686, 1605, 1584, 1557, 1485, 1443, 1404, 1372, 1311, 1296, 1250, 1218, 1152, 1095, 1007, 969, 911, 856, 808, 774, 740, 715, 705, 684, 600, 560, 523; UV-vis (CH$_3$OH): $\lambda_{max}$, nm (relative absorbance, %)=219 (77.6), 248 (58.7), 342.5 (100); $^1$H NMR (400 MHz, (CD$_3$)$_2$SO): δ, ppm=7.90 (1H, s, CH), 7.67 (2H, s, ArH), 4.38 (2H, s, CH$_2$); $^{13}$C NMR (100 MHz, (CD$_3$)$_2$SO): 0.3, ppm=167.9, 166.4, 164.8, 151.4, 131.6, 130.3, 125.6, 122.9, 119.9, 42.3); HR-MS (ESI): m/z=347.94914 ([M+H]$^+$, C$_{12}$H$_8$Cl$_2$NO$_5$S required 347.94947).

Example 20

General Procedure for the Synthesis of Compounds AT50-C09, AT50-C10 and AT50-C11

A mixture of the selected aldehyde (1.5 mmol), 3-(3'-hydroxycarbonylpropyl)-2-thioxothiazolidin-4-one (1.5 mmol, 332 mg) and anhydrous sodium acetate (4.5 mmol, 373 mg) in glacial acetic acid (1.5 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid. See, e.g., FIG. 1.

Example 21

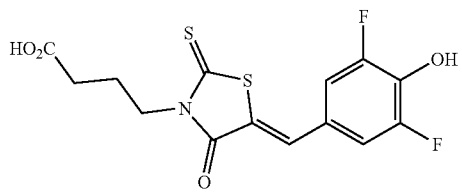

(Z)-5-(3',5'-difluoro-4'-hydroxyphenylmethylidene)-3-(3'-hydroxycarbonylpropyl)-2-thioxothiazolidin-4-one, AT50-C09

Yield: 85%, 460 mg; mp (° C.): 207-209; UV-vis (CH$_3$OH): $\lambda_{max}$, nm (relative absorbance, %)=301 (38.6), 461.5 (100); $^1$H NMR (400 MHz, (CD$_3$)$_2$SO/CCl$_4$): δ, ppm=7.64 (1H, s, CH), 7.18 (2H, d, J=7.2 Hz, ArH), 4.12 (2H, t, J=7.0 Hz, NCH$_2$CH$_2$CH$_2$CO$_2$H), 2.28 (2H, t, J=7.0 Hz, NCH$_2$CH$_2$CH$_2$CO$_2$H), 1.92-1.97 (2H, m, NCH$_2$CH$_2$CH$_2$CO$_2$H); $^{13}$C NMR (100 MHz, (CD$_3$)$_2$SO/CCl$_4$): δ, ppm=192.2, 173.1, 166.7, 166.1, 152.2 (dd, J=243.4 and 7.5 Hz), 137.1 (t, J=16.1), 131.2, 122.9 (t, J=8.5 Hz), 121.1, 113.9 (dd, J=15.2 and 7.2 Hz), 43.5, 30.9, 22; HR-MS (EI): m/z=359.0095 (M$^+$, C$_{14}$H$_{11}$F$_2$NO$_4$S$_2$ required 359.0098).

Example 22

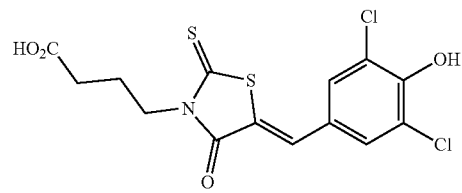 [SMILES: O=C(O)CCCN1C(=O)/C(=C/c2cc(F)c(O)c(F)c2)SC1=S]

(Z)-5-(3',5'-dichloro-4'-hydroxyphenylmethylidene)-3-(3'-hydroxycarbonylpropyl)-2-thioxothiazolidin-4-one, AT50-C10

Yield: 87%, 510 mg; mp (° C.): 247-249; UV-vis (CH$_3$OH): $\lambda_{max}$, nm (relative absorbance, %)=295.5 (57.6), 470 (100); $^1$H NMR (400 MHz, (CD$_3$)$_2$SO): δ, ppm=7.65 (1H, s, CH), 7.53 (2H, s, ArH), 4.11 (2H, t, J=6.8 Hz, NCH$_2$CH$_2$CH$_2$CO$_2$H), 2.28 (2H, t, J=6.8 Hz, NCH$_2$CH$_2$CH$_2$CO$_2$H), 1.91-1.94 (2H, m, NCH$_2$CH$_2$CH$_2$CO$_2$H); $^{13}$C NMR (100 MHz, (CD$_3$)$_2$SO): δ, ppm=192.2, 173.1, 166.7, 151.6, 130.5, 130.4, 125.5, 123.0, 121.2, 43.5, 30.9, 22.0; HR-MS (EI): m/z=390.9522 (M$^+$, C$_{14}$H$_{11}$Cl$_2$NO$_4$S$_2$ required 390.9507).

Example 23

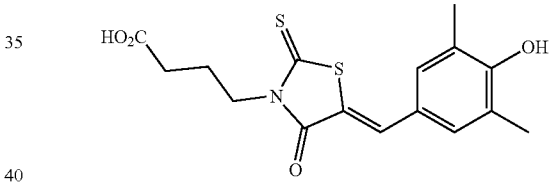

(Z)-5-(4'-hydroxy-3',5'-dimethylphenylmethylidene)-3-(3'-hydroxycarbonylpropyl)-2-thioxothiazolidin-4-one, AT50-C11

Yield: 87%, 460 mg; mp (° C.): 250-252; UV-vis (CH$_3$OH): $\lambda_{max}$, nm (relative absorbance, %)=266.5 (43.3), 290.5 (54.6), 408.5 (100); $^1$H NMR (400 MHz, (CD$_3$)$_2$SO/CCl$_4$): δ, ppm=7.57 (1H, s, CH), 7.14 (2H, s, ArH), 4.11 (2H, t, J=6.8 Hz, NCH$_2$CH$_2$CH$_2$CO$_2$H), 2.27 (2H, t, J=6.8 Hz, NCH$_2$CH$_2$CH$_2$CO$_2$H), 2.25 (6H, s, CH$_3$), 1.91-1.94 (2H, m, NCH$_2$CH$_2$CH$_2$CO$_2$H); $^{13}$C NMR (100 MHz, (CD$_3$)$_2$SO/CCl$_4$): δ, ppm=192.9, 173.1, 166.9, 157.0, 133.9, 131.5, 125.2, 123.9, 117.3, 43.3, 30.9, 22.1, 16.6; HR-MS (EI): m/z=351.0598 (M$^+$, C$_{16}$H$_{17}$NO$_4$S$_2$ required 351.0599).

Example 24

General Procedure for the Synthesis of Compounds AT50-C13, AT50-C14, AT50-C15, AT50-C16, AT50-C18, AT50-C19 and AT50-C20

A mixture of the selected aldehyde (0.75 mmol), 3-(2'-hydroxycarbonylethyl)-2-thioxothiazolidin-4-one (0.75 mmol, 159 mg) and anhydrous sodium acetate (2.25 mmol, 187 mg) in glacial acetic acid (0.75 mL) was thoroughly mixed in an appropriate 10 mL thick-walled glass vial. This was tightly sealed with a Teflon cap and the reaction mixture was stirred and heated at 140° C. for 5 minutes, under focused microwave irradiation, with an initial power setting of 75 W. After cooling to room temperature, the yellow solid that precipitated from the crude product mixture was washed with distilled water, filtered under reduced pressure, recrystallized from dichloromethane and dried at room temperature under vacuum, yielding the desired compound as a bright-yellow solid. See, e.g., FIG. 1.

Example 25

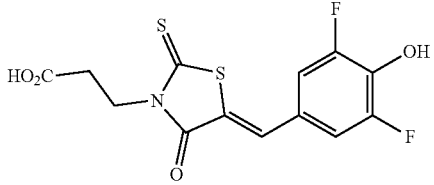

(Z)-5-(3',5'-difluoro-4'-hydroxyphenylmethylidene)-3-(2'-hydroxycarbonylethyl)-2-thioxothiazolidin-4-one, AT50-C13

Yield: 83%, 215 mg; mp (° C.): 216-217; FT-IR (v, cm$^{-1}$): 3512, 3012, 1691, 1585, 1520, 1441, 1429, 1386, 1314, 1253, 1218, 1171, 1152, 1106, 1075, 1025, 1005, 993, 937, 916, 873, 845, 792, 734, 710, 622, 597, 566, 557, 536, 500; UV-vis (CH$_3$OH): $\lambda_{max}$, nm (relative absorbance, %)=283 (70.3), 388 (100), 453 (17.2); $^1$H NMR (400 MHz, (CD$_3$)$_2$SO/CCl$_4$): δ, ppm=7.67 (1H, s, CH), 7.19 (2H, d, J=7.6 Hz, ArH), 4.27 (2H, t, J=7.8 Hz, NCH$_2$CH$_2$CO$_2$H), 2.61 (2H, t, J=7.8 Hz, NCH$_2$CH$_2$CO$_2$H); $^{13}$C NMR (100 MHz, (CD$_3$)$_2$SO/CCl$_4$): 0.3, ppm=191.9, 171.1, 166.3, 152.3 (dd, J=243.3 and 7.6 Hz), 137.1 (t, J=16.1 Hz), 131.4, 122.9 (t, J=8.6 Hz), 120.9, 113.9 (dd, J=15.2 and 7.4 Hz), 39.7, 30.6; HR-MS (EI): m/z=344.9946 (M$^+$, C$_{13}$H$_9$F$_2$NO$_4$S$_2$ required 344.9941).

Example 26

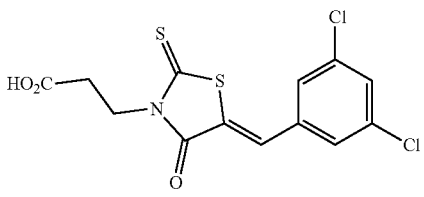 [SMILES: O=C(O)CCN1C(=O)/C(=C/c2cc(Cl)cc(Cl)c2)SC1=S]

(Z)-3-(2'-hydroxycarbonylethyl)-5-(3',5'-dichloro-phenylmethylidene)-2-thioxothiazolidin-4-one, AT-50-C14-Z Yield: 97%, 265 mg; mp (° C.): 245-247; $^1$H NMR (400 MHz, (CD$_3$)$_2$SO/CCl$_4$): δ, ppm=7.76 (1H, s, CH), 7.55 (2H, s, ArH), 7.51 (1H, s, ArH), 4.29 (2H, t, J=7.8, NCH$_2$CH$_2$CO$_2$H), 2.62 (2H, t, J=7.8, NCH$_2$CH$_2$CO$_2$H; $^{13}$C NMR (100 MHz, (CD$_3$)$_2$SO/CCl$_4$): δ, ppm=191.6, 171.1, 166.1, 136.4, 135.2, 129.4, 128.2, 125.6, 39.9, 30.6; HR-MS (EI): m/z=360.9408 (M$^+$, C$_{13}$H$_9$Cl$_2$NO$_3$S$_2$ required 360.9401).

Example 27

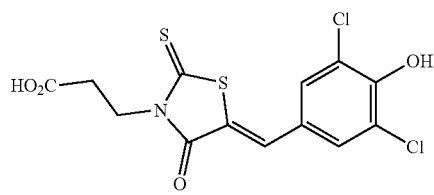 [SMILES: O=C(O)CCN1C(=O)/C(=C/c2cc(Cl)c(O)c(Cl)c2)SC1=S]

(Z)-3-(2'-hydroxycarbonylethyl)-5-(3',5'-dichloro-4'-hydroxyphenylmethylidene)-2-thioxothiazolidin-4-one, AT50-C15

Yield: 85%, 240 mg; mp (° C.): 259-260; UV-vis (CH$_3$OH): $\lambda_{max}$, nm (relative absorbance, %)=267.5 (59.4), 283.5 (62.8), 388 (100), 463.5 (25.3); $^1$H NMR (400 MHz, (CD$_3$)$_2$SO): δ, ppm=7.66 (1H, s, CH), 7.52 (2H, s, ArH), 4.26 (2H, t, J=7.6 Hz, NCH$_2$CH$_2$CO$_2$H), 2.61 (2H, t, J=7.6 Hz, NCH$_2$CH$_2$CO$_2$H); $^{13}$C NMR (100 MHz, (CD$_3$)$_2$SO): δ, ppm=191.8, 171.1, 166.3, 149.2, 130.7, 130.4, 125.2, 123.1, 120.9, 30.6; HR-MS (ESI): m/z=377.9430 ([M+H]$^+$, C$_{13}$H$_{10}$Cl$_2$NO$_4$S$_2$ required 377.9423).

Example 28

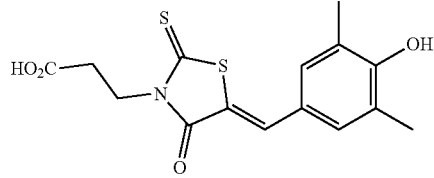 [SMILES: Cc1cc(/C=C2\SC(=S)N(CCC(=O)O)C2=O)cc(C)c1O]

(Z)-3-(2'-hydroxycarbonylethyl)-5-(4'-hydroxy-3',5'-dimethylphenylmethylidene)-2-thioxothiazolidin-4-one, AT50-C16

Yield: 85%, 215 mg; mp (° C.): 253-254; UV-vis (CH$_3$OH): $\lambda_{max}$, nm (relative absorbance, %)=267.5 (50.8), 288 (55.1), 404.5 (100); $^1$H NMR (400 MHz, (CD$_3$)$_2$SO): δ, ppm=7.58 (1H, s, CH), 7.14 (2H, s, ArH), 4.26 (2H, t, J=7.8 Hz, NCH$_2$CH$_2$CO$_2$H), 2.59 (2H, t, J=7.8 Hz, NCH$_2$CH$_2$CO$_2$H, 2.25 (6H, s, CH$_3$); $^{13}$C NMR (100 MHz, (CD$_3$)$_2$SO/CCl$_4$): δ, ppm=192.6 (C), 171.2, 166.6, 157.1, 134.1, 131.6, 125.2, 123.8, 117.2, 30.7, 16.6; HR-MS (EI): m/z=337.0450 (M$^+$, C$_{15}$H$_{15}$NO$_4$S$_2$ required 337.0443).

Example 29

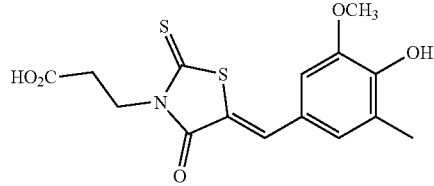 [SMILES: COc1cc(/C=C2\SC(=S)N(CCC(=O)O)C2=O)cc(C)c1O]

101

(Z)-5-(4'-hydroxy-3'-methoxy-5'-methylphenylmethylidene)-3-(2'-hydroxycarbonylethyl)-2-thioxothiazolidin-4-one, AT50-C18

Yield: 88%, 235 mg; mp (° C.): 194-196; FT-IR (v, cm$^{-1}$): 3150, 2958, 2838, 1710, 1675, 1601, 1575, 1497, 1462, 1418, 1380, 1351, 1309, 1287, 1203, 1163, 1105, 1083, 1065, 1012, 961, 947, 927, 919, 883, 856, 837, 807, 738, 724, 687, 617, 593, 564, 528, 515; UV-vis (CH$_3$OH): $\lambda_{max}$, nm (relative absorbance, %)=268 (39.6), 291 (45.6), 413 (100); $^1$H NMR (400 MHz, (CD$_3$)$_2$SO/CCl$_4$): δ, ppm=9.36 (1H, bs, OH), 7.65 (1H, s, CH), 6.97 (2H, d, J=6.4 Hz, ArH), 4.26 (2H, t, J=7.8 Hz, NCH$_2$CH$_2$CO$_2$H), 3.90 (3H, s, OCH$_3$), 2.60 (2H, t, J=7.8 Hz, NCH$_2$CH$_2$CO$_2$H), 2.23 (3H, s, CH$_3$); $^{13}$C NMR (100 MHz, (CD$_3$)$_2$SO/CCl$_4$): δ, ppm=192.6, 171.3, 166.6, 148.1, 147.5, 134.4, 126.7, 125.3, 123.5, 117.3, 111.8, 55.7, 30.7, 15.8; HR-MS (EI): m/z=353.0384 (M$^+$, C$_{15}$H$_{15}$NO$_5$S$_2$ required 353.0392).

Example 30

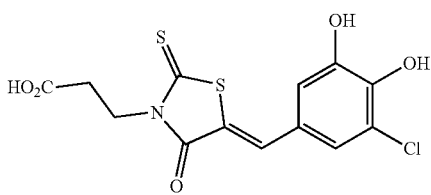 [SMILES: O=C(O)CCN1C(=O)/C(=C/c2cc(O)c(O)c(Cl)c2)SC1=S]

(Z)-5-(3'-chloro-4',5'-dihydroxyphenylmethylidene)-3-(2'-hydroxycarbonylethyl)-2-thioxothiazolidin-4-one, AT50-C19

Yield: 83%, 225 mg; mp (° C.): 243-245; FT-IR (v, cm$^{-1}$): 3440, 3018, 2929, 1711, 1691, 1588, 1570, 1496, 1459, 1414, 1363, 1339, 1317, 1269, 1227, 1172, 1130, 1110, 1072, 997, 953, 916, 878, 839, 792, 736, 696, 580, 561, 527; UV-vis (CH$_3$OH): $\lambda_{max}$, nm (relative absorbance, %)=271 (34.3), 289 (39.8), 401 (100); $^1$H NMR (400 MHz, (CD$_3$)$_2$SO/CCl$_4$): δ, ppm=10.01 (1H, bs, OH), 9.88 (1H, bs, OH), 7.54 (1H, s, CH), 7.04 (1H, d, J=1.8 Hz, ArH), 6.97 (1H, d, J=1.8 Hz, ArH), 4.27 (2H, t, J=8.0 Hz, NCH$_2$CH$_2$CO$_2$H), 2.60 (2H, t, J=8.0 Hz, NCH$_2$CH$_2$CO$_2$H); $^{13}$C NMR (100 MHz, (CD$_3$)$_2$SO/CCl$_4$): δ, ppm=192.4, 171.1, 166.4, 146.9, 145.5, 132.8, 124.3, 124.1, 121.0, 118.9, 114.7, 30.7; HR-MS (EI): m/z=358.9678 (M$^+$, C$_{13}$H$_{10}$ClNO$_5$S$_2$ required 358.9689).

Example 31

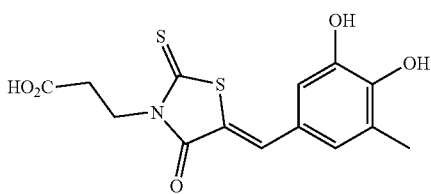

102

(Z)-5-(3',4'-dihydroxy-5'-methylphenylmethylidene)-3-(2'-hydroxycarbonylethyl)-2-thioxothiazolidin-4-one, AT50-C20

Yield: 81%, 250 mg; mp (° C.): 221-222; FT-IR (v, cm$^{-1}$): 3461, 3351, 3010, 2927, 1709, 1683, 1575, 1500, 1414, 1366, 1335, 1302, 1269, 1230, 1202, 1160, 1106, 1070, 1046, 983, 950, 920, 853, 831, 790, 731, 690, 619, 580, 565, 534; UV-vis (CH$_3$OH): $\lambda_{max}$, nm (relative absorbance, %)=266 (36.1), 292.5 (48.1), 416.5 (100); $^1$H NMR (400 MHz, (CD$_3$)$_2$SO/CCl$_4$): δ, ppm=9.62 (1H, bs, OH), 8.98 (1H, bs, OH), 7.54 (1H, s, CH), 6.90 (1H, d, J=2.0 Hz, ArH), 6.84 (1H, d, J=2.0 Hz, ArH), 4.26 (2H, t, J=7.8 Hz, NCH$_2$CH$_2$CO$_2$H), 2.59 (2H, t, J=7.8 Hz, NCH$_2$CH$_2$CO$_2$H), 2.20 (3H, s, CH$_3$); $^{13}$C NMR (100 MHz, (CD$_3$)$_2$SO/CCl$_4$): δ, ppm=192.7, 171.2, 166.5, 147.8, 145.3, 134.6, 126.3, 125.3, 123.4, 116.9, 114.4, 30.7, 15.8; HR-MS (EI): m/z=339.0231 (M$^+$, C$_{14}$H$_{13}$NO$_5$S$_2$ required 339.0235).

Example 32

General Procedure for the Synthesis of the Aldehyde Precursors

A solution of the selected phenol (10 mmol) and hexamethylenetetramine (11 mmol, 1.550 g) in trifluoroacetic acid (10 mL) was stirred and heated at reflux overnight. After cooling to room temperature, the crude product mixture was evaporated under reduced pressure and the yellow residue obtained was poured into distilled water and crushed ice. The cream-colored solid that precipitated was filtered under reduced pressure, washed with distilled water and dried at room temperature under vacuum, yielding the desired compound as a white solid. See, e.g., (Scheme 1, FIG. 2)

Example 33

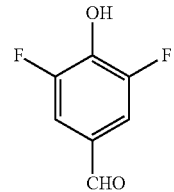 [SMILES: O=Cc1cc(F)c(O)c(F)c1]

3,5-Difluoro-4-hydroxybenzaldehyde

Yield: 60%, 940 mg; mp (° C.): 117-119 (Lit. 116-118, see reference [41]); [N. J. Lawrence, L. A. Hepworth, D. Rennison, A. T. McGown, J. A. Hadfield, Synthesis and anticancer activity of fluorinated analogues of combretastatin A-4, J. Fluor. Chem. 123 (2003) 101-108.] $^1$H NMR (400 MHz, CDCl$_3$): δ, ppm=9.81 (1H, s, CH), 7.49 (2H, d, J=7.2, ArH), 6.45 (1H, bs, OH); $^{13}$C NMR (100 MHz, CDCl$_3$): δ, ppm=189.1, 151.8 (dd, J=245.3 and 5.2 Hz), 139 (t, J=16.0 Hz), 128.1 (t, J=5.9 Hz), 113.2 (dd, J=14.7 and 6.8 Hz); GC-MS (EI): m/z (t$_R$, min)=158 (7.69) M$^+$.

Example 34

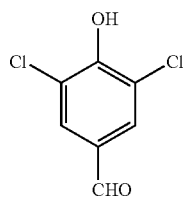 [SMILES: O=Cc1cc(Cl)c(O)c(Cl)c1]

3,5-Dichloro-4-hydroxybenzaldehyde

Yield: 90%, 1.715 g; mp (° C.): 153-155 (Lit. 154-156; see reference [42]); $^1$H NMR (400 MHz, CDCl$_3$): δ, ppm=9.81 (1H, s, CH), 7.83 (2H, s, ArH), 6.48 (1H, bs, OH); $^{13}$C NMR (100 MHz, CDCl$_3$): δ, ppm=188.4, 152.9, 130.2, 129.8, 122.2; GC-MS (EI): m/z (t$_R$, min)=190 (9.22) M$^+$.

Example 35

General Procedure for the Synthesis of the Aldehyde Precursor

To a stirred solution of aqueous formaldehyde (37% m/v, 37.5 mmol, 2.8 mL) and aqueous dimethylamine (40% m/v, 37.5 mmol, 4.8 mL) in ethanol (25 mL) was added 4-hydroxy-3-methoxybenzaldehyde (25 mmol, 3.883 g), the reaction mixture being stirred and heated at reflux for 45 minutes and then stirred at room temperature overnight. The cream-colored solid that precipitated was filtered under reduced pressure, washed with ice-cold acetone and dried at room temperature under vacuum, yielding 3-((dimethylamino)methyl)-4-hydroxy-5-methoxybenzaldehyde as an off-white solid. See, e.g., (Scheme 2, FIG. 2)

Example 36

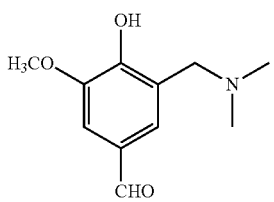

3-((Dimethylamino)methyl)-4-hydroxy-5-methoxybenzaldehyde

Yield: 75%, 3.910 g; mp (° C.): 140-142 (Lit. 139-141; see reference [43]); $^1$H NMR (400 MHz, CDCl$_3$): δ, ppm=10.6 (1H, bs, OH), 9.77 (1H, s, CH), 7.34 (1H, s, ArH), 7.15 (1H, s, ArH), 3.94 (3H, s, OCH$_3$), 3.76 (2H, s, CH$_2$), 2.38 (6H, s, 2×CH$_3$); $^{13}$C NMR (100 MHz, CDCl$_3$): δ, ppm=190.7, 154.5, 148.6, 128.1, 125.3, 121.4, 109.8, 62.2, 56, 44.3.

A solution of 3-((dimethylamino)methyl)-4-hydroxy-5-methoxybenzaldehyde (10 mmol, 2.100 g) in acetic anhydride (10 mL) was stirred and heated at reflux, under moisture exclusion conditions, for 24 hours. The reaction mixture was evaporated under reduced pressure and the brown-reddish residue obtained was diluted with aqueous hydrochloric acid (37% m/v, 10 mL) and stirred at room temperature for 2 hours. The cream-colored solid that precipitated was dissolved with 1,4-dioxane (10 mL) and stannous chloride dihydrate (30 mmol, 6.978 g) was added, the reaction mixture being stirred and heated at reflux for 45 minutes. After cooling to room temperature, the crude product mixture was washed with aqueous hydrochloric acid (10% m/v) and extracted with dichloromethane. The organic fraction was collected, dried with anhydrous sodium sulfate, filtered and evaporated under reduced pressure. The dark residue obtained was purified through silicon dioxide flash column chromatography, using diethyl ether/n-hexane (2:1 v/v) and diethyl ether as eluant. The aldehyde-containing fraction was collected, evaporated under reduced pressure and dried at room temperature under vacuum, yielding 4-hydroxy-3-methoxy-5-methylbenzaldehyde as a yellow solid.

Example 37

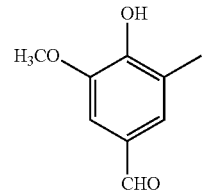

4-Hydroxy-3-methoxy-5-methylbenzaldehyde

Yield: 56%, 935 mg; mp (° C.): 98-100 (Lit. 99-101; see reference [43]); $^1$H NMR (400 MHz, CDCl$_3$): δ, ppm=9.79 (1H, s, CH), 7.30 (1H, s, ArH), 7.28 (1H, s, ArH), 6.27 (1H, bs, OH), 3.95 (3H, s, OCH$_3$), 2.32 (3H, s, CH$_3$); $^{13}$C NMR (100 MHz, CDCl$_3$): δ, ppm=191.2, 149.7, 146.7, 128.9, 128.8, 124.1, 106.7, 56.2, 15.3; GC-MS (EI): m/z (t$_R$, min)=166 (10.24) M$^+$.

To a stirred solution of 4-hydroxy-3-methoxy-5-methylbenzaldehyde (5 mmol, 835 mg) in dichloromethane (20 mL) at 0° C. was added drop-wise (10-15 minutes) a solution of boron tribromide in dichloromethane (1 M, 15 mmol, 15 mL), the reaction mixture being stirred, under moisture exclusion conditions, at 0° C. for one hour and then at room temperature overnight. After cooling to 0° C., the crude product mixture was carefully washed with distilled water and the organic layer was evaporated under reduced pressure. The dark solid that precipitated was filtered under reduced pressure, washed with distilled water and purified through silicon dioxide flash column chromatography, using dichloromethane/ethyl acetate (7:3 and 1:1 v/v) as eluant. The aldehyde-containing fraction was collected, evaporated under reduced pressure, recrystallized from diethyl ether and dried at room temperature under vacuum, yielding 3,4-dihydroxy-5-methylbenzaldehyde as a reddish-brown solid.

Example 38

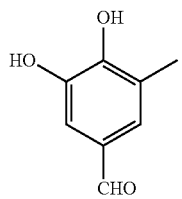

3,4-Dihydroxy-5-methylbenzaldehyde

Yield: 75%, 570 mg; mp (° C.): 199-202 (Lit. 196-198, see M. F. Ansell, A. J. Bignold, A. F. Gosden, V. J. Leslie, R. A. Murray, The Diels-Alder reactions of o-benzoquinones with acyclic dienes, J. Chem. Soc. C. (1971) 1414. doi: 10.1039/j39710001414, the entire contents of which are incorporated herein by reference); $^1$H NMR (400 MHz, $(CD_3)_2SO/CCl_4$): δ, ppm=9.62 (1H, s, CH), 9.55 (1H, bs, OH), 8.87 (1H, bs, OH), 7.10 (1H, s, ArH), 7.08 (1H, s, ArH), 2.22 (3H, s, $CH_3$); $^{13}$C NMR (100 MHz, $(CD_3)_2SO/CCl_4$): δ, ppm=189.9, 150.1, 144.9, 127.7, 125.5, 124.3, 111.9, 15.7; GC-MS (EI): m/z ($t_R$, min)=152 (9.90) M$^+$.

To a stirred solution of 3-chloro-4-hydroxy-5-methoxybenzaldehyde (5 mmol, 972 mg) in dichloromethane (20 mL) at 0° C. was added drop-wise (10-15 minutes) a solution of boron tribromide in dichloromethane (1 M, 15 mmol, 15 mL), the reaction mixture being stirred, under moisture exclusion conditions, at 0° C. for one hour and then at room temperature overnight. After cooling to 0° C., the crude product mixture was carefully washed with distilled water and the organic layer was evaporated under reduced pressure. The pinkish solid that precipitated was filtered under reduced pressure, washed with distilled water and dried at room temperature under vacuum, yielding 3-chloro-4,5-dihydroxybenzaldehyde as a pale-pink solid.

Example 39

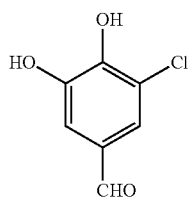 [SMILES: O=Cc1cc(O)c(O)c(Cl)c1]

3-Chloro-4,5-dihydroxybenzaldehyde

Yield: 73%, 630 mg; mp (° C.): 219-221; $^1$H NMR (400 MHz, $(CD_3)_2SO/CCl_4$): δ, ppm=10.10 (1H, bs, OH), 9.97 (1H, bs, OH), 9.66 (1H, s, CH), 7.31 (1H, s, ArH), 7.19 (1H, s, ArH); $^{13}$C NMR (100 MHz, $(CD_3)_2SO/CCl_4$): δ, ppm=189.3, 148.3, 146.6, 128.1, 123.7, 120.4, 112.7; GC-MS (EI): m/z ($t_R$, min)=172 (9.49) M$^+$.

Example 40

General Procedure for the Synthesis of the Rhodanine Precursor

To a stirred solution of γ-aminobutyric acid (50 mmol, 5.315 g) and sodium hydroxide (50 mmol, 2.041 g) in distilled water (50 mL) was added carbon disulfide (50 mmol, 3.04 mL), the reaction mixture being stirred at room temperature overnight. Sodium chloroacetate (50 mmol, 5.943 g) was then added, the reaction mixture being stirred at room temperature overnight. Aqueous hydrochloric acid (37% m/v) was then added until pH=1, the reaction mixture being stirred and heated at reflux overnight. After cooling to room temperature, the yellowish solid that precipitated from the crude product mixture was filtered under reduced pressure, washed with distilled water and dried at room temperature under vacuum, yielding 3-(3'-hydroxycarbonylpropyl)-2-thioxothiazolidin-4-one as a pale-yellow solid. See, e.g., (FIG. 3).

Example 41

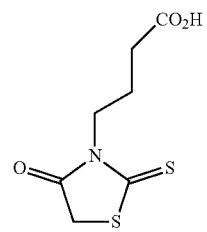 [SMILES: O=C(O)CCCN1C(=O)CSC1=S]

3-(3'-hydroxycarbonylpropyl)-2-thioxothiazolidin-4-one

Yield: 27%, 2.950 g; mp (° C.): 118-119; $^1$H NMR (400 MHz, $(CD_3)_2SO/CCl_4$): δ, ppm=4.13 (2H, s, $CH_2$), 3.97 (2H, t, J=7.4 Hz, $NCH_2CH_2CH_2CO_2H$), 2.25 (2H, t, J=7.4 Hz, $NCH_2CH_2CH_2CO_2H$), 1.84-1.91 (2H, m, $NCH_2CH_2CH_2CO_2H$); $^{13}$C NMR (100 MHz, $(CD_3)_2SO/CCl_4$): δ, ppm=201.9, 173.7, 173.2, 43.2, 35.2, 30.9, 21.8.

The Z stereoisomeric forms of compounds AT50-B00, AT50-C00, AT50-C01, AT50-C02 and both the E and Z stereoisomers of compound AT50-A00 were commercially acquired and used as received.

Example 42

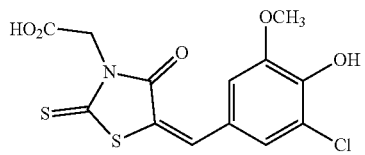 [SMILES: COc1cc(/C=C2/SC(=S)N(CC(=O)O)C2=O)cc(Cl)c1O]

107

(E)-3-hydroxycarbonylmethyl-5-(3'-chloro-4'-hydroxy-5'-methoxyphenylmethylidene)-2-thioxothiazolidin-4-one, AT50-A00 (E)

Example 43

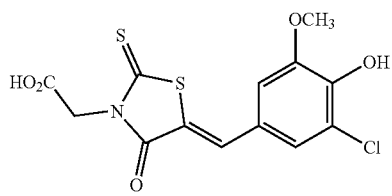 [SMILES: COc1cc(/C=C2\SC(=S)N(CC(=O)O)C2=O)cc(Cl)c1O]

(Z)-3-hydroxycarbonylmethyl-5-(3'-chloro-4'-hydroxy-5'-methoxyphenylmethylidene)-2-thioxothiazolidin-4-one, AT50-A00 (Z)

Example 44

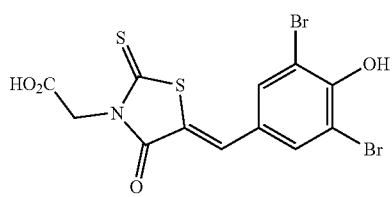 [SMILES: O=C(O)CN1C(=O)/C(=C/c2cc(Br)c(O)c(Br)c2)SC1=S]

(Z)-5-(3',5'-dibromo-4'-hydroxyphenylmethylidene)-3-hydroxycarbonylmethyl-2-thioxothiazolidin-4-one, AT50-A50

Example 45

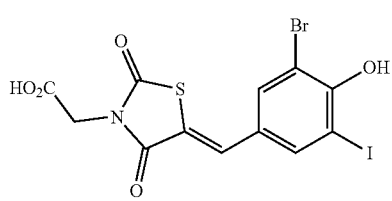 [SMILES: O=C(O)CN1C(=O)S/C(=C\c2cc(Br)c(O)c(I)c2)C1=O]

(Z)-5-(3'-bromo-4'-hydroxy-5'-iodophenylmethylidene)-3-hydroxycarbonylmethyl-2,4-dioxothiazolidine, AT50-A51

Example 46

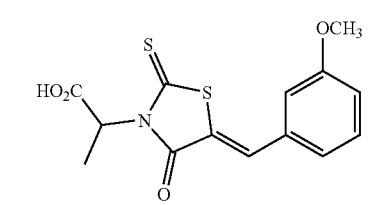 [SMILES: COc1cccc(/C=C2\SC(=S)N(C(C)C(=O)O)C2=O)c1]

108

(Z)-3-(1'-hydroxycarbonylethyl)-5-(3'-methoxyphenylmethylidene)-2-thioxothiazolidin-4-one, AT-50-B00

Example 47

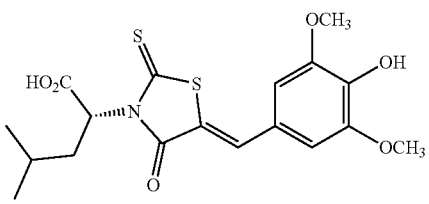 [SMILES: COc1cc(/C=C2\SC(=S)N([C@H](CC(C)C)C(=O)O)C2=O)cc(OC)c1O]

(Z)-(1'S)-5-(4'-hydroxy-3',5'-dimethoxyphenylmethylidene)-3-(1'-hydroxycarbonylisopentyl)-2-thioxothiazolidin-4-one, AT50-B01

Example 48

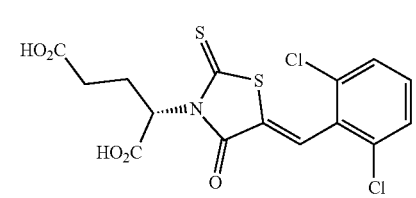 [SMILES: O=C(O)CC[C@@H](C(=O)O)N1C(=O)/C(=C/c2c(Cl)cccc2Cl)SC1=S]

(Z)-(1'S)-5-(2',6'-dichlorophenylmethylidene)-3-(1',3'-di(hydroxycarbonyl)propyl)-2-thioxothiazolidin-4-one, AT50-C00

Example 49

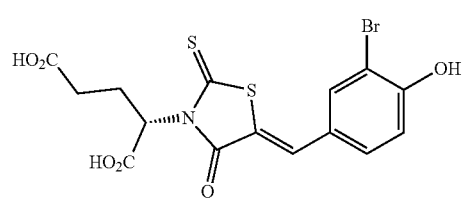 [SMILES: O=C(O)CC[C@@H](C(=O)O)N1C(=O)/C(=C/c2ccc(O)c(Br)c2)SC1=S]

(Z)-(1'S)-5-(3'-bromo-4'-hydroxyphenylmethylidene)-3-(1',3'-di(hydroxycarbonyl)propyl)-2-thioxothiazolidin-4-one, AT50-C01

Example 50

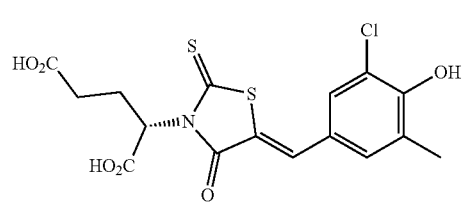 [SMILES: Cc1cc(/C=C2\SC(=S)N([C@@H](CCC(=O)O)C(=O)O)C2=O)cc(Cl)c1O]

(Z)-(1'S)-5-(3'-chloro-4'-hydroxy-5'-methylphenylmethylidene)-3-(1',3'-di(hydroxycarbonyl)propyl)-2-thioxothiazolidin-4-one, AT50-C02

REFERENCES

1. Quintas A, Vaz D C, Cardoso I, Saraiva M J, Brito R M. Tetramer dissociation and monomer partial unfolding precedes protofibril formation in amyloidogenic transthyretin variants. J. Biol. Chem. 276(29), 27207-13 (2001).
2. Miroy G J, Lai Z, Lashuel H a, Peterson S a, Strang C, Kelly J W. Inhibiting transthyretin amyloid fibril formation via protein stabilization. Proc. Natl. Acad. Sci. USA 93(26), 15051-6 (1996).
3. Johnson S M, Connelly S, Fearns C, Powers E T, Kelly J W. The transthyretin amyloidoses: from delineating the molecular mechanism of aggregation linked to pathology to a regulatory-agency-approved drug. J. Mol. Biol. 421 (2-3), 185-203 (2012).
4. Coelho T, Maia L F, Waddington M, Kelly J W, Chan J, Packman J. Tafamidis for transthyretin familial amyloid polyneuropathy. Neurology, 785-792 (2012).
5. Sipe J D, Cohen A S. Review: history of the amyloid fibril. J. Struct. Biol. 130(2-3), 88-98 (2000).
6. Merlini G, Westermark P. The systemic amyloidoses: clearer understanding of the molecular mechanisms offers hope for more effective therapies. J. Intern. Med. 255(2), 159-78 (2004).
7. Sipe J D, Benson M D, Buxbaum J N, et al. Amyloid fibril protein nomenclature: 2012 recommendations from the Nomenclature Committee of the International Society of Amyloidosis. Amyloid 19(4), 167-70 (2012).
8. Benson M D. The hereditary amyloidoses. Best Pract. Res. Clin. Rheumatol. 17(6), 909-27 (2003).
9. Ingbar S H. Pre-albumin: a thyroxine binding protein of human plasma. Endocrinology 63(2), 256-9 (1958).
10. Dickson P W, Schreiber G. High levels of messenger RNA for transthyretin (prealbumin) in human choroid plexus. Neurosci. Lett. 33(3), 311-5 (1986).
11. Ong D E, Davis J T, O'Day W T, Bok D. Synthesis and secretion of retinol-binding protein and transthyretin by cultured retinal pigment epithelium. Biochemistry 33(7), 1835-42 (1994).
12. Westermark G T, Westermark P. Transthyretin and amyloid in the islets of Langerhans in type-2 diabetes. Exp. Diabetes Res. 2008, 429274 (2008).
13. Buxbaum J N, Reixach N. Transthyretin: the Servant of Many Masters. Cell. Mol. Life Sci. 66(19), 3095-3101 (2009).
14. Colon W, Kelly J W. Partial denaturation of transthyretin is sufficient for amyloid fibril formation in vitro. Biochemistry 31(36), 8654-8660 (1992).
15. Jacobson D R, Pastore R D, Yaghoubian R, et al. Variant-sequence transthyretin (isoleucine 122) in late-onset cardiac amyloidosis in black Americans. N. Engl. J. Med. 336(7), 466-73 (1997).
16. Ando Y, Nakamura M, Araki S. Transthyretin-related familial amyloidotic polyneuropathy. Arch. Neurol. 62(7), 1057 (2005).
17. Andrade C. A peculiar form of peripheral neuropathy; familiar atypical generalized amyloidosis with special involvement of the peripheral nerves. Brain 75(3), 408-27 (1952).
18. Jenne D E, Denzel K, Blatzinger P, et al. A new isoleucine substitution of Val-20 in transthyretin tetramers selectively impairs dimer-dimer contacts and causes systemic amyloidosis. Proc. Natl. Acad. Sci. USA 93(13), 6302-7 (1996).
19. Afolabi I, Hamidi Asl K, Nakamura M, Jacobs P, Hendrie H, Benson M D. Transthyretin isoleucine-122 mutation in African and American blacks. Amyloid 7(2), 121-5 (2000).
20. Simões C J V, Mukherjee T, Brito R M M, Jackson R M. Toward the Discovery of Functional Transthyretin Amyloid Inhibitors: Application of Virtual Screening Methods. J. Chem. Inf. Model. 50(10), 1806-1820 (2010).
21. Lipinski C A. Drug-like properties and the causes of poor solubility and poor permeability. J. Pharmacol. Toxicol. Methods. 44, 235-249 (2000).
22. Peterson S a, Klabunde T, Lashuel H a, Purkey H, Sacchettini J C, Kelly J W. Inhibiting transthyretin conformational changes that lead to amyloid fibril formation. Proc. Natl. Acad. Sci. USA 95(22), 12956-60 (1998).
23. Almeida M R, Macedo B, Cardoso I, et al. Selective binding to transthyretin and tetramer stabilization in serum from patients with familial amyloidotic polyneuropathy by an iodinated diflunisal derivative. Biochem. J. 381, 351-356 (2004).
24. Cardoso I, Almeida M R, Ferreira N, Arsequell G, Valencia G, Saraiva M J. Comparative in vitro and ex vivo activities of selected inhibitors of transthyretin aggregation: relevance in drug design. Biochem. J. 408(1), 131-8 (2007).
25. Lipinski C A. Experimental and Computational Approaches to Estimate Solubility and Permeability in Drug Discovery and Development Settings. Adv. Drug Deliv. Rev. 46, 3-26 (2001).
26. Mills J E, Dean P M. Three-Dimensional Hydrogen-Bond Geometry and Probability Information from a Crystal Survey. J. Comput. Aided Mol. Des. 10(6), 607-622 (1996).
27. Veber D F, Johnson S R, Cheng H-Y, Smith B R, Ward K W, Kopple K D. Molecular Properties That Influence the Oral Bioavailability of Drug Candidates. J. Med. Chem. 45(12), 2615-2623 (2002).
28. Martin Y C. A bioavailability score. J. Med. Chem. 48(9), 3164-3170 (2005).
29. Egan W J, Merz K M, Baldwin J J. Prediction of Drug Absorption Using Multivariate Statistics. J. Med. Chem. 43(21), 3867-3877 (2000).
30. McGovern S L, Helfand B T, Feng B, Shoichet B K. A Specific Mechanism of Nonspecific Inhibition. J. Med. Chem. 46(20), 4265-4272 (2003).
31. Seidler J, McGovern S L, Doman T N, Shoichet B K. Identification and Prediction of Promiscuous Aggregating Inhibitors Among Known Drugs. J. Med. Chem. 46(21), 4477-4486 (2003).
32. Lans M C, Klasson-Wehler E, Willemsen M, Meussen E, Safe S H, Brouwer A. Structure-dependent, competitive interaction of hydroxy-polychlorobiphenyls, -dibenzo-p-dioxins and -dibenzofurans with human transthyretin. Chem. Biol. Interact. 88, 7-21 (1993).
33. Wojtczak A, Cody V, Luft J R, Pangborn W. Structures of Human Transthyretin Complexed with Thyroxine at 2.0 A Resolution and 3',5'-Dinitro-N-Acetyl-L-Thyronine at 2.2 A Resolution. Acta Crystallogr. D Biol. Crystallogr. 52(Pt 4), 758-765 (1996).
34. Petrassi H M, Klabunde T, Sacchettini J, Kelly J W. Structure-Based Design of N-Phenyl Phenoxazine Transthyretin Amyloid Fibril Inhibitors. J. Am. Chem. Soc. 122(10), 2178-2192 (2000).

35. Klabunde T, Petrassi H M, Oza V B, Raman P, Kelly J W, Sacchettini J C. Rational design of potent human transthyretin amyloid disease inhibitors. Nat. Struct. Biol. 7, 312-321 (2000).
36. Purkey H E, Palaninathan S K, Kent K C, et al. Hydroxylated Polychlorinated Biphenyls Selectively Bind Transthyretin in Blood and Inhibit Amyloidogenesis: Rationalizing Rodent PCB Toxicity. Chem. Biol. 11(12), 1719-1728 (2004).
37. Oza V B, Smith C, Raman P, et al. Synthesis, Structure, and Activity of Diclofenac Analogues as Transthyretin Amyloid Fibril Formation Inhibitors. J. Med. Chem. 45(2), 321-332 (2002).
38. Adamski-Werner S L, Palaninathan S K, Sacchettini J C, Kelly J W. Diflunisal Analogues Stabilize the Native State of Transthyretin. Potent Inhibition of Amyloidogenesis. J. Med. Chem. 47(2), 355-374 (2004).
39. Berman H M, Westbrook J, Feng Z, et al. The Protein Data Bank. Nucleic Acids Res. 28(1), 235-42 (2000).
40. Protein P, Raz A, Goodman D S. MACROMOLECULES: The Interaction of Thyroxine with Human Plasma Prealbumin and with the Prealbumin-Retinal-binding Protein Complex*. (1969).
41. Lawrence N J, Hepworth L A, Rennison D, McGown A T, Hadfield J A. Synthesis and anticancer activity of fluorinated analogues of combretastatin A-4. J. Fluor. Chem. 123(1), 101-108 (2003).
42. ACROS. 3,5-dichloro-4-hydroxybenzaldehyde product information (2014). www.acros.com/DesktopModules/Acros_Search_Results/Acros_Search_Results.aspx?search_type=PartOfName&SearchString=3,5-Dichloro-4-hydroxybenzaldehyde.
43. Sinhababu A K, Borchardt R T. Selective Ring Omethylation of Hydroxybenzaldehydes Via Their Mannich Bases. Synth. Commun. 13(8), 677-683 (1983).
44. R. A. Radu, Y. Han, T. V. Bui, S. Nusinowitz, D. Bok, J. Lichter, et al., Reductions in Serum Vitamin A Arrest Accumulation of Toxic Retinal Fluorophores: A Potential Therapy for Treatment of Lipofuscin-Based Retinal Diseases, Investig. Opthalmology Vis. Sci. 46 (2005) 4393. doi:10.1167/iovs.05-0820.
45. R. Berni, F. Formelli, In vitro interaction of fenretinide with plasma retinol-binding protein and its functional consequences, FEBS Lett. 308 (1992) 43-45. doi: 10.1016/0014-5793(92)81046-O.
46. J. T. White, J. W. Kelly, Support for the multigenic hypothesis of amyloidosis: the binding stoichiometry of retinol-binding protein, vitamin A, and thyroid hormone influences transthyretin amyloidogenicity in vitro, Proc. Natl. Acad. Sci. USA. 98 (2001) 13019-13024. doi: 10.1073/pnas.241406698.
47. S.-J. Hyung, S. Deroo, C. V. Robinson, Retinol and Retinol-Binding Protein Stabilize Transthyretin via Formation of Retinol Transport Complex, ACS Chem. Biol. 5 (2010) 1137-1146. doi:10.1021/cb100144v.
48. J. N. Buxbaum, N. Reixach, Transthyretin: the Servant of Many Masters, Cell. Mol. Life Sci. 66 (2009) 3095-3101. doi:10.1007/s00018-009-0109-0.
49. K. Petrukhin, New therapeutic targets in atrophic age-related macular degeneration, Expert Opin. Ther. Targets. 11 (2007) 625-39. doi:10.1517/14728222.11.5.625.
50. N. J. Lawrence, L. A. Hepworth, D. Rennison, A. T. McGown, J. A. Hadfield, Synthesis and anticancer activity of fluorinated analogues of combretastatin A-4, J. Fluor. Chem. 123 (2003) 101-108. doi:10.1016/50022-1139(03)00117-9.
51. A. K. Sinhababu, R. T. Borchardt, Selective Ring Omethylation of Hydroxybenzaldehydes Via Their Mannich Bases, Synth. Commun. 13 (1983) 677-683. doi: 10.1080/00397918308060349.
52. M. F. Ansell, A. J. Bignold, A. F. Gosden, V. J. Leslie, R. A. Murray, The Diels-Alder reactions of o-benzoquinones with acyclic dienes, J. Chem. Soc. C. (1971) 1414. doi:10.1039/j39710001414.

All publications, patents, and sequence database entries mentioned herein are incorporated by reference in their entirety as if each individual publication, patent, or database entries was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method of inhibiting amyloid fibril formation in a subject, the method comprising administering to a subject in need thereof a compound of Formula (II):

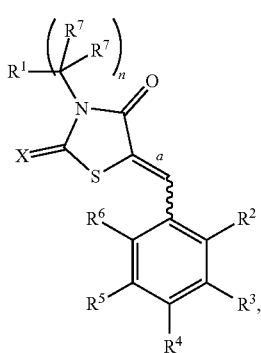

or a pharmaceutically acceptable salt, solvate, hydrate, tautomer, stereoisomer, or prodrug thereof, wherein:

the double bond labeled with "a" is of (E)- or (Z)-configuration;

$R^1$ is —C(=O)O$R^a$, —S(=O)$_2$NH$R^a$, —S(=O)$_2$O$R^a$, —P(=O)NH$_2$(O$R^a$), —C(=O)N($R^a$)$_2$, —C(=O)NHO$R^a$, —CHN$_4$ (tetrazolyl), or —O$R^a$;

$R^2$ is H or Halogen;

$R^3$ is H, —OH, Halogen, —CH$_3$, or —OCH$_3$;

$R^4$ is H, —O$R^a$, F, —OCH$_3$, —NH$_2$, —ONH$_2$, —NCH$_2$, —CN, or —SH;

$R^5$ is H, —OH, Halogen, —CH$_3$, or —OCH$_3$;

$R^6$ is H or Halogen;

each instance of $R^7$ is independently H, substituted or unsubstituted C$_{1-6}$ alkyl, —C(=O)O$R^a$, or —C(=O)N($R^a$)$_2$;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

n is 1, 2, or 3; and

X is S.

2. A method of treating an amyloid disease, the method comprising administering to a subject in need thereof a compound of Formula (II):

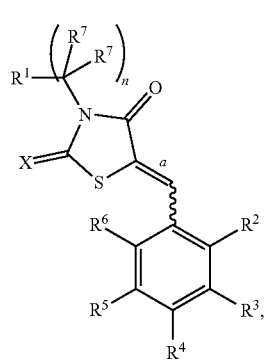

or a pharmaceutically acceptable salt, solvate, hydrate, tautomer, stereoisomer, or prodrug thereof, wherein:

the double bond labeled with "a" is of (E)- or (Z)-configuration;

$R^1$ is —C(=O)O$R^a$, —S(=O)$_2$NH$R^a$, —S(=O)$_2$O$R^a$, —P(=O)NH$_2$(O$R^a$), —C(=O)N($R^a$)$_2$, —C(=O)NHO$R^a$, —CHN$_4$ (tetrazolyl), or —O$R^a$;

$R^2$ is H or Halogen;

$R^3$ is H, —OH, Halogen, —CH$_3$, or —OCH$_3$;

$R^4$ is H, —O$R^a$, F, —OCH$_3$, —NH$_2$, —ONH$_2$, —NCH, —CN, or —SH;

$R^5$ is H, —OH, Halogen, —CH$_3$, or —OCH$_3$;

$R^6$ is H or Halogen;

each instance of $R^7$ is independently H, substituted or unsubstituted C$_{1-6}$ alkyl, —C(=O)O$R^a$, or —C(=O)N($R^a$)$_2$;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

n is 1, 2, or 3; and

X is S.

3. The method of claim 2, wherein the amyloid disease is AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

4. The method of claim 2, wherein the amyloid disease is Familial Amyloid Polyneuropathy.

5. The method of claim 2, wherein the amyloid disease is Familial Amyloid Cardiomyopathy.

6. The method of claim 2, wherein the amyloid disease is Senile Systemic Amyloidosis.

7. The method of claim 2, wherein the amyloid disease is Alzheimer's Disease.

8. A method of treating Macular Degeneration, Stargardt's disease, or a related oculopathy, the method comprising administering to a subject in need thereof a compound of Formula (II):

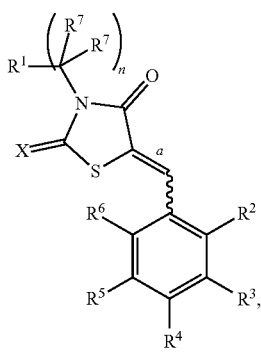

(II)

or a pharmaceutically acceptable salt, solvate, hydrate, tautomer, stereoisomer, or prodrug thereof, wherein:
the double bond labeled with "a" is of (E)- or (Z)-configuration;
$R^1$ is —C(=O)$OR^a$, —S(=O)$_2$$NHR^a$, —S(=O)$_2$$OR^a$, —P(=O)$NH_2$($OR^a$), —C(=O)N($R^a$)$_2$, —C(=O)$NHOR^a$, —$CHN_4$ (tetrazolyl), or —$OR^a$;
$R^2$ is H or Halogen;
$R^3$ is H, —OH, Halogen, —$CH_3$, or —$OCH_3$;
$R^4$ is H, —$OR^a$, F, —$OCH_3$, —$NH_2$, —$ONH_2$, —$NCH_2$, —CN, or —SH;
$R^5$ is H, —OH, Halogen, —$CH_3$, or —$OCH_3$;
$R^6$ is H or Halogen;
each instance of $R^7$ is independently H, substituted or unsubstituted $C_{1-6}$ alkyl, —C(=O)$OR^a$, or —C(=O)N($R^a$)$_2$;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

n is 1, 2, or 3; and

X is S.

9. The method of claim 2, wherein the subject is a human.

10. The method of claim 2, wherein the compound is of the formula:

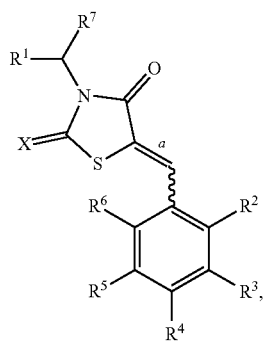

or a pharmaceutically acceptable salt, solvate, hydrate, tautomer, stereoisomer, or prodrug thereof, wherein $R^1$ is —C(=O)$OR^a$, —C(=O)N($R^a$)$_2$, —C(=O)$NHOR^a$, or —$OR^a$.

11. The method of claim 2, wherein the compound is of the formula:

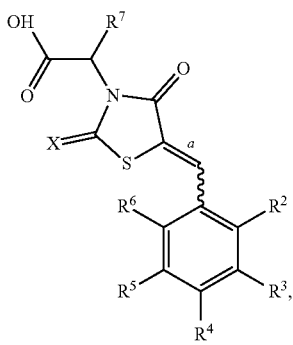

or a pharmaceutically acceptable salt, solvate, hydrate, tautomer, stereoisomer, or prodrug thereof.

12. The method of claim 2, wherein the compound is of the formula:

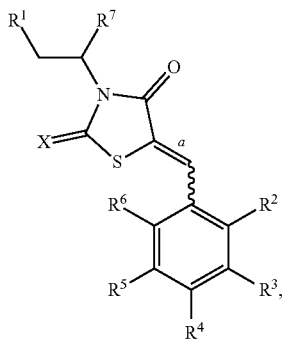

or a pharmaceutically acceptable salt, solvate, hydrate, tautomer, stereoisomer, or prodrug thereof, wherein $R^1$ is —C(=O)$OR^a$, —C(=O)N($R^a$)$_2$, —C(=O)NHO$R^a$, or —O$R^a$.

13. The method of claim 2, wherein the compound is of the formula:

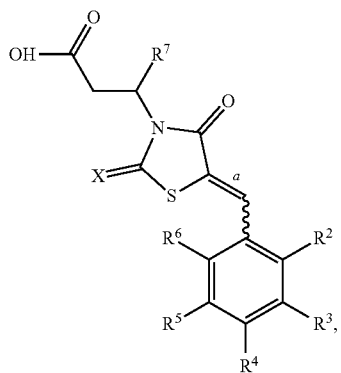

or a pharmaceutically acceptable salt, solvate, hydrate, tautomer, stereoisomer, or prodrug thereof.

14. The method of claim 2, wherein the compound is of the formula:

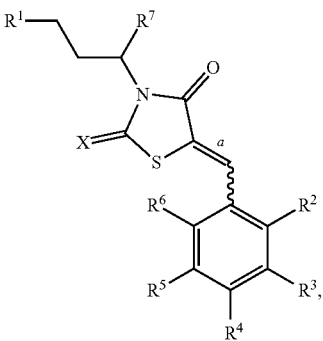

or a pharmaceutically acceptable salt, solvate, hydrate, tautomer, stereoisomer, or prodrug thereof, wherein $R^1$ is —C(=O)$OR^a$, —C(=O)N($R^a$)$_2$, —C(=O)NHO$R^a$, or —O$R^a$.

15. The method of claim 2, wherein the compound is of the formula:

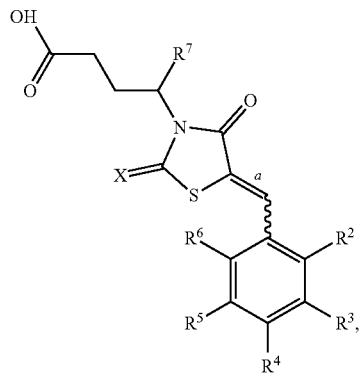

or a pharmaceutically acceptable salt, solvate, hydrate, tautomer, stereoisomer, or prodrug thereof.

16. The method of claim 2, wherein the double bond labeled with "a" is of (Z)-configuration.

17. The method of claim 2, wherein $R^1$ is —C(=O)$OR^a$ or —O$R^a$.

18. The method of claim 2, wherein $R^4$ is H, —O$R^a$, or —CN.

19. The method of claim 2, wherein each instance of $R^7$ is H.

20. The method of claim 2, wherein the compound is of the formula:

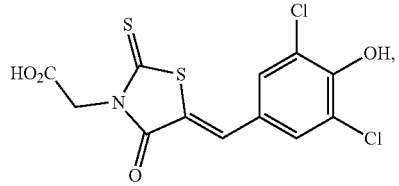

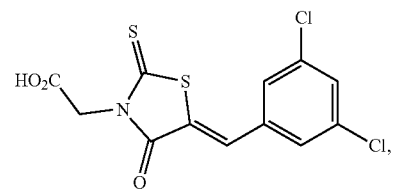

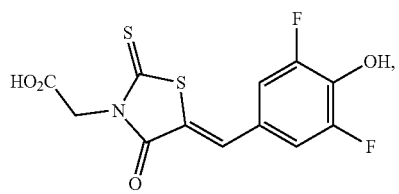

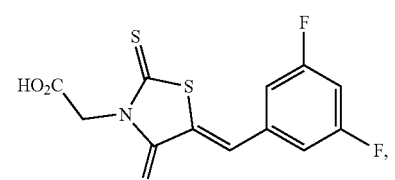

-continued
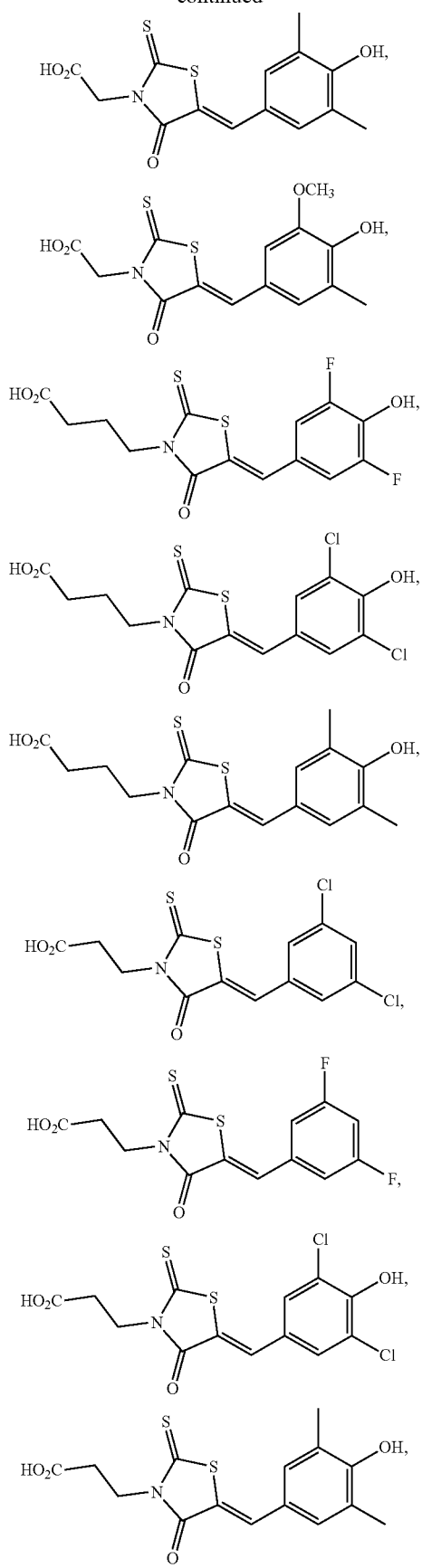
-continued
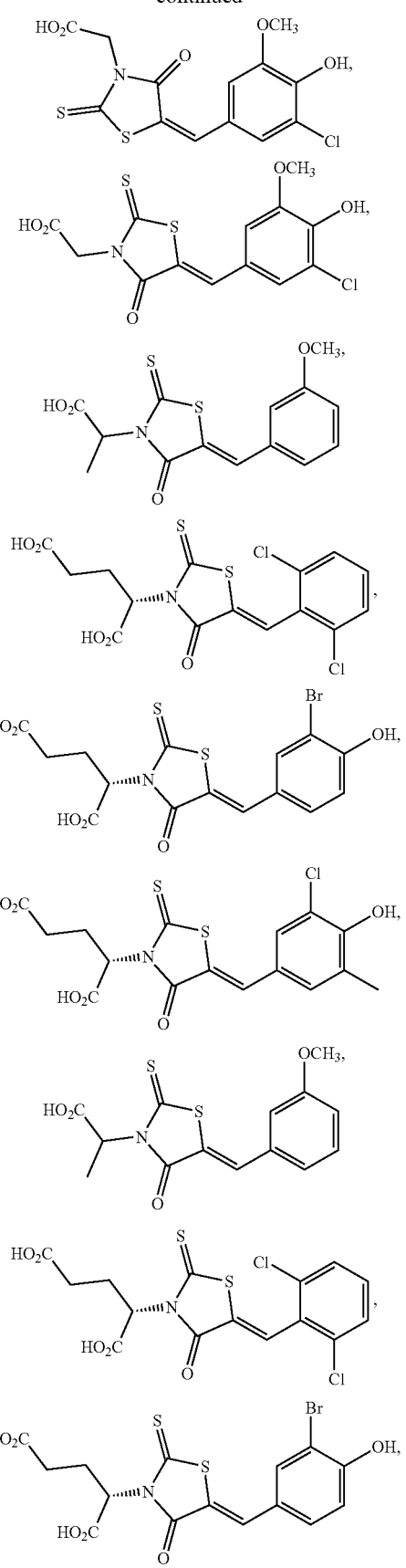

123
-continued
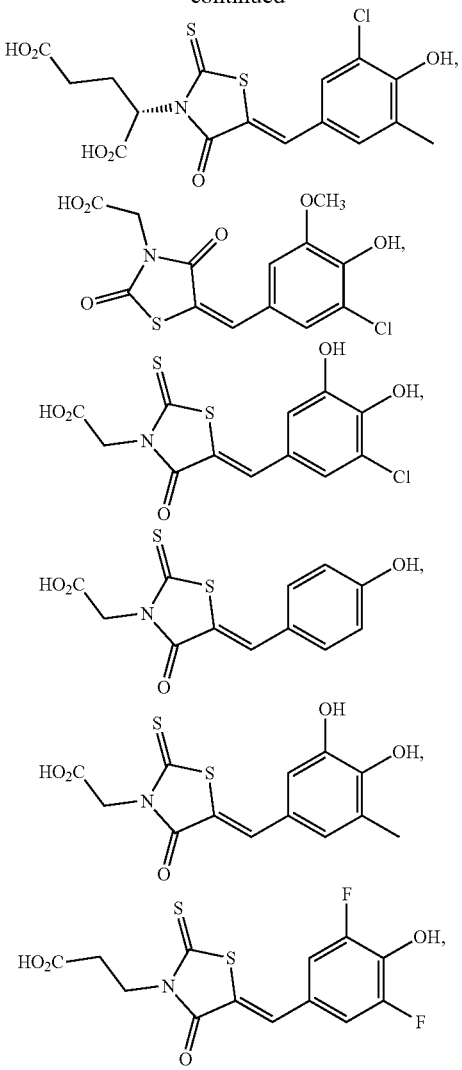
124
-continued
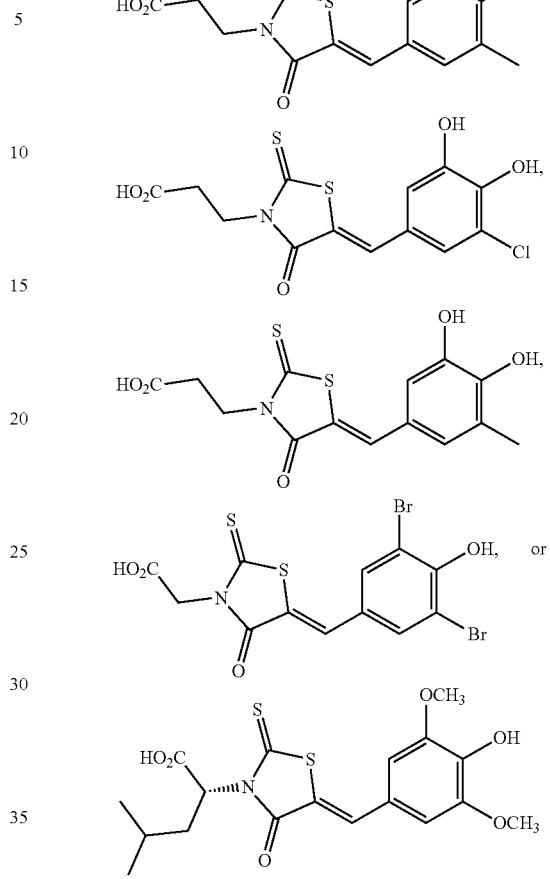
or a pharmaceutically acceptable salt, solvate, hydrate, tautomer, stereoisomer, or prodrug thereof.
* * * * *

UNITED STATES PATENT AND TRADEMARK OFFICE
CERTIFICATE OF CORRECTION

PATENT NO. : 11,584,727 B2
APPLICATION NO. : 17/405506
DATED : February 21, 2023
INVENTOR(S) : Rui Manuel Pontes Meireles Ferreira de Brito et al.

It is certified that error appears in the above-identified patent and that said Letters Patent is hereby corrected as shown below:

In the Claims

In Claim 2, at Column 116, Line 59, the text: "–NCH" should be replaced with: -- –NCH$_2$ --.

Signed and Sealed this
Eighteenth Day of April, 2023

Katherine Kelly Vidal
*Director of the United States Patent and Trademark Office*

```
                              SEQUENCE LISTING

<160> NUMBER OF SEQ ID NOS: 2

<210> SEQ ID NO 1
<211> LENGTH: 147
<212> TYPE: PRT
<213> ORGANISM: Homo sapiens

<400> SEQUENCE: 1

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 2
<211> LENGTH: 147
<212> TYPE: PRT
<213> ORGANISM: Homo sapiens

<400> SEQUENCE: 2

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45
```

```
Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
    130                 135                 140

Pro Lys Asp
145
```